(12) United States Patent
Sanda et al.

(10) Patent No.: US 8,455,615 B2
(45) Date of Patent: Jun. 4, 2013

(54) METHODS AND COMPOSITIONS FOR PROSTATE CANCER IMMUNOTHERAPY

(75) Inventors: Martin G. Sanda, Weston, MA (US); Mohamed S. Arredouani, Belmont, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 12/990,438

(22) PCT Filed: Apr. 30, 2009

(86) PCT No.: PCT/US2009/042338
§ 371 (c)(1),
(2), (4) Date: Jan. 20, 2011

(87) PCT Pub. No.: WO2009/135019
PCT Pub. Date: Nov. 5, 2009

(65) Prior Publication Data
US 2011/0135643 A1    Jun. 9, 2011

Related U.S. Application Data

(60) Provisional application No. 61/126,065, filed on May 1, 2008.

(51) Int. Cl.
*C07K 14/00*    (2006.01)
(52) U.S. Cl.
USPC ..................... 530/326; 530/324; 424/184.1
(58) Field of Classification Search
None
See application file for complete search history.

(56) References Cited

U.S. PATENT DOCUMENTS

| 2006/0127901 A1 | 6/2006 | Chermesh et al. |
| 2007/0212702 A1 | 9/2007 | Tomlins et al. |

FOREIGN PATENT DOCUMENTS

| WO | WO02-72627 | * | 2/2002 |
| WO | WO 2007/033187 | | 3/2007 |
| WO | WO 2007/066423 | | 6/2007 |

OTHER PUBLICATIONS

International Search Report of International Application No. PCT/US2009/042338 mailed on Feb. 16, 2010.
Written Opinion of the International Searching Authority of International Application No. PCT/US2009/042338 mailed on Feb. 16, 2010.
International Preliminary Report on Patentability for International Application No. PCT/US2009/042338, dated Nov. 2, 2010.
Demichelis et al., "TMPRSS2: ERG Gene Fusion Associated with Lethal Prostate Cancer in a Watchful Waiting Cohort," *Oncogene* 26: 4596-4599, 2007.
Dudley Me et al., "Adoptive-Cell-Transfer Therapy for the Treatment of Patients with Cancer," *Nature Rev. Cancer* 3: 666-675, 2003.
Elkord E, "Immunology and Immunotherapy Approaches for Prostate Cancer," *Prostate Cancer and Prostatic Diseases* 10: 224-236, 2007.
Kiessling et al., "Advances in Specific Immunotherapy for Prostate Cancer," *European Urology* 53: 694-708, 2008.
Thomas-Kaskel and Veelken, "Active Immunotherapy of Prostate Cancer with a Focus on Dendritic Cells," *Actas Urologicas Espanola* 31: 668-679, 2007.
Thomas-Kaskel et al., "Immunotherapy with Dendritic Cells for Prostate Cancer," *International Journal of Cancer* 121: 467-473, 2007.
Zou, "Regulatory T Cells, Tumour Immunity and Immunotherapy," *Nature Rev. Immunol.* 6: 295-307, 2006.
European Patent Office Communication (EP 09 739 821), dated May 30, 2012.

* cited by examiner

*Primary Examiner* — Yunsoo Kim
(74) *Attorney, Agent, or Firm* — Clark & Elbing LLP; Kristina Bieker Brady

(57) ABSTRACT

The present invention features methods and compositions (e.g., immune response stimulating peptides (e.g., ERG or SIM2 peptides), activated immune cells, antigen-presenting cells, and antibodies or antigen-binding fragments thereof) for generating an immune response for the treatment of cancer (e.g., prostate cancer).

11 Claims, 29 Drawing Sheets

Figure 11

MALQGISVVELSGLAPGPFCAMVLADFGARVVRVDRPGSRYDVSRLGRGKRSLV
LDLKQPRGAAVLRRLCKRSDVLLEPFRRGVMEKLQLGPEILQRENPRLIYARLS
GFGQSGSFCRLAGHDINYLALSGVLSKIGRSGENPYAPLNLLADFAGGLMCAL
GIIMALFDRTRTGKGQVIDANMVEGTAYLSSFLWKTQKLSLWEAPRGQNMLDGG
APFYTYRTADGEFMAVGAIEPQFYELLIKGLGLKSDELPNQMSMDDWPEMKKK
FADVFAEKTKAEWCQIFDGTDACVTPVLFEEVVHHDHNKERGSFITSEEQDVS
PRPAPLLNTPAIPSFKRDPFIGEHTEEILEEFGFSREEIYQLNSDKIIESNKV

KASL (SEQ ID NO:11)

Figure 12

MAAEEVLQTVDHYKTEIERLTKELTETTHEKIQAAEYGLVVLEEKLTLKQQYDELEAEYDSLKQELEQL
KEAFGQSFSIHRKVAEDGETREETLLQESASKEAYYLGKILEMQNELKQSRAVVTNVQAENERLTAVVQ
DLKENNEMVELQRTRMKDEIREYKFREARLLQDYTELEEENITLQKLVSTLKQNQVEYEGLKHEIKRFE
EETVLLNSQLEDAIRLKEIAEHQLEEALETLKNEREQKNNLRKELSQYISLNDNHISISVDGLKFAEDG
SEPNNDDKMNGHIHGPLVKLNGDYRTPTLRKGESLNPVSDLFSELNISEIQKLKQQLMQVEREKAILLA
NLQESQTQLEHTKGALTEQHERVHRLTEHVNAMRGLQSSKELKAELDGEKGRDSGEEAHDYEVDINGLE
ILECKYRVAVTEVIDLKAEIKALKEKYNKSVENYTDEKAKYESKTQMYDEQVTSLEKTTKESGEKMAHM
EKELQKMTSIANENHSTLNTAQDELVTFSEELAQLYHHVCLCNNETPNRVMLDYRQSRVTRSGSLKGP
DDPRGLLSPRLARRGVSSPVETRTSSEPVAKESTEASKEPSPTKTPTISPVITAPPSSPVLDTSDIRKE
PMNIYNLNAIIRDQIKHLQKAVDRSLQLSRQRAAARELAPMIDKDKEALMEEILKLKSLLSTKREQIAT
LRAVLKANKQTAEVALANLKNKYENEKAMVTETMTKLRNELKALKEDAATFSSLRAMFATRCDEYVTQL
DEMQRQLAAAFDEKKTINTLLRMAIQQKLALTQRLEDLEFDHEQSRRSKGKLGKSKIGSPKVSGEASVT
VPTIDTYLLHSQGPQTPNIRVSSGTQRKRQFSPSLCDQSRPRTSGASYLQNLLRVPPDPTSTESFLLKG
PPSMSEFIQGHRLSKEKRLTVAPPDCQQPAASVPPQCSQLAGRQDCPTVSPDTALPEEQPHSSQCAPL
HCLSKPPHP (SEQ ID NO:12)

Figure 13

MALFLDKMGSLQKGNYSSQSGMIPGSWQHKMKLQLILKSSKAYY
VLSDAAMSLQKYGRALRYIKLALQSHDTYCCLCTNMLSEVLLFLSQYLTLCG
DIQLMLAQNANNRAAHLEEFHYQTKEDQEILHSLHRESSCQGVPQAWTTWFT
VGLCSLAHAYLSIQKRGRNIRVLIFALYLFIYFLRRSFALVAQAGVQWCNLG
SLKPPPPGFKQFSCLSLPSSWNYRHAPPCPASPPWPPKVLGLQV (SEQ ID NO:13)

Figure 14

MDYDFKAKLAAERERVEDLFEYEGCKVGRGTYGHVYKARRKDGKDEKEYALKQIEGTGISMSACREI
ALLRELKHPNVIALQKVFLSHSDRKVWLLFDYAEHDLWHIIKFHRASKANKKPMQLPRSMVKSLLYQ
ILDGIHYLHANWVLHRDLKPANILVMGEGPERGRVKIADMGFARLFNSPLKPLADLDPVVTFWYRA
PELLLGARHYTKAIDIWAIGCIFAELLTSEPIFHCRQEDIKTSNPFHHDQLDRIFSVMGFPADKDWE
DIRKMPEYPTLQKDFRRTTYANSSLIKYMEKHKVKPDSKVFLLLQKLLTMDPTKRITSEQALQDPYF
QEDPLPTLDVFAGCQIPYPKREFLNEDDPEEKGDKNQQQQNHQQPTAPPQQAAAPPQAPPPQQNS
TQTNGTAGGAGAGVGGTGAGLQHSQDSSLNQVPNKKPRLGPSGANSGGPVMPSDYQHSSSRLNYQS
SVQGSSQSQSTLGYSSSSQQSSQYHPSHQAHRY (SEQ ID NO:14)

Figure 15

MSGHKCSYPWDLQDRYAQDKSVVNKMQQKYWETKQAFIKATGKKEDEHVVASDADLDAKLELFHSI
QRTCLDLSKAIVLYQKRICFLSQEENELGKFLRSQGFQDKTRAGKMMQATGKALCFSSQQRLALRN
PLCRFHQEVETFRHRAISDTWLTVNRMEQCRTEYRGALLWMKDVSQELDPDLYKQMEKFRKVQTQV
RLAKKNFDKLKMDVCQKVDLLGASRCNLLSHMLATYQTTLLHFWEKTSHTMAAIHESFKGYQPYEF
TTLKSLQDPMKKLVEKEEKKINQQESTDAAVQEPSQLISLEEENQRKESSSFKTEDGKSILSALD
KGSTHTACSGPIDELLDMKSEEGACLGPVAGTPEPEGADKDDLLLSEIFNASSLEEGEFSKEWAA
VFGDGQVKEPVPTMALGEPDPKAQTGSGFLPSQLLDQNMKDIQASLQEPAKAASDLTAWFSLFADL
DPLSNPDAVGKTDKEHELLNA (SEQ ID NO:15)

GDDGGGCDDGDDGDDGGGDDGGGDDGGGDDGGDDDGGDHDD
GDGGYGGDDGGGDGDDDSDDGGDDANDDGGGCHAL
LTSGKD (SEQ ID NO:16)

MAELGAGGDGHRGGDGAVRSETAPDSYKVQDKKNASSRPASAISGQNNHSGNKPDPPPVLR
VDDRQRLARERREEREKQLAAREIVWLEREERARQHYEKHLEERKRLEEQRQKEERRAAV
EEKRRQRLEEDKERHEAVVRRTMERSQKPKQKHNRWSWGGSLHGSPSIHSAARRLQLSPWES
SVVNRLLTPTHSFLARSKSTAALSGEAASCSPIIMPYKAAHSRNSMDRPKLFVTPPEGSSRR
RIIHGTASYKKERERENVLFLTSGTRRAVSPSNPKARQPARSRLWLPSKSLPHLPGTPRPTS
SLPPGSVKAAPAQVRPPSPGNIRPVKREVKVEPEKKDPEKEPQKVANEPSLKGRAPLVKVEE
ATVEERTPAEPEVGPAAPAMAPAPASAPAPASAPAPAPVPTPAMVSAPSSTVNASASVKTSA
GTTDPEEATRLLAEKRRLAREQREKEERERREQELERQKREELAQRVAEERTTRREEESRR
LEAEQAREKEEQLQRQAEERALREREAERAQRQKEEEAVREEAERVQEREKHFQREEQE
RLERKKRLEEIMKRTRRTEATDKKTSDQRNGDIAKGALTGGTEVSALPCTTNAPGNGKPVGS
PHVVTSHQSKVTVESTPDLEKQPNENGVSVQNENFEEIINLPIGSKPSRLDVTNSESPEIPL
NPILAFDDEGTLGPLPQVDGVGTQQTAEVI    (SEQ ID NO:17)

Figure 18

MEDGKPVWAPHPTDGFQMGNIVDIGPDSLTIEPLNQKTFLAL
INQVFPAEEDSKKDVEDNCSLMYLNEATLLHNIKVRYSKDRIYTYVANILIAVNPYFD
IPKIYSSEAIKSYQGKSLGTRPPHVFAIADKAFRDMKVLKMSQSIIVSGESGAGKTEN
TKFVLRYLTESYGTGQDIDDRIVEANPLLEAFGNAKTVRNNNSSRFGKFVEIHFNEKS
SVVGGFVSHYLLEKSRICVQGKEERNYHIFYRLCAGASEDIREKLHLSSPDNFRYLNR
GCTRYFANKETDKQILQNRKSPEYLKAGSMKDPLLDDHGDFIRMCTAMKKIGLDDEEK
LDLFRVVAGVLHLGNIDFEEAGSTSGGCNLKNKSAQSLEYCAELLGLDQDDLRVSLTT
RVMLTTAGGTKGTVIKVPLKVEQANNARDALAKTVYSHLFDHVVNRVNQCFPFETSSY
FIGVLDIAGFEYFEHNSFEQFCINYCNEKLQQFFNERILKEEQELYQKEGLGVNEVHY
VDNQDCIDLIEAKLVGILDILDEENRLPQPSDQHFTSAVHQKHKDHFRLTIPRKSKLA
VHRNIRDDEGFIIRHFAGAVCYETTQFVEKNNDALHMSLESLICESRDKFIRELFESS
TNNNKDTKQKAGKLSFISVGNKFKTQLNLLLDKLRSTGASFIRCIKPNLKMTSHHFEG
AQILSQLQCSGMVSVLDLMQGGYPSRASFHELYNMYKKYMPDKLARLDPRLFCKALFK
ALGLNENDYKFGLTKVFFRPGKFAEFDQIMKSDPDHLAELVKRVNHWLTCSRWKKVQW
CSLSVIKLKNKIKYRAEACIKMQKTIRMWLCKRRHKPRIDGLVKVGTLKKRLDKFNEV
VSVLKDGKPEMNKQIKNLEISIDTLMAKIKSTMMTQEQIQKEYDALVKSSEELLSALQ
KKKQQEEEAERLRRIQEMEKERKRREEDEKRRKEEEERRMKLEMEAKRKQEEEERK
KREDDEKRIQAEVEAQLARQKEEESQQQAVLEQERRDRELALRIAQSEAELISDEAQA
DLALRRNDGTRPKMTPEQMAKEMSEFLSRGPAVLATKAAAGTKKYDLSKWKYAELRDT
INTSCDIELLAACREEFHRRLKVYHAWKSKNKKRNTETEQRAPKSVTDYDFAPFLNNS
PQQNPAAQIPARQREIEMNRQQRFRIPFIRPADQYKDPQSKKKGWWYAHFDGPWIAR
QMELHPDKPPILLVAGKDDMEMCELNLEETGLTRKRGAEILPRQFEEIWERCGGIQYL
QNAIESRQARPTYATAMLQSLLK (SEQ ID NO:18)

Figure 19

MSSCNFTHATFVLIGIPGLEKAHFWVGFPLLSMYVVAMFGNCIV
VFIVRTERSLHAPMYLFLCMLAAIDLALSTSTMPKILALFWFDSREISFEACLTQMFF
IHALSAIESTILLAMAFDRYVAICHPLRHAAVLNNTVTAQIGIVAVVRGSLFFFPLPL
LIKRLAFCHSNVLSHSYCVHQDVMKLAYADTLPNVVYGLTAILLVMGVDVMFISLSYF
LIIRTVLQLPSKSERAKAFGTCVSHIGVVLAFYVPLIGLSVVHRFGNSLHPIVRVVMG
DIYLLLPPVINPIIYGAKTKQIRTRVLAMFKISCDKDLQAVGGK (SEQ ID NO:19)

Figure 20

MATAEVLNIGKKLYEGKTKEVYELLDSPGKVLLQSKDQITAGNA
ARKNHLEGKAAISNKITSCIFQLLQEAGIKTAFTRKCGETAFIAPQCEMIPIEWVCRR
IATGSFLKRNPGVKEGYKFYPPKVELFKDDANNDPQWSEEQLIAAKFCFAGLLIGQT
EVDIMSHATQAIFEILEKSWLPQNCTLVDMKIEFGVDVTTKEIVLADVIDNDSWRLWP
SGDRSQQKDKQSYRDLKEVTPEGLQMVKKNFEWVAERVELLLKSESQCRVVVLMGSTS
DLGHCEKIKKACGNFGIPCELRVTSAHKGPDETLRIKAEYEGDGIPTVFVAVAGRSNG
LGPVMSGNTAYPVISCPPLTPDWGVQDVWSSLRLPSGLGCSTVLSPEGSAQFAAQIFG
LSNHLVWSKLRASILNTWISLKQADKKIRECNL (SEQ ID NO:20)

Figure 21

MPPRAPPAPGPRPPPRAAAATDTAAGAGGAGGAGGAGGPGFRPLAPRPWRLLLALPAACSAPPP
RPVYTNHWAVQVLGGPAEADRVAAAHGYLNLGQNLEDYYHFYHSKTFKRSTLSSRGPHTFLRMDP
QVKWLQQQEVKRRVKRQVRSDPQALYFNDPIWSNMWYLHCGDKNSRCRSEMNVQAAWKRGYTGKNV
VVTILDDGIERNHPDLAPNYDSYASYDVNGNDYDPSPRYDASNENKHGTRCAGEVAASANNSYCIV
GIAYNAKIGGIRMLDGDVTDVVEAKSLGIRPNYIDIYSASWGPDDDGKTVDGPGRLAKQAFEYGIK
KGRQGLGSIFVWASGNGGREGDYCSCDGYTNSIYTISVSSATENGYKPWYLEECASTLATTYSSGA
FYERKIVTTDLRQRCTDGHTGTSVSAPMVAGIIALALEANSQLTWRDVQHLLVKTSRPAHLKASDW
KVNGAGHKVSHFYGFGLVDAEALVVEAKKWTAVPSQHMCVAASDKRPRSIPLVQVLRTTALTSACA
EHSDQRVVYLEHVVVRTSISHPRRGDLQIYLVSPSGTKSQLLAKRLLDLSNEGFTNWEFMTVHCWG
EKAEGQWTLEIQDLPSQVRNPEKQGKLKEWSLILYGTAEHPYHTFSAHQSRSRMLELSAPELEPPK
AALSPSQVEVPEDEEDYTAQSTPGSANILQTSVCHPECGDKGCDGPNADQCLNCVHFSLGSVKTSR
KCVSVCPLGYFGDTAARRCRRCHKGCETCSSRAATQCLSCRRGFYHHQEMNTCVTLCPAGFYADES
QKNCLKCHPSCKKCVDEPEKCTVCKEGFSLARGSCIPDCEPGTYFDSELIRCGECHHTCGTCVGPG
REECIHCAKNFHFHDWKCVPACGEGFYPEEMPGLPHKVCRRCDENCLSCAGSSRNCSRCKTGFTQL
GTSCITNHTCSNADETFCEMVKSNRLCERKLFIQFCCRTCLLAG (SEQ ID NO:21)

Figure 22

```
   1 cgagcacatg ggccgcgggc cgggcgggct cggggcggcc gggacgagga gggcgacga
  61 cgagctgcga gcaaagatgt gcccggac gcccggcacc ttccagtgga tttccttgcg
 121 gaaagatgt tggcgtccc tgtgacctgt ggagacacgg ccagatctgc cctccagcct
 181 gatcttttgg ccagaaggag attaaaaaga tgccccctcaa gatggctgtg ctgtcagctg
 241 catggagctt cgttcaagta tttctgagc ctgatgatt tacagtgatg ttcagtggtc
 301 tgggaataa cgctggtgga accatgcact gaatgacac acgcccggca catttcagga
 361 tactaaaagt ggttttaagg gaggctgtgg ctgaatgcct catggattct tacagcttgg
 421 atgtccatgg gggacgaagg actgcagctg gctgagagg ttgagatctc tgtttactta
 481 gatctctgcc aacttccttt gggtctccct atggaatgta agacccgac tcttcctggt
 541 gaagcatctg atgcacgttc catccggcgc tcagctgggc ttgagctgac catactccct
 601 ggagccttct cccgaggtgg gcggtgacc ttggcacata cagccatcat gatgtactt
 661 taagtggagg ctgaatcatc tcccctttga gctgcttttgg gaacgtgcc ccttgtgt
 721 tcccctttta ctgccaggac actgagattt ggagaggtaa gtggcttacc tgaggccatg
 781 tgctaacaga gaagatgaag agatgattga aacaggccta agaccagacc taaggtctg
 841 tacatttcc acatactttc catatctta gaggcctgac caaagcagat ctttcctt
 901 cttctaggta agtccaaagg cacctgcctg ctgggcccac tgtttctaa cttcctaac
 961 tttctgatcc cttggagtg ataatcaaat attctagtct gaggcattgg gatacatgt
1021 gctaggttct gagactctgc gtcaggcctg aaccctgcat tttgtggagg tgggtgggag
1081 aatgttcccc tgggaacat gcctagacac ggggacaac agttgccctc atggggaggt
1141 acctgtttac tcgctgttat gggaccgctt tcacaaaaac actgcaggtg agtgagttcc
1201 tgcgtgaatat caggcctggt gtctctagac ttattgccat aatccaggcc ccctatgtta
1261 gttcatctcg agccacattt ttattgccat aatccaggcc tggacaggcc aagatctttt
1321 aacaatttta attactgaaa ataataactg cattttttt taaagcccaa ctttttggta
1381 agtcagccca aaatacagtc tttgtgttgc catctgggaa ctggatttgg aattgttctt
1441 ccatgagact gcagagcaga acggcagggc cagaggtccc acgagctggt cagacccggt
1501 tctgctcctt gctgctgag tgaccttggg cattgt (SEQ ID NO:22)
```

Figure 23

MEHIHDSDGSSSSSHQSLKSTAKWAASLENLLEDPEGVKRFREF
LKKEFSEENVLFWLACEDFKKMQDKTQMQEKAKEIYMTFLSSKASSQVNVEGQSRLNEKI
LEEPHPLMFQKLQDQIFNLMKYDSYSRFLKSDLFLKHKRTEEEEDLPDAQTAAKR
ASRIYNT (SEQ ID NO:23)

Figure 24

TTTTGTCACCTTTTTCCTCATTAGAAGGAAAGTAGAAAGCCTTACTTTAGGATTTTAAAAAA
AAAATCCATCTCACCCCATATTGGTCTTAAATAAGTATAGACTAATTAACCTAAGCTACCTTT
AACAACGTAGAATTTAGATGGGTTCATATATGTGAGAAAAACCTGAATATAGACAGGGGTCC
CACTTTTTTCCCCACCTCGTCGCCCAGGCTAGAGTATAGTGGTGTGATCTTGGCCCACTGCA
ACCTCTGCTTCCTAGGTTCAAGTGATTCTCCCTGCCTCAGCCTCCCAAGTAGCTGGGATTGTAA
GAGTATGCCACCACGCCCAGCTACTTTTTGTATTTTAGTAGAGACAGGGTTTCATCATGTTG
GCCAGGATGGTCTCTTAACTCCTGCCCTCAAGTGATCCACCAGAGAGGAGATCCTCGGCCTCC
CCAAGTGCTGGATTATAGGCATGAGCCACCGTGCCCAGCTACTTTCTAATTAATTAAAAAAA
AAAAAAAAAAAAAAAAAAACTTCCCAAATGAGCTGATAGAAAAATGACGTGAGGCTGCTT
TGCCTTCAATAATAACCTAGTTTTCAGCTGTTCCAACTCGTTCCAATAGAAATTAGCTGGAA
CACACTACAGTAATCTCAAGGAAGGGAAAATTAGGCCTTAAAAGATACCAAGAAGTCAGCATG
GTACCCAATTGAAACCTTTTGACCTTAGNGGAATTCATTCTATTGCACTAAAAGCCTTAAC
TGNTGGATTCAGAGTCCTTTAACTGGGAGTTCTATAGAACTTTACTTTTTCCCTAGGCCCAG
AGNGGAGAAGGGTTTCTTAANAGCGGTTCATGGGA (SEQ ID NO:24)

Figure 25

CCGGCGCTTCTTCTGCTTCTTGCTCTCTCGTCGTCCTTGTCGCGGCTGCGGGTGCTGGTGGTC
GGGGTGGGAGGAGCCGGCGTCGCTGTCTCGCGCTTGCGCTTCCGTGATGATTTCTTCTGCCGG
ACCTCCTCTTCGATCTCCCTCCAGCGTGCCCTCCTCGATGGCCTTGAGCCACTGCTTCTCC
GTCAGTGAGTCGCTGTAGTCCACTCCTTGCGGTGGCGGAGCCACGGCCGAACATCTTC
TCCTCCTCCTCCTCACAGGTCAGCCGCTCCACCTCCGCGTCGTCCTTGATGATCCACGAG
GGGAGCTCGTCCTCCTCCATGAGGCGCGGCTTCCGCTTGGGGTTGCGGGCCTCCTCGCGC
CTGCGGTCCAGTCCATGCGCATGAACAGATCAAACTCCTCCTCGTGCCGGCGATCATC
TGGTTGACGGTCTCGTCGTCGGGCACCTCGTCTTCCTCCTCATCCTGCTCCTCGTGCTCC
AGGATGGCCTGCAGGAAGGCGCGCCGCTCATGGCTGGAGGACTTCTGGTCGAACATGCCG
GCCTGNATCACCTTCTGGGTCACGTTGAGCTTGTACTTGGCTGCAGNCTAGATCTTCTNC
TNCACGCTGTNTGCGGTGCAGAGGCGAGCACACGCCACCTCGTTCTGCCCCCGATGC
GTGGGCTCGTCGTCTGCGCTTGCAGGTCCTGGTGAGGGATCCAGTCAGTCGTGTCANAATGATCAC
AGTTCTGCCGACCTGAGTCAGCCGAGCCCCAACCCGTTGCT (SEQ ID NO:25)

Figure 26

MSVAFAAPRQRGKGEITPAAIQKMLDDNNHLIQCIMDSQNKGKTSECSQYQQMLHTN
LVYLATIADSNQNMQSLLPAPPTQNMPMGPGGMNQSGPPPPRSHNMPSDGMVGGGP
PAPHMQNQMNGQMPGPNHMPMQGPGPNQLNMTNSSMNMPSSSHGSMGGYNHSVPSSQ
SMPVQNQMTMSQGQPMGNYGPRPNMSMQPNQGPMHQQPPSQQYNMPQGGQHYQGQ
QPPMGMMGQVNQGNHMMGQRQIPPYRPPQQGPPQQYSGQEDYYGDQYSHGGQGPPEG
MNQQYYPDGNSQYGQQQDAYQGPPPQQGYPPQQQQYPGQQGYPGQQQYPGQQQYGPSQGGPG
PQYPNYPQGQQQYGGYRPTQPGPPQPPQQRPYGYDQGQYGNYQQ (SEQ ID NO:26)

Figure 27 miqtvpdpaahikealsvvsedqslfecaygtphlaktemtasssdy
gqtskmsprvpqqdwlsqpparvtikmecnpsqvngsrnspdecsvak
ggkmvgspdtvgmnygsymeekhmpppnmttnerrvivpadptlwstd
hvrqwlewavkeyglpdvnillfqnidgkelckmtkddfqrltpsyna
dilshlhylretplphltsddvdkalqnsprlmharntggaafifpn
tsvypeatqrittrpdlpyepprrsawtghghptpqskaaqpspstvp
ktedqrpqldpyqilgptssrlanpgsgqiqlwqfllelisdssnssc
itwegtngefkmtdpdevarrwgerkskpnmnydklsralryyydkni
mtkvhgkryaykfdfhgiaqalqphppesslykypsdlpymgsyhahp
qkmnfvaphppalpvtsssffaapnpywnsptggi

Figure 28 mkeksknaaktrrekengefyelakilplpsaitsqldkasiirlttsyl
kmravfpeglgdawgqpsragpldgvakelgshllqtldgfvfvvasdgk
imyisetasvhlglsqveltgnsiyeyihpsdhdemtavltahqplhhhl
lqeyeiersfflrmkcvlakrnagltcsgykvihcsgylkirqymldmsl
ydscyqivglvavgqslppsaiteiklysnmfmfrasldlklifldsrvt
evtgyepqdliektlyhhvhgcdvfhlryahhlllvkgqvttkyyrllsk
rggwvwvqsyatvvhnsrssrphcivsvnyvlteieykelqlsleqvsta
ksqdswrtalstsqetrklvkpkntkmktklrtnpyppqqyssfqmdkle
cgqlgnwrasppasaaappelqphsessdllytpsyslpfsyhyghfpld
shvfsskkpmlpakfgqpqgspcevarfflstlpasgecqwhyanplvps
ssspaknppeppantarhslvpsyeapaaavrrfgedtappsfpscghyr
eepalgpakaarqaardgarlalaraapeccapptpeapgapaqlpfvll
nyhrvlarrgplggaapaasglacapggpeaatgalrlrhpspaatsppg
aplphylgasviitngr (SEQ ID NO:5)

SEQUENCE LISTING

```
<160> NUMBER OF SEQ ID NOS: 88

<210> SEQ ID NO 1
<211> LENGTH: 486
<212> TYPE: PRT
<213> ORGANISM: Homo sapiens

<400> SEQUENCE: 1

Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125
```

```
Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Ser Thr Val Pro
        275                 280                 285

Lys Thr Glu Asp Gln Arg Pro Gln Leu Asp Pro Tyr Gln Ile Leu Gly
290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
        355                 360                 365

Tyr Asp Lys Leu Ser Arg Ala Leu Arg Tyr Tyr Asp Lys Asn Ile
370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Glu Ser Ser Leu Tyr
                405                 410                 415

Lys Tyr Pro Ser Asp Leu Pro Tyr Met Gly Ser Tyr His Ala His Pro
            420                 425                 430

Gln Lys Met Asn Phe Val Ala Pro His Pro Ala Leu Pro Val Thr
        435                 440                 445

Ser Ser Ser Phe Phe Ala Ala Pro Asn Pro Tyr Trp Asn Ser Pro Thr
450                 455                 460

Gly Gly Ile Tyr Pro Asn Thr Arg Leu Pro Thr Ser His Met Pro Ser
465                 470                 475                 480

His Leu Gly Thr Tyr Tyr
                485

<210> SEQ ID NO 2
<211> LENGTH: 9
<212> TYPE: PRT
<213> ORGANISM: Homo sapiens

<400> SEQUENCE: 2

Gly Leu Pro Asp Val Asn Ile Leu Leu
1               5
```

<210> SEQ ID NO 3
<211> LENGTH: 9
<212> TYPE: PRT
<213> ORGANISM: Homo sapiens

<400> SEQUENCE: 3

Gln Leu Trp Gln Phe Leu Leu Glu Leu
1               5

<210> SEQ ID NO 4
<211> LENGTH: 9
<212> TYPE: PRT
<213> ORGANISM: Homo sapiens

<400> SEQUENCE: 4

Phe Val Ala Pro His Pro Pro Ala Leu
1               5

<210> SEQ ID NO 5
<211> LENGTH: 667
<212> TYPE: PRT
<213> ORGANISM: Homo sapiens

<400> SEQUENCE: 5

Met Lys Glu Lys Ser Lys Asn Ala Ala Lys Thr Arg Arg Glu Lys Glu
1               5                   10                  15

Asn Gly Glu Phe Tyr Glu Leu Ala Lys Leu Leu Pro Leu Pro Ser Ala
                20                  25                  30

Ile Thr Ser Gln Leu Asp Lys Ala Ser Ile Ile Arg Leu Thr Thr Ser
            35                  40                  45

Tyr Leu Lys Met Arg Ala Val Phe Pro Glu Gly Leu Gly Asp Ala Trp
        50                  55                  60

Gly Gln Pro Ser Arg Ala Gly Pro Leu Asp Gly Val Ala Lys Glu Leu
65                  70                  75                  80

Gly Ser His Leu Leu Gln Thr Leu Asp Gly Phe Val Phe Val Val Ala
                85                  90                  95

Ser Asp Gly Lys Ile Met Tyr Ile Ser Glu Thr Ala Ser Val His Leu
            100                 105                 110

Gly Leu Ser Gln Val Glu Leu Thr Gly Asn Ser Ile Tyr Glu Tyr Ile
        115                 120                 125

His Pro Ser Asp His Asp Glu Met Thr Ala Val Leu Thr Ala His Gln
130                 135                 140

Pro Leu His His Leu Leu Gln Glu Tyr Glu Ile Glu Arg Ser Phe
145                 150                 155                 160

Phe Leu Arg Met Lys Cys Val Leu Ala Lys Arg Asn Ala Gly Leu Thr
                165                 170                 175

Cys Ser Gly Tyr Lys Val Ile His Cys Ser Gly Tyr Leu Lys Ile Arg
            180                 185                 190

Gln Tyr Met Leu Asp Met Ser Leu Tyr Asp Ser Cys Tyr Gln Ile Val
        195                 200                 205

Gly Leu Val Ala Val Gly Gln Ser Leu Pro Pro Ser Ala Ile Thr Glu
    210                 215                 220

Ile Lys Leu Tyr Ser Asn Met Phe Met Phe Arg Ala Ser Leu Asp Leu
225                 230                 235                 240

Lys Leu Ile Phe Leu Asp Ser Arg Val Thr Glu Val Thr Gly Tyr Glu
                245                 250                 255

Pro Gln Asp Leu Ile Glu Lys Thr Leu Tyr His His Val His Gly Cys

```
                   260                 265                 270
Asp Val Phe His Leu Arg Tyr Ala His His Leu Leu Val Lys Gly
            275                 280                 285

Gln Val Thr Thr Lys Tyr Tyr Arg Leu Leu Ser Lys Arg Gly Gly Trp
            290                 295                 300

Val Trp Val Gln Ser Tyr Ala Thr Val His Asn Ser Arg Ser Ser
305                 310                 315                 320

Arg Pro His Cys Ile Val Ser Val Asn Tyr Val Leu Thr Glu Ile Glu
                325                 330                 335

Tyr Lys Glu Leu Gln Leu Ser Leu Glu Gln Val Ser Thr Ala Lys Ser
                340                 345                 350

Gln Asp Ser Trp Arg Thr Ala Leu Ser Thr Ser Gln Glu Thr Arg Lys
            355                 360                 365

Leu Val Lys Pro Lys Asn Thr Lys Met Lys Thr Lys Leu Arg Thr Asn
            370                 375                 380

Pro Tyr Pro Pro Gln Gln Tyr Ser Ser Phe Gln Met Asp Lys Leu Glu
385                 390                 395                 400

Cys Gly Gln Leu Gly Asn Trp Arg Ala Ser Pro Pro Ala Ser Ala Ala
                405                 410                 415

Ala Pro Pro Glu Leu Gln Pro His Ser Glu Ser Ser Asp Leu Leu Tyr
                420                 425                 430

Thr Pro Ser Tyr Ser Leu Pro Phe Ser Tyr His Tyr Gly His Phe Pro
            435                 440                 445

Leu Asp Ser His Val Phe Ser Ser Lys Lys Pro Met Leu Pro Ala Lys
            450                 455                 460

Phe Gly Gln Pro Gln Gly Ser Pro Cys Glu Val Ala Arg Phe Phe Leu
465                 470                 475                 480

Ser Thr Leu Pro Ala Ser Gly Glu Cys Gln Trp His Tyr Ala Asn Pro
                485                 490                 495

Leu Val Pro Ser Ser Ser Pro Ala Lys Asn Pro Glu Pro Pro
                500                 505                 510

Ala Asn Thr Ala Arg His Ser Leu Val Pro Ser Tyr Glu Ala Pro Ala
            515                 520                 525

Ala Ala Val Arg Arg Phe Gly Glu Asp Thr Ala Pro Pro Ser Phe Pro
            530                 535                 540

Ser Cys Gly His Tyr Arg Glu Glu Pro Ala Leu Gly Pro Ala Lys Ala
545                 550                 555                 560

Ala Arg Gln Ala Ala Arg Asp Gly Ala Arg Leu Ala Leu Ala Arg Ala
                565                 570                 575

Ala Pro Glu Cys Cys Ala Pro Thr Pro Glu Ala Pro Gly Ala Pro
                580                 585                 590

Ala Gln Leu Pro Phe Val Leu Leu Asn Tyr His Arg Val Leu Ala Arg
            595                 600                 605

Arg Gly Pro Leu Gly Gly Ala Pro Ala Ala Ser Gly Leu Ala Cys
            610                 615                 620

Ala Pro Gly Gly Pro Glu Ala Ala Thr Gly Ala Leu Arg Leu Arg His
625                 630                 635                 640

Pro Ser Pro Ala Ala Thr Ser Pro Pro Gly Ala Pro Leu Pro His Tyr
                645                 650                 655

Leu Gly Ala Ser Val Ile Ile Thr Asn Gly Arg
            660                 665

<210> SEQ ID NO 6
<211> LENGTH: 9
```

```
<212> TYPE: PRT
<213> ORGANISM: Homo sapiens

<400> SEQUENCE: 6

Thr Leu Asp Gly Phe Val Phe Val Val
1               5

<210> SEQ ID NO 7
<211> LENGTH: 9
<212> TYPE: PRT
<213> ORGANISM: Homo sapiens

<400> SEQUENCE: 7

Tyr Gln Ile Val Gly Leu Val Ala Val
1               5

<210> SEQ ID NO 8
<211> LENGTH: 9
<212> TYPE: PRT
<213> ORGANISM: Homo sapiens

<400> SEQUENCE: 8

Ser Leu Asp Leu Lys Leu Ile Phe Leu
1               5

<210> SEQ ID NO 9
<211> LENGTH: 9
<212> TYPE: PRT
<213> ORGANISM: Homo sapiens

<400> SEQUENCE: 9

Lys Leu Ile Phe Leu Asp Ser Arg Val
1               5

<210> SEQ ID NO 10
<211> LENGTH: 9
<212> TYPE: PRT
<213> ORGANISM: Homo sapiens

<400> SEQUENCE: 10

Phe Leu Asp Ser Arg Val Thr Glu Val
1               5

<210> SEQ ID NO 11
<211> LENGTH: 382
<212> TYPE: PRT
<213> ORGANISM: Homo sapiens

<400> SEQUENCE: 11

Met Ala Leu Gln Gly Ile Ser Val Glu Leu Ser Gly Leu Ala Pro
1               5                   10                  15

Gly Pro Phe Cys Ala Met Val Leu Ala Asp Phe Gly Ala Arg Val
                20                  25                  30

Arg Val Asp Arg Pro Gly Ser Arg Tyr Asp Val Ser Arg Leu Gly Arg
                35                  40                  45

Gly Lys Arg Ser Leu Val Leu Asp Leu Lys Gln Pro Arg Gly Ala Ala
            50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
                100                 105                 110
```

```
Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Gly Lys
                165                 170                 175

Gly Gln Val Ile Asp Ala Asn Met Val Glu Gly Thr Ala Tyr Leu Ser
                180                 185                 190

Ser Phe Leu Trp Lys Thr Gln Lys Leu Ser Leu Trp Glu Ala Pro Arg
            195                 200                 205

Gly Gln Asn Met Leu Asp Gly Gly Ala Pro Phe Tyr Thr Thr Tyr Arg
        210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270

Asp Val Phe Ala Glu Lys Thr Lys Ala Glu Trp Cys Gln Ile Phe Asp
        275                 280                 285

Gly Thr Asp Ala Cys Val Thr Pro Val Leu Thr Phe Glu Glu Val Val
290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
                325                 330                 335

Ile Pro Ser Phe Lys Arg Asp Pro Phe Ile Gly Glu His Thr Glu Glu
                340                 345                 350

Ile Leu Glu Glu Phe Gly Phe Ser Arg Glu Glu Ile Tyr Gln Leu Asn
            355                 360                 365

Ser Asp Lys Ile Ile Glu Ser Asn Lys Val Lys Ala Ser Leu
        370                 375                 380

<210> SEQ ID NO 12
<211> LENGTH: 975
<212> TYPE: PRT
<213> ORGANISM: Homo sapiens

<400> SEQUENCE: 12

Met Ala Ala Glu Glu Val Leu Gln Thr Val Asp His Tyr Lys Thr Glu
1               5                   10                  15

Ile Glu Arg Leu Thr Lys Glu Leu Thr Glu Thr Thr His Glu Lys Ile
                20                  25                  30

Gln Ala Ala Glu Tyr Gly Leu Val Val Leu Glu Glu Lys Leu Thr Leu
            35                  40                  45

Lys Gln Gln Tyr Asp Glu Leu Glu Ala Glu Tyr Asp Ser Leu Lys Gln
        50                  55                  60

Glu Leu Glu Gln Leu Lys Glu Ala Phe Gly Gln Ser Phe Ser Ile His
65                  70                  75                  80

Arg Lys Val Ala Glu Asp Gly Glu Thr Arg Glu Glu Thr Leu Leu Gln
                85                  90                  95

Glu Ser Ala Ser Lys Glu Ala Tyr Tyr Leu Gly Lys Ile Leu Glu Met
            100                 105                 110
```

-continued

```
Gln Asn Glu Leu Lys Gln Ser Arg Ala Val Val Thr Asn Val Gln Ala
    115                 120                 125
Glu Asn Glu Arg Leu Thr Ala Val Val Gln Asp Leu Lys Glu Asn Asn
130                 135                 140
Glu Met Val Glu Leu Arg Ile Arg Met Lys Asp Glu Ile Arg Glu
145                 150                 155                 160
Tyr Lys Phe Arg Glu Ala Arg Leu Leu Gln Asp Tyr Thr Glu Leu Glu
                165                 170                 175
Glu Glu Asn Ile Thr Leu Gln Lys Leu Val Ser Thr Leu Lys Gln Asn
            180                 185                 190
Gln Val Glu Tyr Glu Gly Leu Lys His Glu Ile Lys Arg Phe Glu Glu
        195                 200                 205
Glu Thr Val Leu Leu Asn Ser Gln Leu Glu Asp Ala Ile Arg Leu Lys
    210                 215                 220
Glu Ile Ala Glu His Gln Leu Glu Glu Ala Leu Glu Thr Leu Lys Asn
225                 230                 235                 240
Glu Arg Glu Gln Lys Asn Asn Leu Arg Lys Glu Leu Ser Gln Tyr Ile
                245                 250                 255
Ser Leu Asn Asp Asn His Ile Ser Ile Ser Val Asp Gly Leu Lys Phe
            260                 265                 270
Ala Glu Asp Gly Ser Glu Pro Asn Asn Asp Asp Lys Met Asn Gly His
        275                 280                 285
Ile His Gly Pro Leu Val Lys Leu Asn Gly Asp Tyr Arg Thr Pro Thr
    290                 295                 300
Leu Arg Lys Gly Glu Ser Leu Asn Pro Val Ser Asp Leu Phe Ser Glu
305                 310                 315                 320
Leu Asn Ile Ser Glu Ile Gln Lys Leu Lys Gln Gln Leu Met Gln Val
                325                 330                 335
Glu Arg Glu Lys Ala Ile Leu Leu Ala Asn Leu Gln Glu Ser Gln Thr
            340                 345                 350
Gln Leu Glu His Thr Lys Gly Ala Leu Thr Glu Gln His Glu Arg Val
        355                 360                 365
His Arg Leu Thr Glu His Val Asn Ala Met Arg Gly Leu Gln Ser Ser
    370                 375                 380
Lys Glu Leu Lys Ala Glu Leu Asp Gly Glu Lys Gly Arg Asp Ser Gly
385                 390                 395                 400
Glu Glu Ala His Asp Tyr Glu Val Asp Ile Asn Gly Leu Glu Ile Leu
                405                 410                 415
Glu Cys Lys Tyr Arg Val Ala Val Thr Glu Val Ile Asp Leu Lys Ala
            420                 425                 430
Glu Ile Lys Ala Leu Lys Glu Lys Tyr Asn Lys Ser Val Glu Asn Tyr
        435                 440                 445
Thr Asp Glu Lys Ala Lys Tyr Glu Ser Lys Ile Gln Met Tyr Asp Glu
    450                 455                 460
Gln Val Thr Ser Leu Glu Lys Thr Thr Lys Glu Ser Gly Glu Lys Met
465                 470                 475                 480
Ala His Met Glu Lys Glu Leu Gln Lys Met Thr Ser Ile Ala Asn Glu
                485                 490                 495
Asn His Ser Thr Leu Asn Thr Ala Gln Asp Glu Leu Val Thr Phe Ser
            500                 505                 510
Glu Glu Leu Ala Gln Leu Tyr His His Val Cys Leu Cys Asn Asn Glu
        515                 520                 525
Thr Pro Asn Arg Val Met Leu Asp Tyr Tyr Arg Gln Ser Arg Val Thr
```

```
            530                 535                 540
Arg Ser Gly Ser Leu Lys Gly Pro Asp Asp Pro Arg Gly Leu Leu Ser
545                 550                 555                 560

Pro Arg Leu Ala Arg Arg Gly Val Ser Ser Pro Val Glu Thr Arg Thr
                565                 570                 575

Ser Ser Glu Pro Val Ala Lys Glu Ser Thr Glu Ala Ser Lys Glu Pro
                580                 585                 590

Ser Pro Thr Lys Thr Pro Thr Ile Ser Pro Val Ile Thr Ala Pro Pro
                595                 600                 605

Ser Ser Pro Val Leu Asp Thr Ser Asp Ile Arg Lys Glu Pro Met Asn
610                 615                 620

Ile Tyr Asn Leu Asn Ala Ile Ile Arg Asp Gln Ile Lys His Leu Gln
625                 630                 635                 640

Lys Ala Val Asp Arg Ser Leu Gln Leu Ser Arg Gln Arg Ala Ala Ala
                645                 650                 655

Arg Glu Leu Ala Pro Met Ile Asp Lys Asp Lys Glu Ala Leu Met Glu
                660                 665                 670

Glu Ile Leu Lys Leu Lys Ser Leu Leu Ser Thr Lys Arg Glu Gln Ile
                675                 680                 685

Ala Thr Leu Arg Ala Val Leu Lys Ala Asn Lys Gln Thr Ala Glu Val
690                 695                 700

Ala Leu Ala Asn Leu Lys Asn Lys Tyr Glu Asn Glu Lys Ala Met Val
705                 710                 715                 720

Thr Glu Thr Met Thr Lys Leu Arg Asn Glu Leu Lys Ala Leu Lys Glu
                725                 730                 735

Asp Ala Ala Thr Phe Ser Ser Leu Arg Ala Met Phe Ala Thr Arg Cys
                740                 745                 750

Asp Glu Tyr Val Thr Gln Leu Asp Glu Met Gln Arg Gln Leu Ala Ala
                755                 760                 765

Ala Glu Asp Glu Lys Lys Thr Leu Asn Thr Leu Arg Met Ala Ile
770                 775                 780

Gln Gln Lys Leu Ala Leu Thr Gln Arg Leu Glu Asp Leu Glu Phe Asp
785                 790                 795                 800

His Glu Gln Ser Arg Arg Ser Lys Gly Lys Leu Gly Lys Ser Lys Ile
                805                 810                 815

Gly Ser Pro Lys Val Ser Gly Glu Ala Ser Val Thr Val Pro Thr Ile
                820                 825                 830

Asp Thr Tyr Leu Leu His Ser Gln Gly Pro Gln Thr Pro Asn Ile Arg
                835                 840                 845

Val Ser Ser Gly Thr Gln Arg Lys Arg Gln Phe Ser Pro Ser Leu Cys
850                 855                 860

Asp Gln Ser Arg Pro Arg Thr Ser Gly Ala Ser Tyr Leu Gln Asn Leu
865                 870                 875                 880

Leu Arg Val Pro Pro Asp Pro Thr Ser Thr Glu Ser Phe Leu Leu Lys
                885                 890                 895

Gly Pro Pro Ser Met Ser Glu Phe Ile Gln Gly His Arg Leu Ser Lys
                900                 905                 910

Glu Lys Arg Leu Thr Val Ala Pro Pro Asp Cys Gln Pro Ala Ala
                915                 920                 925

Ser Val Pro Pro Gln Cys Ser Gln Leu Ala Gly Arg Gln Asp Cys Pro
                930                 935                 940

Thr Val Ser Pro Asp Thr Ala Leu Pro Glu Glu Gln Pro His Ser Ser
945                 950                 955                 960
```

```
Ser Gln Cys Ala Pro Leu His Cys Leu Ser Lys Pro His Pro
            965                 970                 975

<210> SEQ ID NO 13
<211> LENGTH: 244
<212> TYPE: PRT
<213> ORGANISM: Homo sapiens

<400> SEQUENCE: 13

Met Ala Leu Phe Leu Asp Lys Met Gly Ser Leu Gln Lys Gly Asn Tyr
  1               5                  10                  15

Ser Ser Gln Ser Gly Met Ile Pro Gly Ser Trp Gln His Lys Met Lys
             20                  25                  30

Leu Gln Leu Ile Leu Lys Ser Ser Lys Ala Tyr Tyr Val Leu Ser Asp
         35                  40                  45

Ala Ala Met Ser Leu Gln Lys Tyr Gly Arg Ala Leu Arg Tyr Ile Lys
 50                  55                  60

Leu Ala Leu Gln Ser His Asp Thr Tyr Cys Cys Leu Cys Thr Asn Met
 65                  70                  75                  80

Leu Ser Glu Val Leu Leu Phe Leu Ser Gln Tyr Leu Thr Leu Cys Gly
                 85                  90                  95

Asp Ile Gln Leu Met Leu Ala Gln Asn Ala Asn Asn Arg Ala Ala His
            100                 105                 110

Leu Glu Glu Phe His Tyr Gln Thr Lys Glu Asp Gln Glu Ile Leu His
        115                 120                 125

Ser Leu His Arg Glu Ser Ser Cys Gln Gly Val Pro Gln Ala Trp Thr
130                 135                 140

Thr Trp Phe Thr Val Gly Leu Cys Ser Leu Ala His Ala Tyr Leu Ser
145                 150                 155                 160

Ile Gln Lys Arg Gly Arg Asn Ile Arg Val Leu Ile Phe Ala Leu Tyr
                165                 170                 175

Leu Phe Ile Tyr Phe Leu Arg Arg Ser Phe Ala Leu Val Ala Gln Ala
            180                 185                 190

Gly Val Gln Trp Cys Asn Leu Gly Ser Leu Lys Pro Pro Pro Pro Gly
        195                 200                 205

Phe Lys Gln Phe Ser Cys Leu Ser Leu Pro Ser Ser Trp Asn Tyr Arg
    210                 215                 220

His Ala Pro Pro Cys Pro Ala Ser Pro Pro Trp Pro Pro Lys Val Leu
225                 230                 235                 240

Gly Leu Gln Val

<210> SEQ ID NO 14
<211> LENGTH: 502
<212> TYPE: PRT
<213> ORGANISM: Homo sapiens

<400> SEQUENCE: 14

Met Asp Tyr Asp Phe Lys Ala Lys Leu Ala Ala Glu Arg Glu Arg Val
  1               5                  10                  15

Glu Asp Leu Phe Glu Tyr Glu Gly Cys Lys Val Gly Arg Gly Thr Tyr
             20                  25                  30

Gly His Val Tyr Lys Ala Arg Arg Lys Asp Gly Lys Asp Glu Lys Glu
         35                  40                  45

Tyr Ala Leu Lys Gln Ile Glu Gly Thr Gly Ile Ser Met Ser Ala Cys
 50                  55                  60

Arg Glu Ile Ala Leu Leu Arg Glu Leu Lys His Pro Asn Val Ile Ala
 65                  70                  75                  80
```

-continued

```
Leu Gln Lys Val Phe Leu Ser His Ser Asp Arg Lys Val Trp Leu Leu
                85                  90                  95
Phe Asp Tyr Ala Glu His Asp Leu Trp His Ile Ile Lys Phe His Arg
            100                 105                 110
Ala Ser Lys Ala Asn Lys Lys Pro Met Gln Leu Pro Arg Ser Met Val
        115                 120                 125
Lys Ser Leu Leu Tyr Gln Ile Leu Asp Gly Ile His Tyr Leu His Ala
    130                 135                 140
Asn Trp Val Leu His Arg Asp Leu Lys Pro Ala Asn Ile Leu Val Met
145                 150                 155                 160
Gly Glu Gly Pro Glu Arg Gly Arg Val Lys Ile Ala Asp Met Gly Phe
                165                 170                 175
Ala Arg Leu Phe Asn Ser Pro Leu Lys Pro Leu Ala Asp Leu Asp Pro
            180                 185                 190
Val Val Val Thr Phe Trp Tyr Arg Ala Pro Glu Leu Leu Leu Gly Ala
        195                 200                 205
Arg His Tyr Thr Lys Ala Ile Asp Ile Trp Ala Ile Gly Cys Ile Phe
    210                 215                 220
Ala Glu Leu Leu Thr Ser Glu Pro Ile Phe His Cys Arg Gln Glu Asp
225                 230                 235                 240
Ile Lys Thr Ser Asn Pro Phe His His Asp Gln Leu Asp Arg Ile Phe
                245                 250                 255
Ser Val Met Gly Phe Pro Ala Asp Lys Asp Trp Glu Asp Ile Arg Lys
            260                 265                 270
Met Pro Glu Tyr Pro Thr Leu Gln Lys Asp Phe Arg Arg Thr Thr Tyr
        275                 280                 285
Ala Asn Ser Ser Leu Ile Lys Tyr Met Glu Lys His Lys Val Lys Pro
    290                 295                 300
Asp Ser Lys Val Phe Leu Leu Leu Gln Lys Leu Leu Thr Met Asp Pro
305                 310                 315                 320
Thr Lys Arg Ile Thr Ser Glu Gln Ala Leu Gln Asp Pro Tyr Phe Gln
                325                 330                 335
Glu Asp Pro Leu Pro Thr Leu Asp Val Phe Ala Gly Cys Gln Ile Pro
            340                 345                 350
Tyr Pro Lys Arg Glu Phe Leu Asn Glu Asp Asp Pro Glu Glu Lys Gly
        355                 360                 365
Asp Lys Asn Gln Gln Gln Gln Asn Gln His Gln Gln Pro Thr Ala
    370                 375                 380
Pro Pro Gln Gln Ala Ala Ala Pro Gln Ala Pro Pro Gln Gln
385                 390                 395                 400
Asn Ser Thr Gln Thr Asn Gly Thr Ala Gly Gly Ala Gly Ala Gly Val
                405                 410                 415
Gly Gly Thr Gly Ala Gly Leu Gln His Ser Gln Asp Ser Ser Leu Asn
            420                 425                 430
Gln Val Pro Pro Asn Lys Lys Pro Arg Leu Gly Pro Ser Gly Ala Asn
        435                 440                 445
Ser Gly Gly Pro Val Met Pro Ser Asp Tyr Gln His Ser Ser Ser Arg
    450                 455                 460
Leu Asn Tyr Gln Ser Ser Val Gln Gly Ser Ser Gln Ser Gln Ser Thr
465                 470                 475                 480
Leu Gly Tyr Ser Ser Ser Ser Gln Gln Ser Ser Gln Tyr His Pro Ser
                485                 490                 495
His Gln Ala His Arg Tyr
```

```
<210> SEQ ID NO 15
<211> LENGTH: 483
<212> TYPE: PRT
<213> ORGANISM: Homo sapiens

<400> SEQUENCE: 15

Met Ser Gly His Lys Cys Ser Tyr Pro Trp Asp Leu Gln Asp Arg Tyr
1               5                   10                  15

Ala Gln Asp Lys Ser Val Val Asn Lys Met Gln Gln Lys Tyr Trp Glu
                20                  25                  30

Thr Lys Gln Ala Phe Ile Lys Ala Thr Gly Lys Lys Glu Asp Glu His
            35                  40                  45

Val Val Ala Ser Asp Ala Asp Leu Asp Ala Lys Leu Glu Leu Phe His
        50                  55                  60

Ser Ile Gln Arg Thr Cys Leu Asp Leu Ser Lys Ala Ile Val Leu Tyr
65                  70                  75                  80

Gln Lys Arg Ile Cys Phe Leu Ser Gln Glu Glu Asn Glu Leu Gly Lys
                85                  90                  95

Phe Leu Arg Ser Gln Gly Phe Gln Asp Lys Thr Arg Ala Gly Lys Met
                100                 105                 110

Met Gln Ala Thr Gly Lys Ala Leu Cys Phe Ser Ser Gln Gln Arg Leu
            115                 120                 125

Ala Leu Arg Asn Pro Leu Cys Arg Phe His Gln Glu Val Glu Thr Phe
        130                 135                 140

Arg His Arg Ala Ile Ser Asp Thr Trp Leu Thr Val Asn Arg Met Glu
145                 150                 155                 160

Gln Cys Arg Thr Glu Tyr Arg Gly Ala Leu Leu Trp Met Lys Asp Val
                165                 170                 175

Ser Gln Glu Leu Asp Pro Asp Leu Tyr Lys Gln Met Glu Lys Phe Arg
                180                 185                 190

Lys Val Gln Thr Gln Val Arg Leu Ala Lys Lys Asn Phe Asp Lys Leu
            195                 200                 205

Lys Met Asp Val Cys Gln Lys Val Asp Leu Leu Gly Ala Ser Arg Cys
210                 215                 220

Asn Leu Leu Ser His Met Leu Ala Thr Tyr Gln Thr Thr Leu Leu His
225                 230                 235                 240

Phe Trp Glu Lys Thr Ser His Thr Met Ala Ala Ile His Glu Ser Phe
                245                 250                 255

Lys Gly Tyr Gln Pro Tyr Glu Phe Thr Thr Leu Lys Ser Leu Gln Asp
                260                 265                 270

Pro Met Lys Lys Leu Val Glu Lys Glu Lys Lys Ile Asn Gln
            275                 280                 285

Gln Glu Ser Thr Asp Ala Ala Val Gln Glu Pro Ser Gln Leu Ile Ser
        290                 295                 300

Leu Glu Glu Glu Asn Gln Arg Lys Glu Ser Ser Ser Phe Lys Thr Glu
305                 310                 315                 320

Asp Gly Lys Ser Ile Leu Ser Ala Leu Asp Lys Gly Ser Thr His Thr
                325                 330                 335

Ala Cys Ser Gly Pro Ile Asp Glu Leu Leu Asp Met Lys Ser Glu Glu
            340                 345                 350

Gly Ala Cys Leu Gly Pro Val Ala Gly Thr Pro Glu Pro Glu Gly Ala
        355                 360                 365

Asp Lys Asp Asp Leu Leu Leu Leu Ser Glu Ile Phe Asn Ala Ser Ser
```

```
                  370                 375                 380
Leu Glu Glu Gly Glu Phe Ser Lys Glu Trp Ala Ala Val Phe Gly Asp
385                 390                 395                 400

Gly Gln Val Lys Glu Pro Val Pro Thr Met Ala Leu Gly Glu Pro Asp
                405                 410                 415

Pro Lys Ala Gln Thr Gly Ser Gly Phe Leu Pro Ser Gln Leu Leu Asp
            420                 425                 430

Gln Asn Met Lys Asp Leu Gln Ala Ser Leu Gln Glu Pro Ala Lys Ala
        435                 440                 445

Ala Ser Asp Leu Thr Ala Trp Phe Ser Leu Phe Ala Asp Leu Asp Pro
    450                 455                 460

Leu Ser Asn Pro Asp Ala Val Gly Lys Thr Asp Lys Glu His Glu Leu
465                 470                 475                 480

Leu Asn Ala

<210> SEQ ID NO 16
<211> LENGTH: 90
<212> TYPE: PRT
<213> ORGANISM: Homo sapiens

<400> SEQUENCE: 16

Gly Asp Asp Gly Gly Gly Cys Asp Asp Gly Asp Asp Gly Asp Asp
1               5                   10                  15

Asp Gly Gly Gly Asp Gly Gly Gly Asp Gly Asp Gly Gly Asp
                20                  25                  30

Gly Gly Asp Asp Asp Gly Asp His Asp Asp Gly Asp Gly Gly Tyr Gly
            35                  40                  45

Gly Asp Asp Gly Asp Asp Asp Gly Asp Gly Gly Asp Gly Asp Asp
    50                  55                  60

Asp Ser Asp Asp Gly Gly Asp Asp Ala Asn Asp Asp Gly Gly
65                  70                  75                  80

Cys His Ala Leu Leu Thr Ser Gly Lys Asp
                85                  90

<210> SEQ ID NO 17
<211> LENGTH: 712
<212> TYPE: PRT
<213> ORGANISM: Homo sapiens

<400> SEQUENCE: 17

Met Ala Glu Leu Gly Ala Gly Gly Asp Gly His Arg Gly Gly Asp Gly
1               5                   10                  15

Ala Val Arg Ser Glu Thr Ala Pro Asp Ser Tyr Lys Val Gln Asp Lys
                20                  25                  30

Lys Asn Ala Ser Ser Arg Pro Ala Ser Ala Ile Ser Gly Gln Asn Asn
            35                  40                  45

Asn His Ser Gly Asn Lys Pro Asp Pro Pro Val Leu Arg Val Asp
        50                  55                  60

Asp Arg Gln Arg Leu Ala Arg Glu Arg Glu Glu Arg Glu Lys Gln
65                  70                  75                  80

Leu Ala Ala Arg Glu Ile Val Trp Leu Glu Arg Glu Glu Arg Ala Arg
                85                  90                  95

Gln His Tyr Glu Lys His Leu Glu Glu Arg Lys Lys Arg Leu Glu Glu
            100                 105                 110

Gln Arg Gln Lys Glu Glu Arg Arg Ala Ala Val Glu Glu Lys Arg
        115                 120                 125
```

```
Arg Gln Arg Leu Glu Glu Asp Lys Glu Arg His Glu Ala Val Val Arg
130                 135                 140

Arg Thr Met Glu Arg Ser Gln Lys Pro Lys Gln Lys His Asn Arg Trp
145                 150                 155                 160

Ser Trp Gly Gly Ser Leu His Gly Ser Pro Ser Ile His Ser Ala Ala
                165                 170                 175

Arg Arg Leu Gln Leu Ser Pro Trp Glu Ser Ser Val Val Asn Arg Leu
            180                 185                 190

Leu Thr Pro Thr His Ser Phe Leu Ala Arg Ser Lys Ser Thr Ala Ala
        195                 200                 205

Leu Ser Gly Glu Ala Ala Ser Cys Ser Pro Ile Ile Met Pro Tyr Lys
210                 215                 220

Ala Ala His Ser Arg Asn Ser Met Asp Arg Pro Lys Leu Phe Val Thr
225                 230                 235                 240

Pro Pro Glu Gly Ser Ser Arg Arg Ile Ile His Gly Thr Ala Ser
                245                 250                 255

Tyr Lys Lys Glu Arg Glu Arg Asn Val Leu Phe Leu Thr Ser Gly
            260                 265                 270

Thr Arg Arg Ala Val Ser Pro Ser Asn Pro Lys Ala Arg Gln Pro Ala
        275                 280                 285

Arg Ser Arg Leu Trp Leu Pro Ser Lys Ser Leu Pro His Leu Pro Gly
290                 295                 300

Thr Pro Arg Pro Thr Ser Ser Leu Pro Pro Gly Ser Val Lys Ala Ala
305                 310                 315                 320

Pro Ala Gln Val Arg Pro Pro Ser Pro Gly Asn Ile Arg Pro Val Lys
                325                 330                 335

Arg Glu Val Lys Val Glu Pro Glu Lys Lys Asp Pro Glu Lys Glu Pro
            340                 345                 350

Gln Lys Val Ala Asn Glu Pro Ser Leu Lys Gly Arg Ala Pro Leu Val
        355                 360                 365

Lys Val Glu Glu Ala Thr Val Glu Arg Thr Pro Ala Glu Pro Glu
370                 375                 380

Val Gly Pro Ala Ala Pro Ala Met Ala Pro Ala Pro Ser Ala Pro
385                 390                 395                 400

Ala Pro Ala Ser Ala Pro Ala Pro Val Pro Thr Pro Ala Met
                405                 410                 415

Val Ser Ala Pro Ser Ser Thr Val Asn Ala Ser Ala Ser Val Lys Thr
            420                 425                 430

Ser Ala Gly Thr Thr Asp Pro Glu Ala Thr Arg Leu Leu Ala Glu
        435                 440                 445

Lys Arg Arg Leu Ala Arg Glu Gln Arg Glu Lys Glu Glu Arg Glu Arg
450                 455                 460

Arg Glu Gln Glu Glu Leu Glu Arg Gln Lys Arg Glu Glu Leu Ala Gln
465                 470                 475                 480

Arg Val Ala Glu Glu Arg Thr Thr Arg Arg Glu Glu Ser Arg Arg
                485                 490                 495

Leu Glu Ala Glu Gln Ala Arg Glu Lys Glu Gln Leu Gln Arg Gln
            500                 505                 510

Ala Glu Glu Arg Ala Leu Arg Glu Arg Glu Ala Glu Arg Ala Gln
        515                 520                 525

Arg Gln Lys Glu Glu Glu Ala Arg Val Arg Glu Ala Glu Arg Val
530                 535                 540

Arg Gln Glu Arg Glu Lys His Phe Gln Arg Glu Glu Gln Glu Arg Leu
545                 550                 555                 560
```

```
Glu Arg Lys Lys Arg Leu Glu Glu Ile Met Lys Arg Thr Arg Arg Thr
                565                 570                 575
Glu Ala Thr Asp Lys Lys Thr Ser Asp Gln Arg Asn Gly Asp Ile Ala
            580                 585                 590
Lys Gly Ala Leu Thr Gly Gly Thr Glu Val Ser Ala Leu Pro Cys Thr
        595                 600                 605
Thr Asn Ala Pro Gly Asn Gly Lys Pro Val Gly Ser Pro His Val Val
    610                 615                 620
Thr Ser His Gln Ser Lys Val Thr Val Glu Ser Thr Pro Asp Leu Glu
625                 630                 635                 640
Lys Gln Pro Asn Glu Asn Gly Val Ser Val Gln Asn Glu Asn Phe Glu
                645                 650                 655
Glu Ile Ile Asn Leu Pro Ile Gly Ser Lys Pro Ser Arg Leu Asp Val
            660                 665                 670
Thr Asn Ser Glu Ser Pro Glu Ile Pro Leu Asn Pro Ile Leu Ala Phe
        675                 680                 685
Asp Asp Glu Gly Thr Leu Gly Pro Leu Pro Gln Val Asp Gly Val Gln
    690                 695                 700
Thr Gln Gln Thr Ala Glu Val Ile
705                 710

<210> SEQ ID NO 18
<211> LENGTH: 1285
<212> TYPE: PRT
<213> ORGANISM: Homo sapiens

<400> SEQUENCE: 18

Met Glu Asp Gly Lys Pro Val Trp Ala Pro His Pro Thr Asp Gly Phe
1               5                   10                  15
Gln Met Gly Asn Ile Val Asp Ile Gly Pro Asp Ser Leu Thr Ile Glu
                20                  25                  30
Pro Leu Asn Gln Lys Gly Lys Thr Phe Leu Ala Leu Ile Asn Gln Val
            35                  40                  45
Phe Pro Ala Glu Glu Asp Ser Lys Lys Asp Val Glu Asp Asn Cys Ser
        50                  55                  60
Leu Met Tyr Leu Asn Glu Ala Thr Leu Leu His Asn Ile Lys Val Arg
65                  70                  75                  80
Tyr Ser Lys Asp Arg Ile Tyr Thr Tyr Val Ala Asn Ile Leu Ile Ala
                85                  90                  95
Val Asn Pro Tyr Phe Asp Ile Pro Lys Ile Tyr Ser Ser Glu Ala Ile
                100                 105                 110
Lys Ser Tyr Gln Gly Lys Ser Leu Gly Thr Arg Pro Pro His Val Phe
            115                 120                 125
Ala Ile Ala Asp Lys Ala Phe Arg Asp Met Lys Val Leu Lys Met Ser
        130                 135                 140
Gln Ser Ile Ile Val Ser Gly Glu Ser Gly Ala Gly Lys Thr Glu Asn
145                 150                 155                 160
Thr Lys Phe Val Leu Arg Tyr Leu Thr Glu Ser Tyr Gly Thr Gly Gln
                165                 170                 175
Asp Ile Asp Asp Arg Ile Val Glu Ala Asn Pro Leu Leu Glu Ala Phe
            180                 185                 190
Gly Asn Ala Lys Thr Val Arg Asn Asn Asn Ser Ser Arg Phe Gly Lys
        195                 200                 205
Phe Val Glu Ile His Phe Asn Glu Lys Ser Ser Val Val Gly Gly Phe
    210                 215                 220
```

```
Val Ser His Tyr Leu Leu Glu Lys Ser Arg Ile Cys Val Gln Gly Lys
225                 230                 235                 240

Glu Glu Arg Asn Tyr His Ile Phe Tyr Arg Leu Cys Ala Gly Ala Ser
                245                 250                 255

Glu Asp Ile Arg Glu Lys Leu His Leu Ser Ser Pro Asp Asn Phe Arg
                260                 265                 270

Tyr Leu Asn Arg Gly Cys Thr Arg Tyr Phe Ala Asn Lys Glu Thr Asp
                275                 280                 285

Lys Gln Ile Leu Gln Asn Arg Lys Ser Pro Glu Tyr Leu Lys Ala Gly
290                 295                 300

Ser Met Lys Asp Pro Leu Leu Asp Asp His Gly Asp Phe Ile Arg Met
305                 310                 315                 320

Cys Thr Ala Met Lys Lys Ile Gly Leu Asp Asp Glu Glu Lys Leu Asp
                325                 330                 335

Leu Phe Arg Val Val Ala Gly Val Leu His Leu Gly Asn Ile Asp Phe
                340                 345                 350

Glu Glu Ala Gly Ser Thr Ser Gly Gly Cys Asn Leu Lys Asn Lys Ser
                355                 360                 365

Ala Gln Ser Leu Glu Tyr Cys Ala Glu Leu Leu Gly Leu Asp Gln Asp
370                 375                 380

Asp Leu Arg Val Ser Leu Thr Thr Arg Val Met Leu Thr Thr Ala Gly
385                 390                 395                 400

Gly Thr Lys Gly Thr Val Ile Lys Val Pro Leu Lys Val Glu Gln Ala
                405                 410                 415

Asn Asn Ala Arg Asp Ala Leu Ala Lys Thr Val Tyr Ser His Leu Phe
                420                 425                 430

Asp His Val Val Asn Arg Val Asn Gln Cys Phe Pro Phe Glu Thr Ser
                435                 440                 445

Ser Tyr Phe Ile Gly Val Leu Asp Ile Ala Gly Phe Glu Tyr Phe Glu
                450                 455                 460

His Asn Ser Phe Glu Gln Phe Cys Ile Asn Tyr Cys Asn Glu Lys Leu
465                 470                 475                 480

Gln Gln Phe Phe Asn Glu Arg Ile Leu Lys Glu Glu Gln Glu Leu Tyr
                485                 490                 495

Gln Lys Glu Gly Leu Gly Val Asn Glu Val His Tyr Val Asp Asn Gln
                500                 505                 510

Asp Cys Ile Asp Leu Ile Glu Ala Lys Leu Val Gly Ile Leu Asp Ile
                515                 520                 525

Leu Asp Glu Glu Asn Arg Leu Pro Gln Pro Ser Asp Gln His Phe Thr
530                 535                 540

Ser Ala Val His Gln Lys His Lys Asp His Phe Arg Leu Thr Ile Pro
545                 550                 555                 560

Arg Lys Ser Lys Leu Ala Val His Arg Asn Ile Arg Asp Asp Glu Gly
                565                 570                 575

Phe Ile Ile Arg His Phe Ala Gly Ala Val Cys Tyr Glu Thr Thr Gln
                580                 585                 590

Phe Val Glu Lys Asn Asn Asp Ala Leu His Met Ser Leu Glu Ser Leu
                595                 600                 605

Ile Cys Glu Ser Arg Asp Lys Phe Ile Arg Glu Leu Phe Glu Ser Ser
                610                 615                 620

Thr Asn Asn Asn Lys Asp Thr Lys Gln Lys Ala Gly Lys Leu Ser Phe
625                 630                 635                 640

Ile Ser Val Gly Asn Lys Phe Lys Thr Gln Leu Asn Leu Leu Leu Asp
```

-continued

```
                645                 650                 655
Lys Leu Arg Ser Thr Gly Ala Ser Phe Ile Arg Cys Ile Lys Pro Asn
            660                 665                 670

Leu Lys Met Thr Ser His His Phe Glu Gly Ala Gln Ile Leu Ser Gln
            675                 680                 685

Leu Gln Cys Ser Gly Met Val Ser Val Leu Asp Leu Met Gln Gly Gly
            690                 695                 700

Tyr Pro Ser Arg Ala Ser Phe His Glu Leu Tyr Asn Met Tyr Lys Lys
705                 710                 715                 720

Tyr Met Pro Asp Lys Leu Ala Arg Leu Asp Pro Arg Leu Phe Cys Lys
                725                 730                 735

Ala Leu Phe Lys Ala Leu Gly Leu Asn Glu Asn Asp Tyr Lys Phe Gly
            740                 745                 750

Leu Thr Lys Val Phe Phe Arg Pro Gly Lys Phe Ala Glu Phe Asp Gln
            755                 760                 765

Ile Met Lys Ser Asp Pro Asp His Leu Ala Glu Leu Val Lys Arg Val
            770                 775                 780

Asn His Trp Leu Thr Cys Ser Arg Trp Lys Lys Val Gln Trp Cys Ser
785                 790                 795                 800

Leu Ser Val Ile Lys Leu Lys Asn Lys Ile Lys Tyr Arg Ala Glu Ala
                805                 810                 815

Cys Ile Lys Met Gln Lys Thr Ile Arg Met Trp Leu Cys Lys Arg Arg
            820                 825                 830

His Lys Pro Arg Ile Asp Gly Leu Val Lys Val Gly Thr Leu Lys Lys
            835                 840                 845

Arg Leu Asp Lys Phe Asn Glu Val Val Ser Val Leu Lys Asp Gly Lys
            850                 855                 860

Pro Glu Met Asn Lys Gln Ile Lys Asn Leu Glu Ile Ser Ile Asp Thr
865                 870                 875                 880

Leu Met Ala Lys Ile Lys Ser Thr Met Met Thr Gln Glu Gln Ile Gln
                885                 890                 895

Lys Glu Tyr Asp Ala Leu Val Lys Ser Ser Glu Glu Leu Leu Ser Ala
            900                 905                 910

Leu Gln Lys Lys Lys Gln Gln Glu Glu Glu Ala Glu Arg Leu Arg Arg
            915                 920                 925

Ile Gln Glu Glu Met Glu Lys Glu Arg Lys Arg Glu Glu Asp Glu
            930                 935                 940

Lys Arg Arg Arg Lys Glu Glu Glu Arg Arg Met Lys Leu Glu Met
945                 950                 955                 960

Glu Ala Lys Arg Lys Gln Glu Glu Glu Arg Lys Lys Arg Glu Asp
                965                 970                 975

Asp Glu Lys Arg Ile Gln Ala Glu Val Glu Ala Gln Leu Ala Arg Gln
            980                 985                 990

Lys Glu Glu Glu Ser Gln Gln Gln Ala Val Leu Glu Gln Glu Arg Arg
            995                 1000                1005

Asp Arg Glu Leu Ala Leu Arg Ile Ala Gln Ser Glu Ala Glu Leu
            1010                1015                1020

Ile Ser Asp Glu Ala Gln Ala Asp Leu Ala Leu Arg Arg Asn Asp
            1025                1030                1035

Gly Thr Arg Pro Lys Met Thr Pro Glu Gln Met Ala Lys Glu Met
            1040                1045                1050

Ser Glu Phe Leu Ser Arg Gly Pro Ala Val Leu Ala Thr Lys Ala
            1055                1060                1065
```

```
Ala Ala Gly Thr Lys Lys Tyr Asp Leu Ser Lys Trp Lys Tyr Ala
    1070            1075                1080

Glu Leu Arg Asp Thr Ile Asn Thr Ser Cys Asp Ile Glu Leu Leu
    1085            1090                1095

Ala Ala Cys Arg Glu Glu Phe His Arg Arg Leu Lys Val Tyr His
    1100            1105                1110

Ala Trp Lys Ser Lys Asn Lys Arg Asn Thr Glu Thr Glu Gln
    1115            1120                1125

Arg Ala Pro Lys Ser Val Thr Asp Tyr Asp Phe Ala Pro Phe Leu
    1130            1135                1140

Asn Asn Ser Pro Gln Gln Asn Pro Ala Ala Gln Ile Pro Ala Arg
    1145            1150                1155

Gln Arg Glu Ile Glu Met Asn Arg Gln Gln Arg Phe Phe Arg Ile
    1160            1165                1170

Pro Phe Ile Arg Pro Ala Asp Gln Tyr Lys Asp Pro Gln Ser Lys
    1175            1180                1185

Lys Lys Gly Trp Trp Tyr Ala His Phe Asp Gly Pro Trp Ile Ala
    1190            1195                1200

Arg Gln Met Glu Leu His Pro Asp Lys Pro Pro Ile Leu Leu Val
    1205            1210                1215

Ala Gly Lys Asp Asp Met Glu Met Cys Glu Leu Asn Leu Glu Glu
    1220            1225                1230

Thr Gly Leu Thr Arg Lys Arg Gly Ala Glu Ile Leu Pro Arg Gln
    1235            1240                1245

Phe Glu Glu Ile Trp Glu Arg Cys Gly Gly Ile Gln Tyr Leu Gln
    1250            1255                1260

Asn Ala Ile Glu Ser Arg Gln Ala Arg Pro Thr Tyr Ala Thr Ala
    1265            1270                1275

Met Leu Gln Ser Leu Leu Lys
    1280            1285

<210> SEQ ID NO 19
<211> LENGTH: 320
<212> TYPE: PRT
<213> ORGANISM: Homo sapiens

<400> SEQUENCE: 19

Met Ser Ser Cys Asn Phe Thr His Ala Thr Phe Val Leu Ile Gly Ile
1               5                   10                  15

Pro Gly Leu Glu Lys Ala His Phe Trp Val Gly Phe Pro Leu Leu Ser
                20                  25                  30

Met Tyr Val Val Ala Met Phe Gly Asn Cys Ile Val Val Phe Ile Val
            35                  40                  45

Arg Thr Glu Arg Ser Leu His Ala Pro Met Tyr Leu Phe Leu Cys Met
        50                  55                  60

Leu Ala Ala Ile Asp Leu Ala Leu Ser Thr Ser Thr Met Pro Lys Ile
65                  70                  75                  80

Leu Ala Leu Phe Trp Phe Asp Ser Arg Glu Ile Ser Phe Glu Ala Cys
                85                  90                  95

Leu Thr Gln Met Phe Phe Ile His Ala Leu Ser Ala Ile Glu Ser Thr
            100                 105                 110

Ile Leu Leu Ala Met Ala Phe Asp Arg Tyr Val Ala Ile Cys His Pro
        115                 120                 125

Leu Arg His Ala Ala Val Leu Asn Asn Thr Val Thr Ala Gln Ile Gly
    130                 135                 140
```

```
Ile Val Ala Val Val Arg Gly Ser Leu Phe Phe Pro Leu Pro Leu
145                 150                 155                 160

Leu Ile Lys Arg Leu Ala Phe Cys His Ser Asn Val Leu Ser His Ser
            165                 170                 175

Tyr Cys Val His Gln Asp Val Met Lys Leu Ala Tyr Ala Asp Thr Leu
                180                 185                 190

Pro Asn Val Val Tyr Gly Leu Thr Ala Ile Leu Leu Val Met Gly Val
            195                 200                 205

Asp Val Met Phe Ile Ser Leu Ser Tyr Phe Leu Ile Ile Arg Thr Val
            210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
            245                 250                 255

Leu Ser Val Val His Arg Phe Gly Asn Ser Leu His Pro Ile Val Arg
            260                 265                 270

Val Val Met Gly Asp Ile Tyr Leu Leu Leu Pro Pro Val Ile Asn Pro
            275                 280                 285

Ile Ile Tyr Gly Ala Lys Thr Lys Gln Ile Arg Thr Arg Val Leu Ala
            290                 295                 300

Met Phe Lys Ile Ser Cys Asp Lys Asp Leu Gln Ala Val Gly Gly Lys
305                 310                 315                 320

<210> SEQ ID NO 20
<211> LENGTH: 425
<212> TYPE: PRT
<213> ORGANISM: Homo sapiens

<400> SEQUENCE: 20

Met Ala Thr Ala Glu Val Leu Asn Ile Gly Lys Lys Leu Tyr Glu Gly
1               5                   10                  15

Lys Thr Lys Glu Val Tyr Glu Leu Leu Asp Ser Pro Gly Lys Val Leu
            20                  25                  30

Leu Gln Ser Lys Asp Gln Ile Thr Ala Gly Asn Ala Ala Arg Lys Asn
        35                  40                  45

His Leu Glu Gly Lys Ala Ala Ile Ser Asn Lys Ile Thr Ser Cys Ile
    50                  55                  60

Phe Gln Leu Leu Gln Glu Ala Gly Ile Lys Thr Ala Phe Thr Arg Lys
65                  70                  75                  80

Cys Gly Glu Thr Ala Phe Ile Ala Pro Gln Cys Glu Met Ile Pro Ile
                85                  90                  95

Glu Trp Val Cys Arg Arg Ile Ala Thr Gly Ser Phe Leu Lys Arg Asn
            100                 105                 110

Pro Gly Val Lys Glu Gly Tyr Lys Phe Tyr Pro Pro Lys Val Glu Leu
        115                 120                 125

Phe Phe Lys Asp Asp Ala Asn Asn Asp Pro Gln Trp Ser Glu Glu Gln
    130                 135                 140

Leu Ile Ala Ala Lys Phe Cys Phe Ala Gly Leu Leu Ile Gly Gln Thr
145                 150                 155                 160

Glu Val Asp Ile Met Ser His Ala Thr Gln Ala Ile Phe Glu Ile Leu
                165                 170                 175

Glu Lys Ser Trp Leu Pro Gln Asn Cys Thr Leu Val Asp Met Lys Ile
            180                 185                 190

Glu Phe Gly Val Asp Val Thr Thr Lys Glu Ile Val Leu Ala Asp Val
        195                 200                 205
```

```
Ile Asp Asn Asp Ser Trp Arg Leu Trp Pro Ser Gly Asp Arg Ser Gln
    210                 215                 220

Gln Lys Asp Lys Gln Ser Tyr Arg Asp Leu Lys Glu Val Thr Pro Glu
225                 230                 235                 240

Gly Leu Gln Met Val Lys Lys Asn Phe Glu Trp Val Ala Glu Arg Val
                245                 250                 255

Glu Leu Leu Lys Ser Glu Ser Gln Cys Arg Val Val Leu Met
            260                 265                 270

Gly Ser Thr Ser Asp Leu Gly His Cys Glu Lys Ile Lys Lys Ala Cys
        275                 280                 285

Gly Asn Phe Gly Ile Pro Cys Glu Leu Arg Val Thr Ser Ala His Lys
    290                 295                 300

Gly Pro Asp Glu Thr Leu Arg Ile Lys Ala Glu Tyr Glu Gly Asp Gly
305                 310                 315                 320

Ile Pro Thr Val Phe Ala Val Ala Gly Arg Ser Asn Gly Leu Gly
                325                 330                 335

Pro Val Met Ser Gly Asn Thr Ala Tyr Pro Val Ile Ser Cys Pro Pro
                340                 345                 350

Leu Thr Pro Asp Trp Gly Val Gln Asp Val Trp Ser Ser Leu Arg Leu
            355                 360                 365

Pro Ser Gly Leu Gly Cys Ser Thr Val Leu Ser Pro Glu Gly Ser Ala
    370                 375                 380

Gln Phe Ala Ala Gln Ile Phe Gly Leu Ser Asn His Leu Val Trp Ser
385                 390                 395                 400

Lys Leu Arg Ala Ser Ile Leu Asn Thr Trp Ile Ser Leu Lys Gln Ala
                405                 410                 415

Asp Lys Lys Ile Arg Glu Cys Asn Leu
            420                 425

<210> SEQ ID NO 21
<211> LENGTH: 968
<212> TYPE: PRT
<213> ORGANISM: Homo sapiens

<400> SEQUENCE: 21

Met Pro Pro Arg Ala Pro Pro Ala Pro Gly Pro Arg Pro Pro Arg
1               5                   10                  15

Ala Ala Ala Ala Thr Asp Thr Ala Gly Ala Gly Gly Ala Gly Gly
                20                  25                  30

Ala Gly Gly Ala Gly Gly Pro Gly Phe Arg Pro Leu Ala Pro Arg Pro
        35                  40                  45

Trp Arg Trp Leu Leu Leu Leu Ala Leu Pro Ala Ala Cys Ser Ala Pro
50                  55                  60

Pro Pro Arg Pro Val Tyr Thr Asn His Trp Ala Val Gln Val Leu Gly
65                  70                  75                  80

Gly Pro Ala Glu Ala Asp Arg Val Ala Ala Ala His Gly Tyr Leu Asn
                85                  90                  95

Leu Gly Gln Gly Asn Leu Glu Asp Tyr Tyr His Phe Tyr His Ser Lys
                100                 105                 110

Thr Phe Lys Arg Ser Thr Leu Ser Ser Arg Gly Pro His Thr Phe Leu
            115                 120                 125

Arg Met Asp Pro Gln Val Lys Trp Leu Gln Gln Gln Glu Val Lys Arg
130                 135                 140

Arg Val Lys Arg Gln Val Arg Ser Asp Pro Gln Ala Leu Tyr Phe Asn
145                 150                 155                 160
```

-continued

```
Asp Pro Ile Trp Ser Asn Met Trp Tyr Leu His Cys Gly Asp Lys Asn
            165                 170                 175

Ser Arg Cys Arg Ser Glu Met Asn Val Gln Ala Ala Trp Lys Arg Gly
        180                 185                 190

Tyr Thr Gly Lys Asn Val Val Thr Ile Leu Asp Asp Gly Ile Glu
        195                 200                 205

Arg Asn His Pro Asp Leu Ala Pro Asn Tyr Asp Ser Tyr Ala Ser Tyr
        210                 215                 220

Asp Val Asn Gly Asn Asp Tyr Asp Pro Ser Pro Arg Tyr Asp Ala Ser
225                 230                 235                 240

Asn Glu Asn Lys His Gly Thr Arg Cys Ala Gly Glu Val Ala Ala Ser
                245                 250                 255

Ala Asn Asn Ser Tyr Cys Ile Val Gly Ile Ala Tyr Asn Ala Lys Ile
            260                 265                 270

Gly Gly Ile Arg Met Leu Asp Gly Asp Val Thr Asp Val Val Glu Ala
                275                 280                 285

Lys Ser Leu Gly Ile Arg Pro Asn Tyr Ile Asp Ile Tyr Ser Ala Ser
            290                 295                 300

Trp Gly Pro Asp Asp Gly Lys Thr Val Asp Gly Pro Gly Arg Leu
305                 310                 315                 320

Ala Lys Gln Ala Phe Glu Tyr Gly Ile Lys Lys Gly Arg Gln Gly Leu
                325                 330                 335

Gly Ser Ile Phe Val Trp Ala Ser Gly Asn Gly Gly Arg Glu Gly Asp
            340                 345                 350

Tyr Cys Ser Cys Asp Gly Tyr Thr Asn Ser Ile Tyr Thr Ile Ser Val
        355                 360                 365

Ser Ser Ala Thr Glu Asn Gly Tyr Lys Pro Trp Tyr Leu Glu Glu Cys
370                 375                 380

Ala Ser Thr Leu Ala Thr Thr Tyr Ser Ser Gly Ala Phe Tyr Glu Arg
385                 390                 395                 400

Lys Ile Val Thr Thr Asp Leu Arg Gln Arg Cys Thr Asp Gly His Thr
                405                 410                 415

Gly Thr Ser Val Ser Ala Pro Met Val Ala Gly Ile Ile Ala Leu Ala
            420                 425                 430

Leu Glu Ala Asn Ser Gln Leu Thr Trp Arg Asp Val Gln His Leu Leu
            435                 440                 445

Val Lys Thr Ser Arg Pro Ala His Leu Lys Ala Ser Asp Trp Lys Val
        450                 455                 460

Asn Gly Ala Gly His Lys Val Ser His Phe Tyr Gly Phe Gly Leu Val
465                 470                 475                 480

Asp Ala Glu Ala Leu Val Val Glu Ala Lys Lys Trp Thr Ala Val Pro
                485                 490                 495

Ser Gln His Met Cys Val Ala Ala Ser Asp Lys Arg Pro Arg Ser Ile
            500                 505                 510

Pro Leu Val Gln Val Leu Arg Thr Thr Ala Leu Thr Ser Ala Cys Ala
        515                 520                 525

Glu His Ser Asp Gln Arg Val Val Tyr Leu Glu His Val Val Val Arg
        530                 535                 540

Thr Ser Ile Ser His Pro Arg Arg Gly Asp Leu Gln Ile Tyr Leu Val
545                 550                 555                 560

Ser Pro Ser Gly Thr Lys Ser Gln Leu Leu Ala Lys Arg Leu Leu Asp
                565                 570                 575

Leu Ser Asn Glu Gly Phe Thr Asn Trp Glu Phe Met Thr Val His Cys
            580                 585                 590
```

Trp Gly Glu Lys Ala Glu Gly Gln Trp Thr Leu Glu Ile Gln Asp Leu
            595                 600                 605

Pro Ser Gln Val Arg Asn Pro Glu Lys Gln Gly Lys Leu Lys Glu Trp
        610                 615                 620

Ser Leu Ile Leu Tyr Gly Thr Ala Glu His Pro Tyr Thr Phe Ser
625                 630                 635                 640

Ala His Gln Ser Arg Ser Arg Met Leu Glu Leu Ser Ala Pro Glu Leu
                645                 650                 655

Glu Pro Pro Lys Ala Ala Leu Ser Pro Ser Gln Val Glu Val Pro Glu
            660                 665                 670

Asp Glu Glu Asp Tyr Thr Ala Gln Ser Thr Pro Gly Ser Ala Asn Ile
        675                 680                 685

Leu Gln Thr Ser Val Cys His Pro Glu Cys Gly Asp Lys Gly Cys Asp
    690                 695                 700

Gly Pro Asn Ala Asp Gln Cys Leu Asn Cys Val His Phe Ser Leu Gly
705                 710                 715                 720

Ser Val Lys Thr Ser Arg Lys Cys Val Ser Val Cys Pro Leu Gly Tyr
                725                 730                 735

Phe Gly Asp Thr Ala Ala Arg Arg Cys Arg Arg Cys His Lys Gly Cys
            740                 745                 750

Glu Thr Cys Ser Ser Arg Ala Ala Thr Gln Cys Leu Ser Cys Arg Arg
        755                 760                 765

Gly Phe Tyr His His Gln Glu Met Asn Thr Cys Val Thr Leu Cys Pro
    770                 775                 780

Ala Gly Phe Tyr Ala Asp Glu Ser Gln Lys Asn Cys Leu Lys Cys His
785                 790                 795                 800

Pro Ser Cys Lys Lys Cys Val Asp Glu Pro Glu Lys Cys Thr Val Cys
                805                 810                 815

Lys Glu Gly Phe Ser Leu Ala Arg Gly Ser Cys Ile Pro Asp Cys Glu
            820                 825                 830

Pro Gly Thr Tyr Phe Asp Ser Glu Leu Ile Arg Cys Gly Glu Cys His
        835                 840                 845

His Thr Cys Gly Thr Cys Val Gly Pro Gly Arg Glu Glu Cys Ile His
    850                 855                 860

Cys Ala Lys Asn Phe His Phe Asp Trp Lys Cys Val Pro Ala Cys
865                 870                 875                 880

Gly Glu Gly Phe Tyr Pro Glu Glu Met Pro Gly Leu Pro His Lys Val
                885                 890                 895

Cys Arg Arg Cys Asp Glu Asn Cys Leu Ser Cys Ala Gly Ser Ser Arg
            900                 905                 910

Asn Cys Ser Arg Cys Lys Thr Gly Phe Thr Gln Leu Gly Thr Ser Cys
        915                 920                 925

Ile Thr Asn His Thr Cys Ser Asn Ala Asp Glu Thr Phe Cys Glu Met
    930                 935                 940

Val Lys Ser Asn Arg Leu Cys Glu Arg Lys Leu Phe Ile Gln Phe Cys
945                 950                 955                 960

Cys Arg Thr Cys Leu Leu Ala Gly
                965

<210> SEQ ID NO 22
<211> LENGTH: 1536
<212> TYPE: DNA
<213> ORGANISM: Homo sapiens

<400> SEQUENCE: 22

```
cgagcacatg ggccgcgggc cgggcgggct cggggcgggcc gggacgagga ggggcgacga    60
cgagctgcga gcaaagatgt gccccgggac ccccggcacc ttccagtgga tttccttgcg   120
gaaaggatgt tggcggtccc tgtgacctgt ggagacacgg ccagatctgc cctccagcct   180
gatcttttgg ccagaaggag attaaaaaga tgcccctcaa gatggctgtg ctgtcagctg   240
catggagctt cgttcaagta ttttctgagc ctgatggatt tacagtgatg ttcagtggtc   300
tggggaataa cgctggtgga accatgcact ggaatgacac acgcccggca catttcagga   360
tactaaaagt ggttttaagg gaggctgtgg ctgaatgcct catggattct tacagcttgg   420
atgtccatgg gggacgaagg actgcagctg gctgagaggg ttgagatctc tgtttactta   480
gatctctgcc aacttccttt gggtctccct atggaatgta agaccccgac tcttcctggt   540
gaagcatctg atgcacgttc catccggcgc tcagctgggc ttgagctgac catactccct   600
ggagccttct cccgaggtgg gcgggtgacc ttggcacata cagccatcat gatggtactt   660
taagtggagg ctgaatcatc tccccttttga gctgctttgg gaacgtggcc cccttggtgt   720
tccccttttta ctgccaggac actgagattt ggagaggtaa gtggcttacc tgaggccatg   780
tgctaacaga gaagatgaag agatgattga acaggccta agaccagacc taagggtctg   840
tacatttttcc acatactttc catatcttta gaggcctgac caaagcagat cttttccttt   900
cttctaggta agtccaaagg cacctgcctg ctgggcccac tgttttctaa cttttcctaac   960
tttctgatcc cttggaggtg ataatcaaat attctagtct gaggcattgg gatacatggt  1020
gctaggttct gagactctgc gtcaggcctg aaccctgcat tttgtggagg tgggtgggag  1080
aatgttcccc tggggaacat gcctagacac ggggggacaac agttgccctc atggggaggt  1140
acctgtttac tcgctgttat gggaccgctt tcacaaaacc actgcaggtg agtgagttcc  1200
tgctgaatat caggcctggt gtctctagac tcattattcc cccacccaac ccctatgtta  1260
gttcatctcg agccacattt ttattgccat aatccaggcc tggacaggcc aagatctttt  1320
aacaatttta attactgaaa ataataactg catttttttt taaagcccaa ctttttggta  1380
agtcagccca aaatacagtc tttgtgttgc catctgggaa ctggatttgg aattgttctt  1440
ccatgagact gcagagcaga acggcagggc cagaggtccc acgagctggt cagacccggt  1500
tctgctcctt gctggctgag tgaccttggg cattgt                           1536
```

<210> SEQ ID NO 23  
<211> LENGTH: 167  
<212> TYPE: PRT  
<213> ORGANISM: Homo sapiens

<400> SEQUENCE: 23

```
Met Glu His Ile His Asp Ser Asp Gly Ser Ser Ser Ser His Gln
 1               5                  10                  15

Ser Leu Lys Ser Thr Ala Lys Trp Ala Ala Ser Leu Glu Asn Leu
                20                  25                  30

Glu Asp Pro Glu Gly Val Lys Arg Phe Arg Glu Phe Leu Lys Glu
                35                  40                  45

Phe Ser Glu Glu Asn Val Leu Phe Trp Leu Ala Cys Glu Asp Phe
    50                  55                  60

Lys Met Gln Asp Lys Thr Gln Met Gln Glu Lys Ala Lys Glu Ile Tyr
 65                  70                  75                  80

Met Thr Phe Leu Ser Ser Lys Ala Ser Ser Gln Val Asn Val Glu Gly
                    85                  90                  95

Gln Ser Arg Leu Asn Glu Lys Ile Leu Glu Glu Pro His Pro Leu Met
```

```
              100                 105                 110
Phe Gln Lys Leu Gln Asp Gln Ile Phe Asn Leu Met Lys Tyr Asp Ser
            115                 120                 125

Tyr Ser Arg Phe Leu Lys Ser Asp Leu Phe Leu Lys His Lys Arg Thr
        130                 135                 140

Glu Glu Glu Glu Glu Asp Leu Pro Asp Ala Gln Thr Ala Ala Lys Arg
145                 150                 155                 160

Ala Ser Arg Ile Tyr Asn Thr
            165

<210> SEQ ID NO 24
<211> LENGTH: 854
<212> TYPE: DNA
<213> ORGANISM: Homo sapiens
<220> FEATURE:
<221> NAME/KEY: modified_base
<222> LOCATION: (722)..(722)
<223> OTHER INFORMATION: a, c, t, g, unknown or other
<220> FEATURE:
<221> NAME/KEY: misc_feature
<222> LOCATION: (722)..(722)
<223> OTHER INFORMATION: n is a, c, g, or t
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: modified_base
<222> LOCATION: (822)..(822)
<223> OTHER INFORMATION: a, c, t, g, unknown or other
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: modified_base
<222> LOCATION: (840)..(840)
<223> OTHER INFORMATION: a, c, t, g, unknown or other
<220> FEATURE:
<221> NAME/KEY: misc_feature
<222> LOCATION: (840)..(840)
<223> OTHER INFORMATION: n is a, c, g, or t

<400> SEQUENCE: 24
ttttgtcacc ttttccctca ttagaaggaa agtagaaagc cttactttag gattttaaa       60 aaaaaaatcc atctcacccc atattggtct taaataagta tagactaatt aacctaagct     120
acctttaaca acgtagaatt tagatgggtt catatatgtg agaaaaacct gaatatagga     180
caggggtccc acttttttcc ccacctctgt cgcccaggct agagtatagt ggtgtgatct     240
tggcccactg caacctctgc ttcctaggtt caagtgattc tcctgcctca gcctcccaag     300
tagctgggat tgtaagagta tgccaccacg cccagctact ttttgtattt ttagtagaga     360
cagggtttca tcatgttggc caggatggtc tcttaactcc tgccctcaag tgatccacca     420
gagaggagat cctcggcctc cccaagtgct ggattatagg catgagccac cgtgcccagc     480
ctactttcta attaattaaa aaaaaaaaa aaaaaaaa aaaaaacttc ccaaatgagc       540
tgatagaaaa atgacgtgag gctgctttgc cttcaataat acctagtttt cagctgttcc     600
aactcgtttc caaatagaaa ttagctggaa cacactacag taatctcaag gaagggaaaa     660
ttaggcctta aaagatacca agaagtcagc atggtaccca attgaaacct ttgaccctta     720
gngggaattc attctatttg cactaaaagc cttaactgnt ggattcagag tccttttaac     780
```

```
tgggagttct atagaacttt acttttccc taggcccaga gnggagaagg gtttcttaan    840
agcggttcat ggga                                                     854
```

<210> SEQ ID NO 25
<211> LENGTH: 762
<212> TYPE: DNA
<213> ORGANISM: Homo sapiens
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: modified_base
<222> LOCATION: (587)..(587)
<223> OTHER INFORMATION: a, c, t, g, unknown or other
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: modified_base
<222> LOCATION: (599)..(599)
<223> OTHER INFORMATION: a, c, t, g, unknown or other
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: modified_base
<222> LOCATION: (602)..(602)
<223> OTHER INFORMATION: a, c, t, g, unknown or other
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: modified_base
<222> LOCATION: (611)..(611)
<223> OTHER INFORMATION: a, c, t, g, unknown or other
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: modified_base
<222> LOCATION: (711)..(711)
<223> OTHER INFORMATION: a, c, t, g, unknown or other
<220> FEATURE:
<221> NAME/KEY: misc_feature
<222> LOCATION: (711)..(711)
<223> OTHER INFORMATION: n is a, c, g, or t

<400> SEQUENCE: 25

```
ccgcgcttct tctgcttctt gctctcgtcg tccttgtcgc ggctgcgggt gctggtggtc     60
ggggtggagg agccggcgtc gctgtctcgc ttgcgcttcc gtgatgattt cttctgccgg   120
acctcctctt cgatctcctc cagcgtgccc tcctcgatgg ccttgagcca ctgcttctcc   180
gtcagtgagt cgctgtagtc cacctccttg cggtggcggg agccacggcc gaacatcttc   240
tcctcctcct cctcacaggt cagccgctcc acctccgcgt cgtccttgat gatccacgag   300
gggagctcgt cctcctccat gaggcgcggc ttccgcttgg ggttgcgggc ctcctcgcgc   360
ctgcggtcca ggtccatgcg catgaacaga tcaaactcct cctcgtgccg ggcgatcatc   420
tggttgacgg tctcgtcgtc gggcaccctcg tcttcctcct catcctgctc ctcgtgctcc   480
aggatggcct gcaggaaggc gcgccgctca tggctggagg acttctggtc gaacatgccg   540
gcctgnatca ccttctgggt cacgttgagc ttgtacttgg ctgcagncta gatcttctnc   600
```

```
tncacgctgt ntgcggtgca gaggcggagc acacgcacct cgttctgctg cccccgatgc    660
gtggggctcg tcctgcgctt gcaggtcctg gtgagggatc agtcgtgtca naatgatcac    720
agttctgccg acctgagtca gccgagcccc caacccgttg ct                       762
```

```
<210> SEQ ID NO 26
<211> LENGTH: 387
<212> TYPE: PRT
<213> ORGANISM: Homo sapiens

<400> SEQUENCE: 26
```

```
Met Ser Val Ala Phe Ala Ala Pro Arg Gln Arg Gly Lys Gly Glu Ile
1               5                   10                  15

Thr Pro Ala Ala Ile Gln Lys Met Leu Asp Asp Asn His Leu Ile
            20                  25                  30

Gln Cys Ile Met Asp Ser Gln Asn Lys Gly Lys Thr Ser Glu Cys Ser
        35                  40                  45

Gln Tyr Gln Gln Met Leu His Thr Asn Leu Val Tyr Leu Ala Thr Ile
    50                  55                  60

Ala Asp Ser Asn Gln Asn Met Gln Ser Leu Leu Pro Ala Pro Pro Thr
65                  70                  75                  80

Gln Asn Met Pro Met Gly Pro Gly Gly Met Asn Gln Ser Gly Pro Pro
                85                  90                  95

Pro Pro Pro Arg Ser His Asn Met Pro Ser Asp Gly Met Val Gly Gly
            100                 105                 110

Gly Pro Pro Ala Pro His Met Gln Asn Gln Met Asn Gly Gln Met Pro
        115                 120                 125

Gly Pro Asn His Met Pro Met Gln Pro Gly Pro Asn Gln Leu Asn
    130                 135                 140

Met Thr Asn Ser Ser Met Asn Met Pro Ser Ser Ser His Gly Ser Met
145                 150                 155                 160

Gly Gly Tyr Asn His Ser Val Pro Ser Ser Gln Ser Met Pro Val Gln
                165                 170                 175

Asn Gln Met Thr Met Ser Gln Gly Gln Pro Met Gly Asn Tyr Gly Pro
            180                 185                 190

Arg Pro Asn Met Ser Met Gln Pro Asn Gln Gly Pro Met Met His Gln
        195                 200                 205

Gln Pro Pro Ser Gln Gln Tyr Asn Met Pro Gln Gly Gly Gln His
    210                 215                 220

Tyr Gln Gly Gln Gln Pro Pro Met Gly Met Met Gly Gln Val Asn Gln
225                 230                 235                 240

Gly Asn His Met Met Gly Gln Arg Gln Ile Pro Pro Tyr Arg Pro Pro
                245                 250                 255

Gln Gln Gly Pro Pro Gln Gln Tyr Ser Gly Gln Glu Asp Tyr Tyr Gly
            260                 265                 270

Asp Gln Tyr Ser His Gly Gly Gln Gly Pro Glu Gly Met Asn Gln
        275                 280                 285

Gln Tyr Tyr Pro Asp Gly Asn Ser Gln Tyr Gly Gln Gln Asp Ala
    290                 295                 300

Tyr Gln Gly Pro Pro Gln Gln Gly Tyr Pro Gln Gln Gln
305                 310                 315                 320

Tyr Pro Gly Gln Gln Gly Tyr Pro Gly Gln Gln Gly Tyr Gly Pro
                325                 330                 335

Ser Gln Gly Gly Pro Gly Pro Gly Tyr Pro Asn Tyr Pro Gln Gly Gln
            340                 345                 350
```

```
Gly Gln Gln Tyr Gly Gly Tyr Arg Pro Thr Gln Pro Gly Pro Pro Gln
        355                 360                 365

Pro Pro Gln Gln Arg Pro Tyr Gly Tyr Asp Gln Gly Tyr Gly Asn
    370                 375                 380

Tyr Gln Gln
385

<210> SEQ ID NO 27
<211> LENGTH: 10
<212> TYPE: PRT
<213> ORGANISM: Homo sapiens

<400> SEQUENCE: 27

Tyr Gly Leu Pro Asp Val Asn Ile Leu Leu
1               5                   10

<210> SEQ ID NO 28
<211> LENGTH: 10
<212> TYPE: PRT
<213> ORGANISM: Homo sapiens

<400> SEQUENCE: 28

Gly Leu Pro Asp Val Asn Ile Leu Leu Phe
1               5                   10

<210> SEQ ID NO 29
<211> LENGTH: 11
<212> TYPE: PRT
<213> ORGANISM: Homo sapiens

<400> SEQUENCE: 29

Tyr Gly Leu Pro Asp Val Asn Ile Leu Leu Phe
1               5                   10

<210> SEQ ID NO 30
<211> LENGTH: 11
<212> TYPE: PRT
<213> ORGANISM: Homo sapiens

<400> SEQUENCE: 30

Glu Tyr Gly Leu Pro Asp Val Asn Ile Leu Leu
1               5                   10

<210> SEQ ID NO 31
<211> LENGTH: 11
<212> TYPE: PRT
<213> ORGANISM: Homo sapiens

<400> SEQUENCE: 31

Gly Leu Pro Asp Val Asn Ile Leu Leu Phe Gln
1               5                   10

<210> SEQ ID NO 32
<211> LENGTH: 13
<212> TYPE: PRT
<213> ORGANISM: Homo sapiens

<400> SEQUENCE: 32

Glu Tyr Gly Leu Pro Asp Val Asn Ile Leu Leu Phe Gln
1               5                   10

<210> SEQ ID NO 33
<211> LENGTH: 10
<212> TYPE: PRT
<213> ORGANISM: Homo sapiens
```

<400> SEQUENCE: 33

Ile Gln Leu Trp Gln Phe Leu Leu Glu Leu
1               5                   10

<210> SEQ ID NO 34
<211> LENGTH: 11
<212> TYPE: PRT
<213> ORGANISM: Homo sapiens

<400> SEQUENCE: 34

Gln Leu Trp Gln Phe Leu Leu Glu Leu Leu Ser
1               5                   10

<210> SEQ ID NO 35
<211> LENGTH: 12
<212> TYPE: PRT
<213> ORGANISM: Homo sapiens

<400> SEQUENCE: 35

Ile Gln Leu Trp Gln Phe Leu Leu Glu Leu Leu Ser
1               5                   10

<210> SEQ ID NO 36
<211> LENGTH: 11
<212> TYPE: PRT
<213> ORGANISM: Homo sapiens

<400> SEQUENCE: 36

Gln Ile Gln Leu Trp Gln Phe Leu Leu Glu Leu
1               5                   10

<210> SEQ ID NO 37
<211> LENGTH: 12
<212> TYPE: PRT
<213> ORGANISM: Homo sapiens

<400> SEQUENCE: 37

Gln Leu Trp Gln Phe Leu Leu Glu Leu Leu Ser Asp
1               5                   10

<210> SEQ ID NO 38
<211> LENGTH: 14
<212> TYPE: PRT
<213> ORGANISM: Homo sapiens

<400> SEQUENCE: 38

Gln Ile Gln Leu Trp Gln Phe Leu Leu Glu Leu Leu Ser Asp
1               5                   10

<210> SEQ ID NO 39
<211> LENGTH: 10
<212> TYPE: PRT
<213> ORGANISM: Homo sapiens

<400> SEQUENCE: 39

Asn Phe Val Ala Pro His Pro Pro Ala Leu
1               5                   10

<210> SEQ ID NO 40
<211> LENGTH: 10
<212> TYPE: PRT
<213> ORGANISM: Homo sapiens

<400> SEQUENCE: 40

```
Phe Val Ala Pro His Pro Pro Ala Leu Pro
1               5                   10

<210> SEQ ID NO 41
<211> LENGTH: 11
<212> TYPE: PRT
<213> ORGANISM: Homo sapiens

<400> SEQUENCE: 41

Asn Phe Val Ala Pro His Pro Pro Ala Leu Pro
1               5                   10

<210> SEQ ID NO 42
<211> LENGTH: 11
<212> TYPE: PRT
<213> ORGANISM: Homo sapiens

<400> SEQUENCE: 42

Met Asn Phe Val Ala Pro His Pro Pro Ala Leu
1               5                   10

<210> SEQ ID NO 43
<211> LENGTH: 11
<212> TYPE: PRT
<213> ORGANISM: Homo sapiens

<400> SEQUENCE: 43

Phe Val Ala Pro His Pro Pro Ala Leu Pro Val
1               5                   10

<210> SEQ ID NO 44
<211> LENGTH: 13
<212> TYPE: PRT
<213> ORGANISM: Homo sapiens

<400> SEQUENCE: 44

Met Asn Phe Val Ala Pro His Pro Pro Ala Leu Pro Val
1               5                   10

<210> SEQ ID NO 45
<211> LENGTH: 10
<212> TYPE: PRT
<213> ORGANISM: Homo sapiens

<400> SEQUENCE: 45

Gln Thr Leu Asp Gly Phe Val Phe Val Val
1               5                   10

<210> SEQ ID NO 46
<211> LENGTH: 10
<212> TYPE: PRT
<213> ORGANISM: Homo sapiens

<400> SEQUENCE: 46

Thr Leu Asp Gly Phe Val Phe Val Val Ala
1               5                   10

<210> SEQ ID NO 47
<211> LENGTH: 11
<212> TYPE: PRT
<213> ORGANISM: Homo sapiens

<400> SEQUENCE: 47

Gln Thr Leu Asp Gly Phe Val Phe Val Val Ala
1               5                   10
```

```
<210> SEQ ID NO 48
<211> LENGTH: 11
<212> TYPE: PRT
<213> ORGANISM: Homo sapiens

<400> SEQUENCE: 48

Leu Gln Thr Leu Asp Gly Phe Val Phe Val Val
1               5                   10

<210> SEQ ID NO 49
<211> LENGTH: 11
<212> TYPE: PRT
<213> ORGANISM: Homo sapiens

<400> SEQUENCE: 49

Thr Leu Asp Gly Phe Val Phe Val Val Ala Ser
1               5                   10

<210> SEQ ID NO 50
<211> LENGTH: 13
<212> TYPE: PRT
<213> ORGANISM: Homo sapiens

<400> SEQUENCE: 50

Leu Gln Thr Leu Asp Gly Phe Val Phe Val Val Ala Ser
1               5                   10

<210> SEQ ID NO 51
<211> LENGTH: 10
<212> TYPE: PRT
<213> ORGANISM: Homo sapiens

<400> SEQUENCE: 51

Cys Tyr Gln Ile Val Gly Leu Val Ala Val
1               5                   10

<210> SEQ ID NO 52
<211> LENGTH: 10
<212> TYPE: PRT
<213> ORGANISM: Homo sapiens

<400> SEQUENCE: 52

Tyr Gln Ile Val Gly Leu Val Ala Val Gly
1               5                   10

<210> SEQ ID NO 53
<211> LENGTH: 11
<212> TYPE: PRT
<213> ORGANISM: Homo sapiens

<400> SEQUENCE: 53

Cys Tyr Gln Ile Val Gly Leu Val Ala Val Gly
1               5                   10

<210> SEQ ID NO 54
<211> LENGTH: 11
<212> TYPE: PRT
<213> ORGANISM: Homo sapiens

<400> SEQUENCE: 54

Ser Cys Tyr Gln Ile Val Gly Leu Val Ala Val
1               5                   10

<210> SEQ ID NO 55
<211> LENGTH: 11
```

```
<212> TYPE: PRT
<213> ORGANISM: Homo sapiens

<400> SEQUENCE: 55

Tyr Gln Ile Val Gly Leu Val Ala Val Gly Gln
1               5                   10

<210> SEQ ID NO 56
<211> LENGTH: 13
<212> TYPE: PRT
<213> ORGANISM: Homo sapiens

<400> SEQUENCE: 56

Ser Cys Tyr Gln Ile Val Gly Leu Val Ala Val Gly Gln
1               5                   10

<210> SEQ ID NO 57
<211> LENGTH: 10
<212> TYPE: PRT
<213> ORGANISM: Homo sapiens

<400> SEQUENCE: 57

Ala Ser Leu Asp Leu Lys Leu Ile Phe Leu
1               5                   10

<210> SEQ ID NO 58
<211> LENGTH: 10
<212> TYPE: PRT
<213> ORGANISM: Homo sapiens

<400> SEQUENCE: 58

Ser Leu Asp Leu Lys Leu Ile Phe Leu Asp
1               5                   10

<210> SEQ ID NO 59
<211> LENGTH: 11
<212> TYPE: PRT
<213> ORGANISM: Homo sapiens

<400> SEQUENCE: 59

Ala Ser Leu Asp Leu Lys Leu Ile Phe Leu Asp
1               5                   10

<210> SEQ ID NO 60
<211> LENGTH: 11
<212> TYPE: PRT
<213> ORGANISM: Homo sapiens

<400> SEQUENCE: 60

Arg Ala Ser Leu Asp Leu Lys Leu Ile Phe Leu
1               5                   10

<210> SEQ ID NO 61
<211> LENGTH: 11
<212> TYPE: PRT
<213> ORGANISM: Homo sapiens

<400> SEQUENCE: 61

Ser Leu Asp Leu Lys Leu Ile Phe Leu Asp Ser
1               5                   10

<210> SEQ ID NO 62
<211> LENGTH: 13
<212> TYPE: PRT
<213> ORGANISM: Homo sapiens
```

-continued

```
<400> SEQUENCE: 62

Arg Ala Ser Leu Asp Leu Lys Leu Ile Phe Leu Asp Ser
1               5                   10

<210> SEQ ID NO 63
<211> LENGTH: 10
<212> TYPE: PRT
<213> ORGANISM: Homo sapiens

<400> SEQUENCE: 63

Leu Lys Leu Ile Phe Leu Asp Ser Arg Val
1               5                   10

<210> SEQ ID NO 64
<211> LENGTH: 10
<212> TYPE: PRT
<213> ORGANISM: Homo sapiens

<400> SEQUENCE: 64

Lys Leu Ile Phe Leu Asp Ser Arg Val Thr
1               5                   10

<210> SEQ ID NO 65
<211> LENGTH: 11
<212> TYPE: PRT
<213> ORGANISM: Homo sapiens

<400> SEQUENCE: 65

Leu Lys Leu Ile Phe Leu Asp Ser Arg Val Thr
1               5                   10

<210> SEQ ID NO 66
<211> LENGTH: 11
<212> TYPE: PRT
<213> ORGANISM: Homo sapiens

<400> SEQUENCE: 66

Asp Leu Lys Leu Ile Phe Leu Asp Ser Arg Val
1               5                   10

<210> SEQ ID NO 67
<211> LENGTH: 11
<212> TYPE: PRT
<213> ORGANISM: Homo sapiens

<400> SEQUENCE: 67

Lys Leu Ile Phe Leu Asp Ser Arg Val Thr Glu
1               5                   10

<210> SEQ ID NO 68
<211> LENGTH: 13
<212> TYPE: PRT
<213> ORGANISM: Homo sapiens

<400> SEQUENCE: 68

Asp Leu Lys Leu Ile Phe Leu Asp Ser Arg Val Thr Glu
1               5                   10

<210> SEQ ID NO 69
<211> LENGTH: 10
<212> TYPE: PRT
<213> ORGANISM: Homo sapiens

<400> SEQUENCE: 69

Ile Phe Leu Asp Ser Arg Val Thr Glu Val
```

```
                1               5                  10

<210> SEQ ID NO 70
<211> LENGTH: 10
<212> TYPE: PRT
<213> ORGANISM: Homo sapiens

<400> SEQUENCE: 70

Phe Leu Asp Ser Arg Val Thr Glu Val Thr
1               5                  10

<210> SEQ ID NO 71
<211> LENGTH: 11
<212> TYPE: PRT
<213> ORGANISM: Homo sapiens

<400> SEQUENCE: 71

Ile Phe Leu Asp Ser Arg Val Thr Glu Val Thr
1               5                  10

<210> SEQ ID NO 72
<211> LENGTH: 11
<212> TYPE: PRT
<213> ORGANISM: Homo sapiens

<400> SEQUENCE: 72

Leu Ile Phe Leu Asp Ser Arg Val Thr Glu Val
1               5                  10

<210> SEQ ID NO 73
<211> LENGTH: 11
<212> TYPE: PRT
<213> ORGANISM: Homo sapiens

<400> SEQUENCE: 73

Phe Leu Asp Ser Arg Val Thr Glu Val Thr Gly
1               5                  10

<210> SEQ ID NO 74
<211> LENGTH: 13
<212> TYPE: PRT
<213> ORGANISM: Homo sapiens

<400> SEQUENCE: 74

Leu Ile Phe Leu Asp Ser Arg Val Thr Glu Val Thr Gly
1               5                  10

<210> SEQ ID NO 75
<211> LENGTH: 9
<212> TYPE: PRT
<213> ORGANISM: Homo sapiens

<400> SEQUENCE: 75

Ala Leu Pro Asp Val Asn Ile Leu Leu
1               5

<210> SEQ ID NO 76
<211> LENGTH: 9
<212> TYPE: PRT
<213> ORGANISM: Homo sapiens

<400> SEQUENCE: 76

Gln Leu Trp Gln Phe Val Leu Glu Leu
1               5
```

```
<210> SEQ ID NO 77
<211> LENGTH: 9
<212> TYPE: PRT
<213> ORGANISM: Homo sapiens

<400> SEQUENCE: 77

Phe Val Ala Pro His Pro Pro Gly Leu
1               5

<210> SEQ ID NO 78
<211> LENGTH: 9
<212> TYPE: PRT
<213> ORGANISM: Homo sapiens

<400> SEQUENCE: 78

Thr Leu Asp Gly Phe Leu Phe Val Val
1               5

<210> SEQ ID NO 79
<211> LENGTH: 9
<212> TYPE: PRT
<213> ORGANISM: Homo sapiens

<400> SEQUENCE: 79

Tyr Gln Ile Val Ala Leu Val Ala Val
1               5

<210> SEQ ID NO 80
<211> LENGTH: 9
<212> TYPE: PRT
<213> ORGANISM: Homo sapiens

<400> SEQUENCE: 80

Ser Leu Asp Val Lys Leu Ile Phe Leu
1               5

<210> SEQ ID NO 81
<211> LENGTH: 9
<212> TYPE: PRT
<213> ORGANISM: Homo sapiens

<400> SEQUENCE: 81

Lys Leu Ile Tyr Leu Asp Ser Arg Val
1               5

<210> SEQ ID NO 82
<211> LENGTH: 9
<212> TYPE: PRT
<213> ORGANISM: Homo sapiens

<400> SEQUENCE: 82

Phe Leu Asp Thr Arg Val Thr Glu Val
1               5

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cttccctctg gactctcacg                                                20

<210> SEQ ID NO 84
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aggctgtgcc tagcagtgtt                                              20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgcaccacca actgcttagc                                              20

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggcatggact gtggtcatga g                                            21

<210> SEQ ID NO 87
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
aaagcaggct ccacc                                                   15

<210> SEQ ID NO 88
<211> LENGTH: 13
<212> TYPE: PRT
<213> ORGANISM: Hepatitis B virus

<400> SEQUENCE: 88

Thr Pro Pro Ala Tyr Arg Pro Pro Asn Ala Pro Ile Leu
1               5                   10
```

METHODS AND COMPOSITIONS FOR PROSTATE CANCER IMMUNOTHERAPY

CROSS-REFERENCE TO RELATED APPLICATIONS

This application is the U.S. National Stage filing under 35 U.S.C. §371 of international application PCT/US2009/042338, filed Apr. 30, 2009, which claims benefit of U.S. Provisional Application No. 61/126,065, filed May 1, 2008.

FIELD OF THE INVENTION

In general, the invention relates to methods and compositions for the treatment of cancer (e.g., prostate cancer).

BACKGROUND OF THE INVENTION

The failure of immunotherapy for the treatment of prostate cancer in clinical trials is partly due to the lack of a causative oncogene antigen target for such therapy. However, the identification of cancer-specific antigens, which are specifically expressed in targeted cancer cells, provides rational targets for cancer immunotherapy. For example, existing vaccines for prostate cancer utilize cell lines without discrete or identified antigens. In some instances, these vaccines include antigenic proteins that are not specific to targeted cancer cells, antigenic proteins that are not immunogenic, or antigenic proteins that are not expressed in sufficient amounts on the surface of the tumor cells, thus reducing the efficacy of these vaccines and potentially resulting in undesirable side effects. Therefore, there is a need in the art for effective, more specific immunotherapies for the treatment of cancer, such as prostate cancer.

SUMMARY OF THE INVENTION

The present invention features methods and compositions (e.g., immune response stimulating peptides (e.g., ERG or SIM2 peptides), activated immune cells, antigen-presenting cells, and antibodies or antigen-binding fragments thereof) for generating an immune response for the treatment of cancer (e.g., prostate cancer).

In a first aspect, the invention features an immune response stimulating peptide having at least 90% sequence identity (e.g., 95, 96, 97, 98, or 99% sequence identity) to a contiguous amino acid sequence set forth in SEQ ID NO:1 (ERG2), SEQ ID NO:5 (SIM2), SEQ ID NO:11 (AMACR), SEQ ID NO:12 (BICD1), SEQ ID NO:13 (C10orf137), SEQ ID NO:14 (CDCL6), SEQ ID NO:15 (ICA1), SEQ ID NO:16 (KIAA1661), SEQ ID NO:17 (MAP7), SEQ ID NO:18 (MYO6), SEQ ID NO:19 (OR51E2), SEQ ID NO:20 (PAICS), SEQ ID NO:21 (PCSK6), SEQ ID NO:22 (PVT1), SEQ ID NO:23 (RGS10), SEQ ID NO:24 (SGEF), SEQ ID NO:25 (SMARCA4///MRPL43), or SEQ ID NO:26 (SS18), wherein the peptide has at least 7 but fewer than 50 amino acid residues (e.g., between 7 and 30, 25, 20, 15, 14, 13, 12, 11, or 10 amino acid residues, preferably 8, 9, or 10 amino acid residues, most preferably 9 amino acid residues) and is capable of activating immune cells in a mammalian host when bound to an antigen-presenting molecule. In another embodiment, the immune response stimulating peptide has the amino acid sequence set forth in SEQ ID NOs: 2, 3, 4, 6, 7, 8, 9, or 10.

In a second aspect, the invention features an activated immune cell (e.g., a cytotoxic T lymphocyte) capable of specifically binding to an immune response stimulating peptide of the first aspect of the invention when the peptide is bound to an antigen-presenting molecule.

In a third aspect, the invention features an antigen-presenting cell having on its surface a peptide of the first aspect of the invention that is bound to an antigen-presenting molecule of an antigen-presenting cell.

In a fourth aspect, the invention features an antibody or antigen-binding fragment thereof that specifically binds to a peptide of the first aspect of the invention when the peptide is bound to an antigen-presenting molecule.

In a fifth aspect, the invention features a method of treating cancer (e.g., prostate cancer) in a subject (e.g., a mammal, such as a human) by administering a composition containing a peptide, activated immune cell, antigen-presenting cell, or antibody or antigen-binding fragment thereof of the first, second, third, and fourth aspects of the invention, respectively, in an amount sufficient to treat the cancer. The method may include administering an adjuvant, cytokine, or hormone therapy (e.g., androgen ablation). The composition administered to the subject (e.g., a human) may include a pharmaceutically acceptable diluent, excipient, or carrier and may be administered by any means known in the art (e.g., injection).

In a sixth aspect, the invention features a method of diagnosing a subject (e.g., a mammal, such as a human) as having cancer (e.g., prostate cancer) by measuring the level of ERG (e.g., SEQ ID NOs: 1, 2, 3, or 4) or SIM2 polypeptide (e.g., SEQ ID NOs: 5, 6, 7, 8, 9, or 10), or fragment thereof, in a sample from the subject and comparing it to a reference, wherein an alteration (e.g., an increase) in the level of ERG or SIM2 polypeptide compared to a reference is a diagnostic indicator of cancer (e.g., prostate cancer). The sample may be a bodily fluid (e.g., urine, blood, serum, plasma, and cerebrospinal fluid), cell, or tissue sample from a subject in which ERG or SIM2 polypeptide is normally detectable.

In other embodiments of all aspects of the invention, the immune cells of the invention include, for example, T cells (e.g., cytotoxic T lymphocytes); the antigen-presenting molecules are, e.g., histocompatibility molecules (e.g., HLA molecules (e.g., HLA class I molecules)) that may be present on the surface of a cell, e.g., a prostate cancer cell. Antigen-presenting cells contemplated by the invention include, e.g., dendritic cells, macrophages, B cells, monocytes, fibroblasts, thymic epithelial cells, thyroid epithelial cells, glial cells, pancreatic beta cells, and vascular endothelial cells. Any of the agents described by the invention (e.g., immune response stimulating peptides, activated immune cells, antigen-presenting cells, and antibodies or antigen-binding fragments thereof) may be conjugated to a heterologous compound, e.g., a therapeutic agent or cytotoxic agent. In yet other embodiments, the compositions of the invention may be administered as a vaccine and may include, for example, an additional therapeutic agent (e.g., a chemotherapeutic agent) or an adjuvant.

As used herein, "activation of immune cells" is meant an increase in immune cell (e.g., T cells (e.g., cytotoxic T lymphocytes), B cells, macrophages, and NK cells) function, for example, the release of cytokines, antibodies, and/or the induction of apoptosis following stimulation with one or more stimulatory molecules.

By "adjuvant" is meant any substance that is used to specifically or non-specifically potentiate an antigen-specific immune response through, e.g., activation of antigen-presenting cells. Exemplary adjuvants include an oil emulsion (e.g., complete or incomplete Freund's adjuvant), a chemokine, a cytokine, or an ADP-ribosylating exotoxin (bARE)). An adjuvant may be administered with an antigen or may be administered by itself. A single molecule may have both adjuvant and antigen properties.

As used herein, by "administering" is meant a method of giving a dosage of a composition of the invention to a subject in need thereof. The compositions described herein can be administered by any acceptable route known in the art and including, e.g., parenteral, dermal, transdermal, ocular, inhalation, buccal, sublingual, perilingual, nasal, rectal, topical, and oral administration. Parenteral administration includes intra-arterial, intravenous, intraperitoneal, subcutaneous, and intramuscular administration. The preferred method of administration can vary depending on various factors (e.g., the components of the composition being administered, the condition being treated and its severity, and the age, weight, and health of the patient).

By "an amount sufficient to treat" is meant the amount of a composition of the invention administered to improve, inhibit, or ameliorate a condition of a subject, or a symptom thereof, in a clinically relevant manner (e.g., improve, inhibit, prevent, or ameliorate prostate cancer or symptoms thereof). Any improvement in the subject is considered sufficient to achieve treatment. Preferably, an amount sufficient to treat is an amount that reduces, inhibits, or prevents the occurrence of one or more symptoms of, e.g., cancer (e.g., prostate cancer) or is an amount that reduces the severity of, or the length of time during which a subject suffers from, one or more symptoms of the cancer (e.g., by at least 10%, 20%, or 30%, more preferably by at least 50%, 60%, or 70%, and most preferably by at least 80%, 90%, 95%, 99%, or more, relative to a control subject that is not treated with a composition of the invention). A sufficient amount of a composition used to practice the methods described herein varies depending upon the manner of administration and the age, body weight, and general health of the subject being treated. A physician or researcher can decide the appropriate amount and dosage regimen.

The term "antibody," as used herein, includes whole antibodies or immunoglobulins and any antigen-binding fragment or single chains thereof. Antibodies, as used herein, can be mammalian (e.g., human or mouse), humanized, chimeric, recombinant, synthetically produced, or naturally isolated. Antibodies of the present invention include all known forms of antibodies and other protein scaffolds with antibody-like properties. For example, the antibody can be a human antibody, a humanized antibody, a bispecific antibody, a chimeric antibody, or a protein scaffold with antibody-like properties, such as fibronectin or ankyrin repeats. The antibody also can be a Fab, Fab'2, scFv, SMIP, diabody, nanobody, aptamers, or a domain antibody. The antibody can have any of the following isotypes: IgG (e.g., IgG1, IgG2, IgG3, and IgG4), IgM, IgA (e.g., IgA1, IgA2, and IgAsec), IgD, or IgE.

The term "antigen-binding fragment," as used herein, refers to one or more fragments of an antibody that retain the ability to specifically bind to a cancer-specific antigen (e.g., a prostate cancer-specific antigen (e.g., ERG or SIM2)). The antigen-binding function of an antibody can be performed by fragments of a full-length antibody. Examples of binding fragments encompassed within the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., Nature 341:544-546 (1989)), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science 242: 423-426 (1988) and Huston et al., Proc. Natl. Acad. Sci. USA 85: 5879-5883 (1988)). These antibody fragments are obtained using conventional techniques known to those of skill in the art, and the fragments are screened for utility in the same manner as intact antibodies. Antigen-binding fragments can be produced by recombinant DNA techniques or by enzymatic or chemical cleavage of intact immunoglobulins.

By "antigen-presenting cell" is meant a cell that displays an antigen (e.g., a cancer-specific antigen, such as a prostate cancer-specific antigen) complexed with a major histocompatibility complex (MHC) molecule on its surface. In some embodiments, antigen-presenting cells are capable of activating an immune cell (e.g., a T cell) that has not been exposed to an antigen (e.g., a naive T cell). These antigen-presenting cells internalize the antigen (e.g., either by phagocytosis or by receptor-mediated endocytosis) and display a fragment of the antigen bound to an MHC molecule on the cell surface. The immune cell (e.g., T cell) recognizes and interacts with the MHC molecule complex on the surface of the antigen-presenting cell. An additional co-stimulatory signal is then produced by the antigen-presenting cell, leading to activation of the T cell. Antigen-presenting cells include, e.g., dendritic cells, macrophages, B cells, monocytes, fibroblasts, thymic epithelial cells, thyroid epithelial cells, glial cells, pancreatic beta cells, and vascular endothelial cells. Antigen-presenting cells may be isolated from any of a variety of biological fluids, tissues, and organs (e.g., peripheral blood, bone marrow, tumor-infiltrating cells, peritumoral tissues, infiltrating cells, lymph nodes, spleen, skin, and umbilical cord blood).

As used herein, an "antigen-presenting molecule" refers to a class I or class II major histocompatibility (MHC) molecule (e.g., a human leukocyte antigen (HLA) molecule) or any other molecule capable of binding to an antigen and presenting the antigen on the surface of a cell such that it can be recognized by an immune cell (e.g., a naïve T cell) as a complex of antigen and antigen-presenting molecule, thereby leading to, e.g., activation of the immune cell.

The term "cytotoxic agent," as used herein, refers to a substance that inhibits or prevents one or more functions of cells (e.g., cellular replication, division, or secretion of proteins) or causes apoptosis or necrosis of cells. The term is intended to include radioactive isotopes (e.g., $I^{131}$, $I^{125}$, $Y^{90}$, and $Re^{186}$), chemotherapeutic agents, and toxins, such as enzymatically active toxins of bacterial, fungal, plant or animal origin, or fragments thereof. Additional cytotoxic agents include, but are not limited to, alkylating agents, antibiotics, antimetabolites, tubulin inhibitors, topoisomerase I and II inhibitors, hormonal agonists or antagonists, or immunomodulators. Cytotoxic agents may be cytotoxic when activated by light or infrared radiation (Photofrin, IR dyes; Nat. Biotechnol. 19(4):327-331, 2001), may operate through other mechanistic pathways, or be supplementary potentiating agents.

The term "immune cells," as used herein, refers to any cell that is involved in the generation, regulation, or effect of the acquired or innate immune system. Immune cells include, e.g., T cells (e.g., CD4+ cells or CD8+ cells), B cells, natural killer (NK) cells, macrophages, monocytes and dendritic cells, and neutrophils.

By "immune response stimulating peptide" is meant a peptide that is a tumor-specific antigen, such as a prostate cancer-specific antigen (e.g., a peptide of ERG or SIM2) that is presented by an antigen-presenting cell histocompatibility molecule (e.g., a major histocompatibility complex molecule (MHC), such as an HLA class I molecule) expressed in, e.g., dendritic cells, macrophages, monocytes, and B cells; the binding of a naïve immune cell (e.g., a T cell) to the peptide/histocompatibility molecule complex activates an immune cell against the tumor-specific antigen. Such immune response stimulating peptides generally comprise at least 7 amino acid residues, but may comprise up to 50 amino acid residues. Immune response stimulating peptides can generally be identified using well-known techniques including, e.g., screening peptides for the ability to react with antigen-specific antibodies, antisera, or T cell lines or clones. T cell responses to the immune response stimulating peptide may include, e.g., the release of cytokines, increased T cell proliferation, or changes in intracellular calcium concentrations, as known in the art.

By "pharmaceutically acceptable carrier" is meant a diluent, excipient, or adjuvant which is physiologically acceptable to the subject while retaining the therapeutic properties of the composition with which it is administered. One exemplary pharmaceutically acceptable carrier is physiological saline. Other physiologically acceptable diluents, excipients, carriers, or adjuvants and their formulations are known to one skilled in the art.

By "proliferative disease" or "cancer" is meant any condition characterized by abnormal or unregulated cell growth. An example of a proliferative disease is, e.g., prostate cancer. Other exemplary cancers include solid tumors such as: sarcomas (e.g., clear cell sarcoma), carcinomas (e.g., renal cell carcinoma), and lymphomas; tumors of the breast, colon, rectum, lung, oropharynx, hypopharynx, esophagus, stomach, pancreas, liver, bilecyst, bile duct, small intestine, urinary system (including the kidney, bladder, and epithelium of the urinary tract), female genital system (including the uterine neck, uterus, ovary, chorioma, and gestational trophoblast), male genital system (including the seminal vesicle and testicles), endocrine glands (including the thyroid gland, adrenal gland, and pituitary body), skin (including angioma, melanoma, sarcoma originating from bone or soft tissue, and Kaposi's sarcoma), brain and meninges (including astrocytoma, neuroastrocytoma, spongioblastoma, retinoblastoma, neuroma, neuroblastoma, neurinoma and neuroblastoma), nerves, eyes, hem opoietic system (including chloroleukemia, plasmacytoma and dermal T lymphoma/leukemia), and immune system (including lymphoma, e.g., Hodgkin's lymphoma and non-Hodgkin's lymphoma). An example of a non-solid tumor proliferative disease is leukemia (e.g., acute lymphoblastic leukemia).

By "protein," "polypeptide," or "peptide" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated polypeptide or peptide," "substantially pure polypeptide or peptide," or "substantially pure and isolated polypeptide or peptide" is typically considered removed from cellular constituents and substantially pure when it is at least 60% by weight free from the proteins and naturally occurring organic molecules with which it is naturally associated. Preferably, the polypeptide or peptide is at least 75%, more preferably at least 90%, and most preferably at least 99% by weight pure. A substantially pure polypeptide or peptide may be obtained by standard techniques, for example, by extraction from a natural source (e.g., cell lines), by expression of a recombinant nucleic acid encoding the polypeptide, or by chemically synthesizing the polypeptide or peptide. Purity can be measured by any appropriate method, e.g., by column chromatography, polyacrylamide gel electrophoresis, or HPLC analysis. Alternatively, a polypeptide or peptide is considered isolated if it has been altered by human intervention, placed in a location that is not its natural site, or if it is introduced into one or more cells.

By "specifically bind" is meant the preferential association of a binding moiety (e.g., an antibody, histocompatibility molecule, antigen-binding fragment, receptor, ligand, small molecule, or a cell (e.g., an immune cell)) to a target molecule (e.g., an antigen (or fragment thereof), cytokine, chemokine, hormone, receptor, antigen/MHC complex, or ligand) or to a cell or tissue bearing the target molecule (e.g., a cell surface antigen, a receptor, and a ligand) and not to non-target cells or tissues lacking the target molecule. In the context of an antigen/MHC complex, the term "specifically bind" applies, e.g., to the preferential association between the antigen/MHC complex and a receptor (e.g., a T cell receptor) on a naïve immune cell, such as a T cell. It is recognized that a certain degree of non-specific interaction may occur between a binding moiety and a non-target molecule (present alone or in combination with a cell or tissue). Nevertheless, specific binding may be distinguished as mediated through specific recognition of the target molecule or complex. Specific binding results in a much stronger association between the binding moiety (e.g., an antibody or antigen-binding fragment) and, e.g., cells bearing the target molecule (e.g., an antigen or antigen/MHC complex) than between the binding moiety (e.g., an antibody or immune cell) and, e.g., cells lacking the target molecule. Specific binding typically results in greater than 2-fold, preferably greater than 5-fold, more preferably greater than 10-fold and most preferably greater than 100-fold increase in the amount of bound binding moiety (per unit time) to, e.g., a cell or tissue bearing the target molecule as compared to a cell or tissue lacking that target molecule. Binding moieties bind to the target molecule with a dissociation constant of, e.g., less than $10^{-6}$ M, more preferably less than $10^{-7}$ M, $10^{-8}$ M, $10^{-9}$ M, $10^{-10}$ M, $10^{-11}$ M, or $10^{-12}$ M, and most preferably less than $10^{-13}$ M, $10^{14}$ M, or $10^{-15}$ M. Specific binding to a target molecule, e.g., a protein or peptide (e.g., an antigen) under such conditions requires a binding moiety that is selected for its specificity for that particular target molecule. A variety of assay formats are appropriate for selecting binding moieties (e.g., antibodies or immune cells) capable of specifically binding to a particular target molecule (e.g., an antigen or antigen/MHC complex), and vice versa. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York, 1988, for a description of immunoassay formats and conditions that can be used to determine specific immunoreactivity.

By "subject" is meant any animal, e.g., a mammal (e.g., a human). A subject to be treated according to the methods described herein (e.g., a subject diagnosed with cancer (e.g., prostate cancer)) may be one who has been diagnosed by a medical practitioner as having such a condition or one at risk for developing the condition (e.g., cancer (e.g., prostate cancer)). Diagnosis may be performed by any suitable means. One skilled in the art will understand that a subject to be treated according to the present invention may have been subjected to standard tests or may have been identified, without examination, as one at high risk due to the presence of one or more risk factors (e.g., elevated prostate specific antigen (PSA) or a history of cancer).

The term "substantial identity" or "substantially identical," when used in the context of comparing a polynucleotide or polypeptide sequence to a reference sequence, means that the polynucleotide or polypeptide sequence is the same as the reference sequence or has a specified percentage of nucleotides or amino acid residues that are the same at the corresponding locations within the reference sequence when the two sequences are optimally aligned. For instance, an amino acid sequence that is "substantially identical" to a reference sequence has at least about 60% identity, preferably 65%, 70%, 75%, 80%, 85%, 90%, 91%, 92%, 93%, 94%, 95%, 96%, 97%, 98%, 99%, or higher percentage identity (up to 100%) to the reference sequence (e.g., the full-length amino acid sequence of ERG or SIM2 as set forth in SEQ ID NOs:11 or 12, respectively, or a fragment thereof), when compared and aligned for maximum correspondence over the full length of the reference sequence as measured using BLAST or BLAST 2.0 sequence comparison algorithms with default parameters, or by manual alignment and visual inspection (see, e.g., NCBI website).

The term "vaccine," as used herein, is defined as a composition used to provoke an immune response and confer immunity, at least briefly, after administration of the composition to a subject.

Other features and advantages of the invention will be apparent from the detailed description and from the claims.

BRIEF DESCRIPTION OF THE DRAWINGS

FIG. 4A is a schematic representation of NAPPA. FIG. 4B shows microarray data of autoantibodies to ACPP, AMACR, BRD2, ERG, and ETV1 by screening one prostate cancer serum against 800 tumor-associated antigens (TAAs).

FIGS. 9A and 9B describe sorted naïve CD4 and CD8 T cells from splenocytes of TRAMP and control mice cultured with anti-CD3 and anti-CD28 Abs in the presence of TGF-β. The percentage of newly differentiated Tregs was determined by flow cytometry after three days of culture. FIGS. 9C and 9D show that treatment with an agonist anti-Tim-1 antibody at the time of immunization enhances the CTL response to Tag antigen in B6 mice, as evidenced by an increased number of Tag-specific CTLs.

FIG. 11 is the AMACR amino acid sequence (SEQ ID NO:11).

FIG. 12 is the BICD1 amino acid sequence (SEQ ID NO:12).

FIG. 13 is the C10orf137 amino acid sequence (SEQ ID NO:13).

FIG. 14 is the CDC2L6 amino acid sequence (SEQ ID NO:14).

FIG. 15 is the ICA1 amino acid sequence (SEQ ID NO:15).

FIG. 16 is the KIAA1661 amino acid sequence (SEQ ID NO:16).

FIG. 17 is the MAP7 amino acid sequence (SEQ ID NO:17).

FIG. 18 is the MYO6 amino acid sequence (SEQ ID NO:18).

FIG. 19 is the OR51E2 amino acid sequence (SEQ ID NO:19).

FIG. 20 is the PAICS amino acid sequence (SEQ ID NO:20).

FIG. 21 is the PCSK6 amino acid sequence (SEQ ID NO:21).

FIG. 22 is the PVT1 nucleic acid sequence (SEQ ID NO:22).

FIG. 23 is the RGS10 amino acid sequence (SEQ ID NO:23).

FIG. 24 is the SGEF amino acid sequence (SEQ ID NO:24).

FIG. 25 is the SMARCA4///MRPL43 nucleic acid sequence (SEQ ID NO:25).

FIG. 26 is the SS18 amino acid sequence (SEQ ID NO:26).

FIG. 27 is the ERG amino acid sequence (SEQ ID NO:1).

FIG. 28 is the SIM2 amino acid sequence (SEQ ID NO:5).

DETAILED DESCRIPTION

Figure 1:
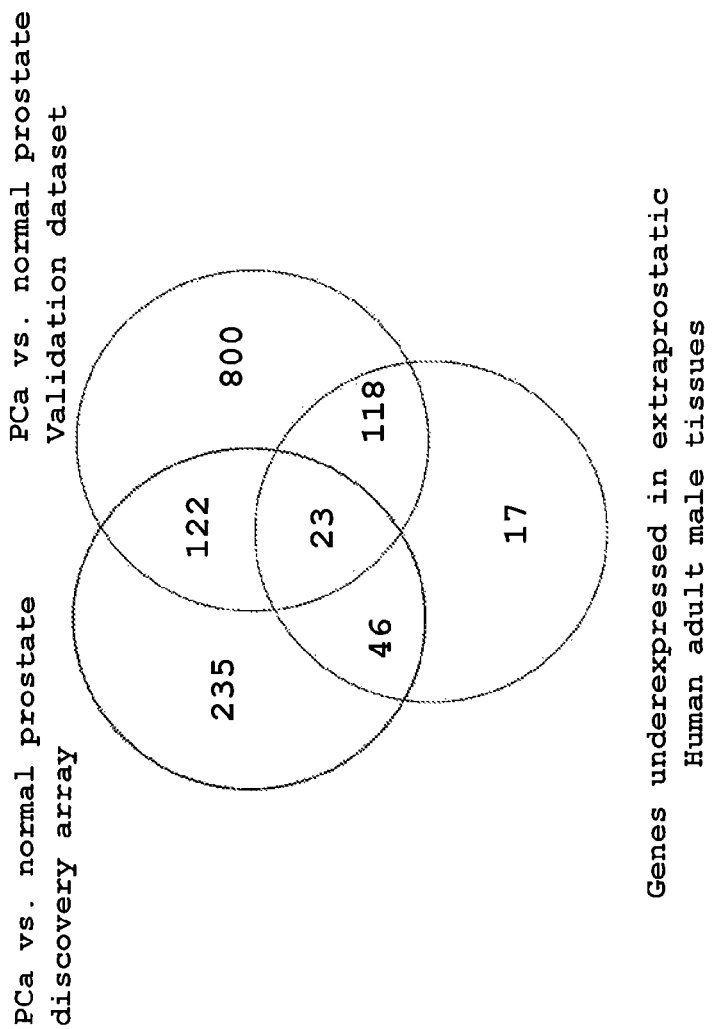
FIG. 1 is a Venn diagram highlighting the genes overexpressed in prostate cancer in our data set and in the Stanford data set and those underexpressed in extraprostatic human adult male tissues as deduced from the Novartis Gene Expression Atlas.

It was recently discovered that the ERG transcription factor is overexpressed in prostate cancer cells and not expressed in non-cancerous prostate cells. We hypothesized that, because normal tissues do not express ERG, immune tolerance to ERG could be overcome and that immune responses could be generated against ERG. We identified ERG-derived, immune response stimulating peptides that can be presented to human immune cells (e.g., naïve T cells) via, e.g., the human HLA-A2.1 antigen-presenting molecule that is found on the surface of all cells in the majority of humans. In addition, we identified immune response stimulating peptides from the protein SIM2, another protein overexpressed in prostate cancer cells and not expressed in non-cancerous prostate cells that may serve as an immunotherapy against prostate cancer. Our studies have also identified 16 additional proteins overexpressed in prostate cancer cells, peptides of which can also be used in immunotherapy.

Accordingly, the present invention features methods and compositions (e.g., immune response stimulating peptides (e.g., ERG or SIM2 peptides), activated immune cells, antigen-presenting cells, and antibodies or antigen-binding fragments thereof) for generating an immune response for the treatment of cancer (e.g., prostate cancer).

ERG, SIM2, and Other Prostate Tumor-Associated Antigens

An immune response stimulating peptide that is a tumor-specific antigen, such as a prostate cancer-specific antigen (e.g., a peptide of ERG or SIM2) that is presented by an antigen-presenting cell histocompatibility molecule (e.g., a major histocompatibility complex molecule (MHC), such as HLA class I) expressed in, e.g., dendritic cells, macrophages, monocytes, and B cells; the binding of a naïve immune cell (e.g., a T cell) to the peptide/histocompatibility molecule complex activates an immune cell against the tumor-specific antigen. Such immune response stimulating peptides generally contain at least 7 amino acid residues but fewer than 50 amino acid residues. For example, the immune response stimulating peptide may include, e.g., 7, 8, 9, 10, 11, 12, 13, 14, 15, 16, 17, 18, 19, 20, 25, 30, 35, 40, 45, or 49 amino acid residues. Non-limiting examples of immune response stimulating peptides for use in the treatment of prostate cancer are described in Table 1.

TABLE 1

| Peptide Name | Peptide Sequence |
|---|---|
| ERG(157) (SEQ ID NO: 2) | GLPDVNILL |
| ERG(295) (SEQ ID NO: 3) | QLWQFLLEL |
| ERG(412) (SEQ ID NO: 4) | FVAPHPPAL |
| SIM2(87) (SEQ ID NO: 6) | TLDGFVFVV |
| SIM2(205) (SEQ ID NO: 7) | YQIVGLVAV |
| SIM2(237) (SEQ ID NO: 8) | SLDLKLIFL |
| SIM2(241) (SEQ ID NO: 9) | KLIFLDSRV |
| SIM2(244) (SEQ ID NO: 10) | FLDSRVTEV |
| SEQ ID NO: 27 | YGLPDVNILL |
| SEQ ID NO: 28 | GLPDVNILLF |
| SEQ ID NO: 29 | YGLPDVNILLF |
| SEQ ID NO: 30 | EYGLPDVNILL |
| SEQ ID NO: 31 | GLPDVNILLFQ |
| SEQ ID NO: 32 | EYGLPDVNILLFQ |
| SEQ ID NO: 33 | IQLWQFLLEL |
| SEQ ID NO: 34 | QLWQFLLELLS |
| SEQ ID NO: 35 | IQLWQFLLELLS |
| SEQ ID NO: 36 | QIQLWQFLLEL |
| SEQ ID NO: 37 | QLWQFLLELLSD |
| SEQ ID NO: 38 | QIQLWQFLLELLSD |
| SEQ ID NO: 39 | NFVAPHPPAL |
| SEQ ID NO: 40 | FVAPHPPALP |
| SEQ ID NO: 41 | NFVAPHPPALP |
| SEQ ID NO: 42 | MNFVAPHPPAL |
| SEQ ID NO: 43 | FVAPHPPALPV |
| SEQ ID NO: 44 | MNFVAPHPPALPV |
| SEQ ID NO: 45 | QTLDGFVFVV |
| SEQ ID NO: 46 | TLDGFVFVVA |
| SEQ ID NO: 47 | QTLDGFVFVVA |
| SEQ ID NO: 48 | LQTLDGFVFVV |
| SEQ ID NO: 49 | TLDGFVFVVAS |
| SEQ ID NO: 50 | LQTLDGFVFVVAS |
| SEQ ID NO: 51 | CYQIVGLVAV |
| SEQ ID NO: 52 | YQIVGLVAVG |
| SEQ ID NO: 53 | CYQIVGLVAVG |
| SEQ ID NO: 54 | SCYQIVGLVAV |
| SEQ ID NO: 55 | YQIVGLVAVGQ |
| SEQ ID NO: 56 | SCYQIVGLVAVGQ |
| SEQ ID NO: 57 | ASLDLKLIFL |

TABLE 1-continued

| Peptide Name | Peptide Sequence |
| --- | --- |
| SEQ ID NO: 58 | SLDLKLIFLD |
| SEQ ID NO: 59 | ASLDLKLIFLD |
| SEQ ID NO: 60 | RASLDLKLIFL |
| SEQ ID NO: 61 | SLDLKLIFLDS |
| SEQ ID NO: 62 | RASLDLKLIFLDS |
| SEQ ID NO: 63 | LKLIFLDSRV |
| SEQ ID NO: 64 | KLIFLDSRVT |
| SEQ ID NO: 65 | LKLIFLDSRVT |
| SEQ ID NO: 66 | DLKLIFLDSRV |
| SEQ ID NO: 67 | KLIFLDSRVTE |
| SEQ ID NO: 68 | DLKLIFLDSRVTE |
| SEQ ID NO: 69 | IFLDSRVTEV |
| SEQ ID NO: 70 | FLDSRVTEVT |
| SEQ ID NO: 71 | IFLDSRVTEVT |
| SEQ ID NO: 72 | LIFLDSRVTEV |
| SEQ ID NO: 73 | FLDSRVTEVTG |
| SEQ ID NO: 74 | LIFLDSRVTEVTG |
| SEQ ID NO: 75 | ALPDVNILL |
| SEQ ID NO: 76 | QLWQFVLEL |
| SEQ ID NO: 77 | FVAPHPPGL |
| SEQ ID NO: 78 | TLDGFLFVV |
| SEQ ID NO: 79 | YQIVALVAV |
| SEQ ID NO: 80 | SLDVKLIFL |
| SEQ ID NO: 81 | KLIYLDSRV |
| SEQ ID NO: 82 | FLDTRVTEV |

Immune response stimulating peptides may be identified using well-known techniques, such as those described in Paul, W. E. (ed.), Fundamental Immunology, 3rd ed., pages 243-247 (Raven Press, 1993), hereby incorporated by reference. Such techniques include, e.g., screening polypeptides for the ability to react with antigen-specific antibodies, antisera, MHC molecules (e.g., HLA class I molecules), and/or T cell lines or clones. T cell responses to the immune response stimulating peptide may include, e.g., the release of cytokines, increased T cell proliferation, or changes in intracellular calcium concentrations, as known in the art. Activated T cells can now target cells expressing the peptide and can cause apoptosis or necrosis due to, e.g., changes in cytokine expression.

Immune response stimulating peptides, as described herein, can be produced by chemical synthesis using, for example, Merrifield solid phase synthesis, solution phase synthesis, or a combination of both (see, for example, the methods described in *Solid Phase Peptide Synthesis*, 2nd ed., 1984, The Pierce Chemical Co., Rockford, Ill., hereby incorporated by reference). Immune response stimulating peptides may then be condensed by standard peptide assembly chemistry. The peptides of the present invention may also be obtained by biological or genetic engineering processes (e.g., recombinant production in bacteria, mammalian cells, such as CHO cells, or in transgenic animals). For example, an expression vector, known to one of skill in the art, may be used that includes a polynucleotide sequence encoding the peptide of interest; the expression vector can be incorporated into a cell and the peptide encoded thereby can be expressed in the cell.

Peptides having the desired activity may be modified as necessary to provide certain desired attributes, e.g., improved pharmacological characteristics, while increasing or at least retaining substantially all of the biological activity of the unmodified peptide to bind the desired antigen-presenting molecule and activate the appropriate immune cell. For example, the immune response stimulating peptides may be subject to various changes, such as, e.g., substitutions (either conservative or non-conservative), deletions, or insertions, wherein such changes might provide for certain advantages in their use (e.g., improved binding to antigen-presenting molecules). Conservative substitutions may include, e.g., replacing an amino acid residue with another residue that is biologically and/or chemically similar (e.g., one hydrophobic residue for another or one polar residue for another). The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well-known peptide synthesis procedures, as described in, e.g., Merrifield, *Science* 232: 341-347 (1986), Barany and Merrifield, The Peptides, Gross and Meienhofer, eds., 1979, pages 1-284, Academic Press, New York.

The immune response stimulating peptides may also be modified by lengthening or shortening the amino acid sequence of the peptide, e.g., by the addition or deletion of amino acids. The peptides may also be modified by altering the order or composition of certain residues, though certain amino acid residues essential for biological activity, e.g., those at critical contact sites or conserved residues, may generally not be altered without an adverse effect on biological activity. The non-critical amino acids need not be limited to those naturally occurring in proteins, such as L-α-amino acids (or their D-isomers), but may include non-natural amino acids as well, such as β-γ-δ-amino acids, as well as many derivatives of L-α-amino acids.

Modifications of the immune response stimulating peptides with various amino acid residue mimetics or unnatural amino acids are particularly useful in increasing the stability of the peptide in vivo.

The immune response stimulating peptides of the present invention may be modified to provide desired attributes other than improved half-life in vivo. For example, the ability of the peptides to induce immune cell (e.g., cytotoxic T lymphocyte) activity may be enhanced by linkage to a sequence that contains at least one epitope that is capable of inducing, e.g., a T helper cell response. Exemplary epitopes include the non-structural protein from influenzae virus, NS1 (hemaglutinin) and the tetanus toxoid. Alternatively, the epitope can be selected so as to increase the solubility of the peptide or to enable the peptide to be targeted to desired intracellular compartments. The peptide may also be conjugated to any known cytotoxic or therapeutic moiety known to treat, inhibit, reduce, or ameliorate disease (e.g., prostate cancer)

In one embodiment, the immune response stimulating peptides of the invention activate immune cells in a subject when bound to an antigen-presenting molecule. An antigen-presenting molecule is a class I or class II major histocompatibility (MHC) molecule (e.g., a human leukocyte antigen (HLA) molecule) or any other molecule capable of binding to an antigen that presents the antigen on the surface of a cell and is recognized by cell(s) of the immune system as a complex of antigen and antigen-presenting molecule. Exemplary HLA molecules include, without limitation, HLA-A 1 (A*0101); HLA-A2 (A*0206); HLA-A2 (A*0201); HLA-A2 (A*0207); HLA-A2 (A*02011); HLA-A3 (A*0301); HLA-A11 (A*11011); HLA-A24 (A*24021); HLA-A24 (A*2420); HLA-A26 (A*2601); HLA-A26 (A*2603); HLA-A31 (A*31012); HLA-A33 (A*3303); HLA-B7 (B*07021); HLA-B8 (B*0801); HLA-B15 (B*15011); HLA-B35 (B*35011); HLA-B38 (B*3801); HLA-B39 (B*39011); HLA-B40 (B*40012); HLA-B40 (B*4002); HLA-B44 (B*4401); HLA-B44 (B*44031); HLA-B46 (B*4601); HLA-B48 (B*4801); HLA-B51 (B*51011); HLA-B52 (B*52011); HLA-B54 (B*5401); HLA-B55 (B*5502); HLA-B59 (B*5901); HLA-Cw1 (Cw*0102); HLA-Cw1 (Cw*0103); HLA-Cw3 (Cw*03031); HLA-Cw3 (Cw*03041); HLA-Cw4 (Cw*04011); HLA-Cw6 (Cw*0602); HLA-Cw7 (Cw*0702); HLA-Cw8 (Cw*0801); HLA-Cw12 (Cw*12022); HLA-Cw14 (Cw*14021); HLA-Cw14 (Cw*1403); HLA-Cw15 (Cw*15021); HLA-Cx 52 (Cw 12) (Cw*1201); HLA-Cx52 (Cw12) (Cw*1201). Human Class II HLA alleles include, without limitation, HLA-DA alpha 1-4 (pDA alpha 1-4); HLA-DA alpha 1-5 (pDA alpha 1-5); HLA-DA beta 5 (pDA beta 5); HLA-DC alpha 107 (pDC alpha 107); HLA-DO alpha 20 (pDO alpha 20); HLA-DQ beta155 (pDQ beta155); HLA-DR alpha 11 (pDR alpha 11); HLA-DR beta 134 (pDR beta 134); HLA DR beta 5 (TOK H5 DR beta); HLA-DR beta 4 (YT158); HLA-DQA1 (pgDQ4A); HLA-DQB1 (pg DQ1B); HLA-DQB1 (pg DQ1BS); HLA-DRA (DRA2EH); HLA-DPA1 (DPA 02022); HLA-DPB1 (DPB0202); HLA-DRB1 (K b DRB10803); HLA-DRB1 (K b DRB11201); HLA-DRB1 (K b DRB11302); HLA-DRB3 (DRB30301 EMJ-4); HLA-DQA1 (DQA10501 AMALA-4); HLA-DQB1 (DQB10301 AMALA-4); HLA-DQA1 (DQA10101 KAS1163-6); and HLA-DQB1 (DQB10503 EK2-4).

Activated Immune Cells

The present invention features activated immune cells capable of specifically binding to an immune response stimulating peptide when the peptide is bound to an antigen-presenting molecule (e.g., an MHC molecule (e.g., an HLA class I molecule)). In one embodiment, activated immune cells (e.g., cytotoxic T cells) may be generated in vitro according to the methods described in, e.g., U.S. Pat. No. 6,130,087, hereby incorporated by reference. Immune cells (e.g., T cells) may be, e.g., cultured with the antigen presenting cells (e.g., dendritic cells, macrophages, monocytes, and B cells) that present the immune response stimulating peptide in complex with a histocompatibility molecule, thereby activating the immune cells such that the activated immune cells now target cells presenting the immune response stimulating peptide on its surface in a complex with a histocompatibility molecule (e.g., an HLA class I molecule). Other methods for activating immune cells are described in U.S. Pat. Nos. 5,928,643, 6,074,635, and 6,210,873, hereby incorporated by reference.

Antigen-Presenting Cells

The present invention features an antigen-presenting cell that includes, on its surface, a complex between an antigen-presenting molecule and any one of the immune response stimulating peptides described herein. Antigen-presenting cells may be prepared, e.g., by contacting a cell having antigen-presenting ability (e.g., dendritic cells, macrophages, B cells, monocytes, fibroblasts, thymic epithelial cells, thyroid epithelial cells, glial cells, pancreatic beta cells, or vascular endothelial cells) with any one of the immune response stimulating peptides described herein. Such cells may be isolated from any of a variety of biological fluids, tissues, and organs (e.g., peripheral blood, bone marrow, tumor-infiltrating cells, peritumoral tissues, infiltrating cells, lymph nodes, spleen, skin, or umbilical cord blood).

Methods for preparing antigen-presenting cells are described in, e.g., U.S. Pat. No. 6,787,164, hereby incorporated by reference. Briefly, antigen-presenting cells may be engineered using gene transfer techniques (e.g., by the insertion of one or more recombinant or synthetic nucleic acid sequences encoding the immune response stimulating peptide) such that the peptides are expressed in effective amounts in the recipient host cell. By "effective amount" is meant that expression is sufficient to enable the recipient cell to provoke the desired immune response in vivo. For gene transfer into the cells to express the selected molecules, the nucleic acid may be directly introduced ex vivo in the form of "naked" nucleic acid, e.g. by microinjection, electroporation, as calcium-phosphate-DNA gels, with DEAE dextran, or in encapsulated form (e.g. in vesicles such as liposomes), or in a suitable viral vector. Expression of recombinant genes of interest after introduction into the antigen-presenting cells is confirmed by, e.g., immunoassays or biological assays for functional activity of the protein product. For example, expression of introduced molecules into cells may be confirmed by detecting the binding of labeled antibodies (specific for the immune response stimulating peptide and) to the antigen-presenting cells using assays such as, e.g., FACS or ELISA. Biological activity of the engineered cells can be verified, for example, in in vitro assays and in animal models (e.g., mice or non-human primates) prior to testing in humans. The ability of the engineered cells of the invention to function as desired, e.g. to process and present antigens for activating an immune response, may be tested using in vitro or in vivo assays. Immune cell activation (e.g., T cell activation) may be detected by various known methods, including measuring changes in the proliferation of immune cells, killing of target cells, and secretion of certain regulatory factors (e.g., lymphokines), expression of mRNA of certain immunoregulatory molecules, or a combination of these events.

As an alternative to gene transfer, the immune response stimulating peptides described herein may be added to antigen-presenting cells in culture and "loaded" on the antigen-presenting cell for presentation of the molecules to, e.g., T cells (see, e.g., Tykocinski et al., *Amer. J. Pathol.* 148: 1-16, 1996, hereby incorporated by reference). Peptide or protein pulsing (e.g., co-culturing) may also be used (Inaba et al., *J. Exp. Med.* 172: 631-640, 1990). Alternatively, peptides may be introduced to cell surfaces via fusion with liposomes bearing the selected immune response stimulating peptides (Coeshott et al., *J. Immunol.* 134: 1343-1348, 1985).

The antigen-presenting cells may be suspended in any known physiologically compatible pharmaceutical carrier such as cell culture medium, physiological saline, or phosphate-buffered saline to form a physiologically acceptable, aqueous pharmaceutical composition. Parenteral vehicles include, e.g., sodium chloride solution, Ringer's dextrose, dextrose and sodium chloride, or lactated Ringer's. The antigen-presenting cells may be introduced into the subject to be treated by using one of a number of methods of administration. For example, the antigen presenting cells may be inoculated (with or without adjuvant) parenterally (including, for example, intravenous, intra-arterial, intraperitoneal, intramuscular, intradermal, and subcutaneous), by ingestion, or applied to mucosal surfaces. Alternatively, the antigen-presenting cells of the invention may be administered locally by direct injection into, e.g., a cancerous lesion or infected tissue.

The antigen-presenting cells of the invention are introduced in at least one dose into a subject in need thereof (e.g., a prostate cancer patient), with sufficient numbers of antigen-presenting cells to activate immune cells of the immune system and induce an immune response, e.g., against the cancer antigen. The cells may be administered in a single infusion containing at least, e.g., $10^6$ to $10^{12}$ cells, or in multiple sequential infusions containing the same number of cells.

Antibodies or Antigen-Binding Fragments

Antibodies or antigen-binding fragments of the invention include, e.g., the IgG, IgA, IgM, IgD, and IgE isotypes. Antibodies or antibody fragments of the invention, as used herein, contain one or more complementarily determining regions (CDR) or binding peptides that bind to target proteins (e.g., a tumor-specific protein, such as a prostate tumor specific protein (e.g., ERG and SIM2) or an immune response stimulating peptide). In some embodiments, the antibodies or antigen-binding fragments specifically bind to an immune response stimulating peptide when the peptide is bound to an antigen-presenting molecule (e.g., an HLA class I molecule).

Many of the antibodies, or fragments thereof, described herein can undergo non-critical amino-acid substitutions, additions or deletions in both the variable and constant regions without loss of binding specificity or effector functions, or intolerable reduction of binding affinity (e.g., below about $10^{-7}$ M). Usually, an antibody or antibody fragment incorporating such alterations exhibits substantial sequence identity to a reference antibody or antibody fragment from which it is derived. Occasionally, a mutated antibody or antibody fragment can be selected having the same specificity and increased affinity compared with a reference antibody or antibody fragment from which it was derived. Phage-display technology offers powerful techniques for selecting such antibodies. See, e.g., Dower et al., WO 91/17271 McCafferty et al., WO 92/01047; and Huse, WO 92/06204, hereby incorporated by reference.

Antibody fragments include separate variable heavy chains, variable light chains, Fab, Fab', F(ab')$_2$, Fabc, and scFv. Fragments can be produced by enzymatic or chemical separation of intact immunoglobulins. For example, a F(ab')$_2$ fragment can be obtained from an IgG molecule by proteolytic digestion with pepsin at pH 3.0-3.5 using standard methods such as those described in Harlow and Lane, Antibodies: A Laboratory Manual, Cold Spring Harbor Pubs., New York, 1988. Fab fragments may be obtained from F(ab')$_2$ fragments by limited reduction, or from whole antibody by digestion with papain in the presence of reducing agents. Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

Methods of preparing chimeric and humanized antibodies and antibody fragments are described in, e.g., U.S. Pat. Nos. 4,816,567; 5,530,101; 5,622,701; 5,800,815; 5,874,540; 5,914,110; 5,928,904; 6,210,670; 6,677,436; and 7,067,313 and U.S. Patent Application Nos. 2002/0031508; 2004/0265311; and 2005/0226876. Preparation of antibody or antigen-binding fragments thereof is further described in, e.g., U.S. Pat. Nos. 6,331,415; 6,818,216; and 7,067,313.

Adjuvants

Suitable adjuvants for compositions of the present invention comprise those adjuvants that are capable of enhancing an immune response to the peptides (e.g., immune response stimulating peptides (e.g., ERG or SIM2 peptides)), antibodies or antigen-binding fragments thereof, activated immune cells, and antigen-presenting cells of the present invention. Adjuvants are well known in the art (see, e.g., *Vaccine Design—The Subunit and Adjuvant Approach*, 1995, Pharmaceutical Biotechnology, Volume 6, Eds. Powell and Newman, Plenum Press, New York and London, hereby incorporated by reference).

Preferred adjuvants for use in the compositions of the present invention include aluminum or calcium salts (e.g., hydroxide or phosphate salts). A desirable adjuvant is an aluminum hydroxide gel such as Alhydrogel™. For aluminum hydroxide gels (alum), the peptides (e.g., immune response stimulating peptides (e.g., ERG or SIM2 peptides)), antibodies or antigen-binding fragments thereof, activated immune cells, and antigen-presenting cells are admixed with the adjuvant so that between 50 to 800 µg of aluminum are present per dose, and preferably, between 400 and 600 µg are present.

Another adjuvant for use in the compositions of the present invention is an emulsion. An emulsion can be an oil-in-water emulsion or a water-in-oil emulsion. In addition to the peptides, antibodies or antigen-binding fragments thereof, activated immune cells, and antigen-presenting cells, such emulsions comprise an oil phase of, e.g., squalene or squalane and a dispersing agent. Non-ionic dispersing agents (e.g., mono- and di-$C_{12}$-$C_{24}$-fatty acid esters of sorbitan and mannide, such as sorbitan mono-stearate, sorbitan mono-oleate, and mannide mono-oleate) may also be used.

Water-in-oil emulsions may include squalene and mannide mono-oleate (Arlacel™ A), optionally with squalane, emulsified in the composition of the invention. Well-known examples of such emulsions include Montanide™ ISA-720 and Montanide™ ISA-703 (Seppic, Castres, France), each of which is understood to contain both squalene and squalane, with squalene predominating in each, but to a lesser extent in Montanide™ ISA-703. Montanide™ ISA-720 may also be used with an oil-to-water ratio of 7:3 (w/w). Other oil-in-water emulsion adjuvants include those disclosed in WO 95/17210 and EP 0399842, hereby incorporated by reference.

The use of small molecule adjuvants is also contemplated herein. Small molecule adjuvants include 7-substituted-8-oxo- or 8-sulfo-guanosine derivatives (e.g., 7-allyl-8-oxoguanosine (loxoribine)), described in U.S. Pat. Nos. 4,539,205; 4,643,992; 5,011,828; and 5,093,318; herein incorporated by reference.

Additional adjuvants include monophosphoryl lipid A (MPL) (available from Corixa Corp. (see, U.S. Pat. No. 4,987,237)), CPG available from Coley Pharmaceutical Group, QS21 (available from Aquila Biopharmaceuticals, Inc.), SBAS2 (available from SmithKline Beecham), muramyl dipeptide analogues described in U.S. Pat. No. 4,767,842, and MF59 (available from Chiron Corp. (see, U.S. Pat. Nos. 5,709,879 and 6,086,901)). Other adjuvants include the active saponin fractions derived from the bark of the South American tree *Quillaja Saponaria Molina* (e.g., Quil™ A). Derivatives of Quil™ A, for example QS21 (an HPLC purified fraction derivative of Quil™ A), and the method of its production are disclosed in U.S. Pat. No. 5,057,540. In addition to QS21 (known as QA21), other fractions such as QA17 are also disclosed.

3-De-O-acylated monophosphoryl lipid A is a well-known adjuvant manufactured by Ribi Immunochem. The adjuvant contains three components extracted from bacteria: monophosphoryl lipid (MPL) A, trehalose dimycolate (TDM), and cell wall skeleton (CWS) in a 2% squalene/Tween™ 80 emulsion. This adjuvant can be prepared by the methods taught in GB 2122204B. A preferred form of 3-de-O-acylated monophosphoryl lipid A is in the form of an emulsion having a small particle size of less than 0.2 μm in diameter (EP 0689454 B1).

The muramyl dipeptide adjuvants include N-acetyl-muramyl-L-threonyl-D-isoglutamine (thr-MDP; U.S. Pat. No. 4,606,918), N-acetyl-nor-muramyl-L-alanyl-D-isoglutamine (CGP 11637, referred to as nor-MDP), and N-acteryl-muramyl-L-alanyl-D-isoglutaminyl-L-alanine-2-(1',2'-dipalmitoyl-sn-glycero-3-hydroxyphosphoryloxy)-ethylamin (CGP) 1983A, referred to as MTP-PE.

Adjuvant mixtures include, e.g., combinations of 3D-MPL and QS21 (see, e.g., EP0671948 B1), oil-in-water emulsions including 3D-MPL and QS21 (see, e.g., WO 95/17210 and PCT/EP98/05714), 3D-MPL formulated with other carriers (see, e.g., EP 0689454 B1), QS21 formulated in cholesterol-containing liposomes (see, e.g., WO 96/33739), or immunostimulatory oligonucleotides (see, e.g., WO 96/02555). Alternative adjuvants include those described in, e.g., WO 99/52549 and non-particulate suspensions of polyoxyethylene ether (see, e.g., UK Patent Application No. 9807805.8).

Adjuvants are utilized in various amounts, which can vary with the adjuvant, subject, and the components of the composition (e.g., compositions including peptides (e.g., immune response stimulating peptides (e.g., ERG or SIM2 peptides), antibodies or antigen-binding fragments thereof, activated immune cells, and antigen-presenting cells) being administered. Typical amounts can vary from about 1 μg to about 50 mg per dosage. Those skilled in the art know that appropriate concentrations or amounts can be readily determined.

Conjugation to Cytotoxic and Other Therapeutic Agents

The agents of the invention (e.g., immune response stimulating peptides and antibodies to these peptides or antigen-binding fragments thereof) may be coupled to or administered with any known cytotoxic or therapeutic moiety to form an agent or composition of the invention, respectively, that can be administered to treat, inhibit, reduce, or ameliorate disease (e.g., prostate cancer) or one or more symptoms of disease. Examples include but are not limited to antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabinc; Dacarbazine; DACA (N-[2-(Dimethyl-amino) ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Fluorocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofbsine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2-chloro-2'-arabinofluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'—Bis (2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl)retinamide; 13-cis retinoic acid; 3-Methyl TTNEB; 9-cis retinoic acid; fludarabine (2-F-ara-AMP); or 2-chlorodeoxyadenosine (2-Cda).

Other therapeutic compounds include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antincoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxycamptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2' deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, macroalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The agents of the invention (e.g., immune response stimulating peptides or antibodies or antigen-binding fragments thereof) can also include site-specifically conjugated molecules and moieties. Site-specific conjugation allows for the controlled stoichiometric attachment of a cytotoxic or therapeutic agent to specific residues of an agent of the invention.

The agents of the invention (e.g., immune response stimulating peptides and antibodies or antigen-binding fragments thereof), or any molecule or moiety conjugated thereto, can also be coupled to a lytic peptide. Such lytic peptides induce cell death and include, but are not limited to, streptolysin O; stoichactis toxin; phallolysin; *staphylococcus* alpha toxin; holothurin A; digitonin; melittin; lysolecithin; cardiotoxin; and cerebratulus A toxin (Kem et al, *J. Biol. Chem.* 253(16): 5752-5757, 1978). An agent of the invention can also be conjugated to a synthetic peptide that shares some sequence homology or chemical characteristics with any of the naturally occurring peptide lysins; such characteristics include, but are not limited to, linearity, positive charge, amphipathicity, and formation of alpha-helical structures in a hydrophobic environment (Leuschner et al., *Biology of Reproduction* 73:860-865, 2005). The agents of the invention (e.g., immune response stimulating peptides and antibodies or antigen-binding fragments thereof) can also be coupled to an agent that induces complement-mediated cell lysis such as, for example, the immunoglobulin $F_e$ subunit. The agents of the invention (e.g., immune response stimulating peptides and antibodies or antigen-binding fragments thereof) can also coupled to any member of the phospholipase family of enzymes (including phospholipase A, phospholipase B, phospholipase C, or phospholipase D) or to a catalytically-active subunit thereof.

An agent of the invention can also be coupled to a radioactive agent to form an agent that can be used for detection or therapeutic applications. Radioactive agents that can be used include but are not limited to Fibrinogen $^{125}$I; Fludeoxyglucose $^{18}$F; Fluorodopa $^{18}$F; Insulin $^{125}$I; Insulin $^{131}$I; lobenguane $^{123}$I; Iodipamide Sodium $^{131}$I; Iodoantipyrine $^{131}$I; Iodocholesterol $^{131}$I; lodohippurate Sodium $^{123}$I; Iodohippurate Sodium $^{125}$I; Iodohippurate Sodium $^{131}$I; Iodopyracet $^{125}$I; Iodopyracet $^{131}$I; lofetamine Hydrochloride $^{123}$I; Iomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Te Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{125}$I; or Triolein $^{131}$I.

Additionally, a radioisotope could be site-specifically conjoined to an HSA linker or HSA linker conjugate. The available reactive groups could be used to conjugate site-specific bifunctional chelating agents for labeling of radioisotopes, including $^{123}$I, $^{124}$I, $^{125}$I, $^{131}$I, $^{99m}$Tc, $^{111}$In, $^{64}$Cu, $^{67}$Cu, $^{186}$Re, $^{188}$Re, $^{177}$Lu, $^{90}$Y, $^{77}$As, $^{72}$As, $^{86}$Y, $^{89}$Zr, $^{211}$At, $^{212}$Bi, $^{213}$Bi, or $^{225}$Ac.

The agents of the invention may also be conjugated to other, not necessarily therapeutic, moieties for the purpose of enhancing, e.g., stability or localization.

Techniques for conjugating therapeutic agents to proteins, and in particular to antibodies, are well-known (e.g., Arnon et al., "Monoclonal Antibodies For Immunotargeting Of Drugs In Cancer Therapy," in Monoclonal Antibodies And Cancer Therapy (Reisfeld et al., eds., Alan R. Liss, Inc., 1985); Hellstrom et al., "Antibodies For Drug Delivery," in Controlled Drug Delivery (Robinson et al., eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al., eds., 1985); "Analysis, Results, and Future Prospective of the Therapeutic Use of Radiolabeled Antibody In Cancer Therapy," in Monoclonal Antibodies For Cancer Detection And Therapy (Baldwin et al., eds., Academic Press, 1985); Thorpe et al., *Immunol. Rev.* 62:119-58 (1982); and Doronina et al., "Development of potent monoclonal antibody auristatin conjugates for cancer therapy," *Nature Biotech.* 21:(7) 778-784 (2003)). See also, e.g., PCT publication WO 89/12624.

Additional Therapies

The agents of the invention (e.g., immune response stimulating peptides, activated immune cells, antigen-presenting cells, and antibodies or antigen-binding fragments thereof) may be administered alone or in combination with other known therapies for the treatment of cancer (e.g., prostate cancer). Such therapies for prostate cancer, for example, include, e.g., hormone therapy (e.g., androgen ablation (e.g., administration of luteinizing hormone-releasing hormone agonists (e.g., leuprolide, goserelin, or buserelin), antiandrogens (e.g., flutamide or nilutamide), adrenal gland inhibitors (e.g., ketoconazole or aminoglutethimide), or estrogen administration)), chemotherapy, radiation therapy, ultrasound therapy, or surgery (e.g., pelvic lymphadenectomy, transurethral resection of the prostate, radial prostatectomy, retropubic prostatectomy, or perineal prostatectomy). Such treatments are described in, e.g., U.S. Pat. Nos. 6,184,249; 6,245,807; 6,472,415; and 6,537,988, hereby incorporated by reference.

Administration and Dosage

Pharmaceutical formulations of a therapeutically effective amount of an agent of the invention (e.g., immune response stimulating peptides, activated immune cells, antigen-presenting cells, and antibodies or antigen-binding fragments thereof), or pharmaceutically acceptable salts thereof, can be administered orally, parenterally (e.g., intramuscular, intraperitoneal, intravenous, or subcutaneous injection, inhalation, intradermally, optical drops, or implant), nasally, vaginally, rectally, sublingually, or topically, in admixture with a pharmaceutically acceptable carrier adapted for the route of administration.

Methods well known in the art for making formulations are found, for example, in *Remington's Pharmaceutical Sciences* (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions, which can be dissolved in sterile water or some other sterile injectable medium immediately before use.

Compositions for rectal or vaginal administration are preferably suppositories, which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient (e.g., immune response stimulating peptides, activated immune cells, antigen-presenting cells, or antibodies or antigen-binding fragments thereof) in the compositions of the invention can be varied. One skilled in the art will appreciate that the exact individual dosages may be adjusted somewhat depending upon a variety of factors, including the ingredient being administered, the time of administration, the route of administration, the nature of the formulation, the rate of excretion, the nature of the subject's conditions, and the age, weight, health, and gender of the patient. In addition, the severity of the condition targeted by an agent of the invention will also have an impact on the dosage level. Generally, dosage levels of an agent of the invention of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above-identified factors.

An agent of the invention (e.g., .g., immune response stimulating peptides, activated immune cells, antigen-presenting cells, or antibodies or antigen-binding fragments thereof) can be administered in a sustained release composition, such as those described in, for example, U.S. Pat. Nos. 5,672,659 and 5,595,760, hereby incorporated by reference. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

An agent of the invention (e.g., .g., immune response stimulating peptides, activated immune cells, antigen-presenting cells, or antibodies or antigen-binding fragments thereof) can be prepared in any suitable manner. The agent may be isolated from naturally-occurring sources, recombinantly produced, or produced synthetically, identified from a library, or produced by a combination of these methods. The synthesis of short peptides is well known in the art. As described previously, a peptide portion of any of the agents of the invention can be synthesized according to standard peptide synthesis methods known in the art.

Methods for administering peptides to a subject are described, for example, in U.S. Pat. Nos. 5,830,851; 5,558,085; 5,916,582; 5,960,792; and 6,720,407, hereby incorporated by reference.

Assessment of Therapy

After therapeutic treatment with the compositions of the invention described herein, the efficacy of the treatment may be assessed by a number of methods, such as assays that measure T cell proliferation, T cell cytotoxicity, antibody production, reduction in the number of antigen-positive cells or tissues, or clinical responses. An increase in the production of antibodies or immune cells recognizing the selected antigen (e.g., an ERG or SIM2 antigen) will indicate an enhanced immune response. Similarly, an increase in specific lytic activity or specific cytokine production by the subject's immune cells or tumor regression will indicate efficacy. Efficacy may also be indicated by an improvement in or resolution of the disease (e.g., prostate cancer) associated with the reduction or disappearance of the unwanted immune response or an improvement in or resolution of the disease (e.g., prostate cancer) associated with the unwanted immune response.

Diagnostics

We have shown that ERG and SIM2 are overexpressed in prostate cancer cells and not expressed in non-cancerous prostate cells. Accordingly, the measurement of ERG and SIM2 levels can be used as a tool to diagnose prostate cancer in a subject.

The present invention features methods and compositions (e.g., immune response stimulating peptides (e.g., ERG or SIM2 peptides), activated immune cells, antigen-presenting cells, and antibodies or antigen-binding fragments thereof) for generating an immune response for the treatment of cancer (e.g., prostate cancer). The methods and compositions can include the measurement of, for example, ERG or SIM2 polypeptides, either free or bound to another molecule, or any fragments or derivatives thereof. The methods can include measurement of absolute levels of ERG or SIM2 or relative levels as compared to a normal reference. For example, a level of ERG or SIM2 in a bodily fluid of less than 5 ng/ml, 4 ng/ml, 3 ng/ml, 2 ng/ml, or less than 1 ng/l is considered to be predictive of a low risk of prostate cancer or of a good outcome in a patient diagnosed with prostate cancer. A level of ERG or SIM2 in a bodily fluid of greater than 5 ng/ml, 10 ng/ml, 20 ng/ml, 30 ng/ml, 40 ng/ml, or 50 ng/ml is considered diagnostic of prostate cancer or of a poor outcome in a subject already diagnosed with prostate cancer.

For diagnoses based on relative levels of ERG or SIM2, a subject with prostate cancer will show an alteration (e.g., an increase of 10%, 20%, 30%, 40%, 50%, 60%, 70%, 80%, 90%, or more) in the expression of an ERG or SIM2 polypeptide (or fragment thereof) as compared to a normal reference sample or level. A normal reference sample can be, for example, a sample taken from the same subject prior to the development of prostate cancer or of symptoms suggestive of prostate cancer, a sample from a subject not having prostate cancer, or a sample of a purified reference polypeptide at a known normal concentration (i.e., not indicative of prostate cancer). By "reference standard or level" is meant a value or number derived from a reference sample. A normal reference standard or level can be a value or number derived from a normal subject.

For diagnostic assays that include measuring the amount of ERG or SIM2 polypeptide, the ERG or SIM2 polypeptide can include full-length ERG or SIM2 polypeptide, degradation products, alternatively spliced isoforms of ERG or SIM2 polypeptide, enzymatic cleavage products of ERG or SIM2 polypeptide, and the like. In one example, an antibody that specifically binds ERG or SIM2 polypeptide is used for the diagnosis of prostate cancer.

Standard methods may be used to measure levels of ERG or SIM2 polypeptide in any cell, tissue, or bodily fluid, including, but not limited to, urine, blood, serum, plasma, saliva, or cerebrospinal fluid. Such methods include immunoassay, ELISA, Western blotting using antibodies that specifically bind to ERG or SIM2 polypeptide, and quantitative enzyme immunoassay techniques. Increases in the levels of ERG or SIM2 polypeptide, as compared to normal controls, are considered a positive indicator of prostate cancer.

ERG or SIM2 nucleic acid molecules, or substantially identical fragments thereof, or fragments or oligonucleotides of ERG or SIM2 that hybridize to ERG or SIM2 at high stringency may be used as a probe to monitor expression of ERG or SIM2 nucleic acid molecules in the diagnostic methods of the invention. Increases in the levels of ERG or SIM2 nucleic acid molecules, as compared to normal controls, are considered a positive indicator of prostate cancer.

The diagnostic methods described herein can be used individually or in combination with any other diagnostic method for a more accurate diagnosis of the presence of prostate cancer. Examples of additional methods for diagnosing prostate cancer include, e.g., the detection of prostate specific antigen (PSA) in prostate cells, digital rectal exams, trans-rectal ultrasounds, or biopsies (e.g., needle biopsies).

The invention also provides for a diagnostic test kit. For example, a diagnostic test kit can include antibodies that specifically bind to ERG or SIM2 polypeptide and components for detecting and evaluating binding between the antibodies and the ERG or SIM2 polypeptide. For detection, either the antibody or the ERG or SIM2 polypeptide is labeled and either the antibody or the ERG or SIM2 polypeptide is substrate-bound, such that the ERG or SIM2 polypeptide-antibody interaction can be established by determining the amount of label attached to the substrate following binding between the antibody and the ERG or SIM2 polypeptide. ELISA is a common, art-known method for detecting antibody-substrate interactions and can be provided with the kit of the invention. ERG or SIM2 polypeptides can be detected in virtually any bodily fluid, such as, e.g., urine, plasma, blood, blood serum, semen, or cerebrospinal fluid. A kit that determines an alteration in the level of ERG or SIM2 polypeptide relative to a reference, such as the level present in a normal control, is useful as a diagnostic kit in the methods of the invention. The kit can also contain a standard curve or a reference level or sample indicating levels of ERG or SIM2 that fall within the normal range and levels that would be considered diagnostic of prostate cancer. Desirably, the kit will contain instructions for the use of the kit. In one example, the kit contains instructions for the use of the kit for the diagnosis of prostate cancer. In yet another example, the kit contains instructions for the use of the kit to monitor therapeutic treatment or dosage regimens. The kit may also contain other diagnostics useful in diagnosing prostate cancer, or may be used in combination with known prostate cancer diagnostic measures.

EXAMPLES

Example 1

Identification of Putative Tumor-Associated Antigens (TAAs) for Prostate Cancer Immunotherapy In an effort to identify novel putative prostate cancer tumor-associated antigens with expression specificity for prostate cancer over normal prostate or normal non-prostate tissue, we performed a genome-wide gene expression analysis of a prostate cancer and normal prostate microarray generated in our laboratory, validated the candidate TAAs in an external, published prostate cancer tissue array data set, and excluded those with detectable expression in non-prostatic adult tissues.

First, we used the Affymetrix U133 array to evaluate gene expression in cancer and normal fresh-frozen prostate tissue specimens from our tissue repository. 250 ng of total RNA from the tissue specimens was amplified using Ambion's MessageAmp II mRNA Amplification kit. Biotin-UTP was incorporated during the overnight in vitro transcription step according to the manufacturer's protocol. Gene expression was assessed using Affymetrix's (Santa Clara, Calif.) GeneChip U133 array (Plus 2.0 chip), arrays representing whole human genome transcripts. 15 µg of cRNA was fragmented and hybridized to arrays according to the manufacturer's protocols. The image quality of scanned arrays were determined on the basis of background values, percent present calls, scaling factors, and 3'-5' ratio of β-actin and GAPDH using the BioConductor R packages. The signal value for each transcript was summarized using perfect matched (PM)-only based signal modeling algorithm described in dchip. The PM-only based signaling modeling algorithm yields fewer false positives compared to the PM-MM (mismatched) model. As such, the signal value corresponds to the absolute level of expression of a transcript. These normalized and modeled signal values for each transcript were used for further high-level bioinformatics analysis. During the calculation of model-based expression signal values, array and probe outliers were interrogated, and images spike were treated as signal outliers. The outlier detection was carried out using dchip outlier detection algorithm. A chip was considered as an outlier if the probe, single, or array outlier percentage exceeded a default threshold of 5%. When comparing two groups of samples to identify genes enriched in a given phenotype, if 90% lower confidence bound (LCB) of the fold change (FC) between the two groups was above 1.2, the corresponding gene was considered to be differentially expressed. LCB is a stringent estimate of FC and has been shown to be the better ranking statistic. It has been suggested that a criterion of selecting genes that have a LCB above 1.2 most likely corresponds to genes with an "actual" fold change of at least 2 in gene expression.

The raw gene expression data from 62 prostate cancer and 41 normal prostate specimens, published by Lapointe et al. (*Prot Natl Acad Sci USA* 101: 811-816 (2004)), were obtained from the BRB arrays archived datasets. The preprocessed data was normalized using the Z transformation. The differentially expressed genes were identified on the basis of fold change (>0.5) and Q value <0.05. The analysis identified 510 differentially expressed genes.

To prioritize the biomarker and immunotherapy targets, we needed to identify genes that are not ubiquitously expressed in all normal tissues. The gene expression data for the various human normal tissues were obtained from Gene Expression Atlas of the Genomics Institute of the Novartis Research Foundation (http://symatlas.gnf.org). Using this database, MASS normalized expression data (along with present, absent, and marginal calls for each transcript) were obtained. On the basis of present and absent calls for each transcript, a priority value was calculated. The gene absent in all tissues was given highest priority and the gene present in all tissues was given lowest priority. To further extend the list of genes, we also obtained a list of prostate specific genes by analyzing the Novartis gene expression data (Dhanasekaran et al., *Nature* 412: 822-826 (2001)). The genes that were annotated as absent on the basis of MASS calls in all normal tissues except prostate were considered prostate specific genes.

The genome-wide gene expression analysis described above identified 1063 genes overexpressed in prostate cancer compared to normal prostate. Examples of the top 100 genes identified in the expression analysis include AMACR, ERG, MMP26, THBS4, and FOXD1. Next, we validated the 1063 putative TAAs by conducting a comprehensive analysis of microarray data from a previously published data set which included 41 normal prostate tissues and 62 neoplastic prostate tissues (Lapointe et al., supra). We looked at the genes that were significantly overexpressed in prostate cancer samples for their potential to be used as biomarkers or targets for immunotherapy. A list of 426 upregulated prostate cancer genes was obtained on the basis of the fold change (>0.5) and FDR value <0.05 after pre-processing and normalizing data (Z transformation). Validation of genes that were overexpressed in prostate cancer in our data set compared to the Stanford prostate cancer array dataset implicated 145 transcripts with concordant over-expression between the array datasets.

To identify prostate cancer TAAs with the greatest specificity for prostate cancer, we then sought to exclude by in silico analysis those genes detectable in non-prostate normal human adult male tissues. For this purpose, gene expression data for various human tissues were obtained from the two studies conducted by Su et al. (*Proc Natl Acad Sci USA* 101: 6062-6067 (2004) and Ge et al. (*Genomics* 86: 127-141 (2005)). Genes that were annotated absent on the basis of MASS calls in all the normal tissues except prostate were considered as prostate specific genes. The comprehensive analysis led to the identification of 26 transcripts that are over expressed in prostate cancer samples and are highly tissue restricted (FIG. 1). These transcripts correspond to 23 genes that include ERG and SIM2. The analysis also identified 17 more genes that are present in the prostate cancer samples and absent in normal tissues.

We then performed quantitative qRT-PCR targeting each of the 23 candidate antigens. 50 ng of high-quality RNA samples (by Agilent >6.0) were reverse transcribed to obtain cDNA, and 1 µl cDNA was used for each well of RT-PCR reactions. Samples were performed in triplicates. SYBR Green PCR Master Mix (Applied Biosystems, Foster City, Calif.) was used for two-step real-time RT-PCR analysis on Applied Biosystems 7900HT Prism instrument. PCR primers for SIM2 and GAPDH were designed as SIM2-F (5'-CTTC-CCTCTGGACTCTCACG-3'; SEQ ID NO: 83), SIM2-R (5'-AGGCTGTGCCTAGCAGTGTT-3'; SEQ ID NO: 84), GAPDH-F (5'-TGCACCACCAACTGCTTAGC-3'; SEQ ID NO: 85), and GAPDH-R (5'-GGCATGGACTGTGGTCAT-GAG-3'; SEQ ID NO: 86). The expression value of SIM2 in a given sample was normalized to the corresponding expression of GAPDH. The $2^{-\Delta Ct}$ method was used to calculate relative expression of SIM2 (Haram et al., *Prostate* 68: 1517-1530 (2008) and Livak et al., *Methods* 25: 402-408 (2001)).

Figure 2:
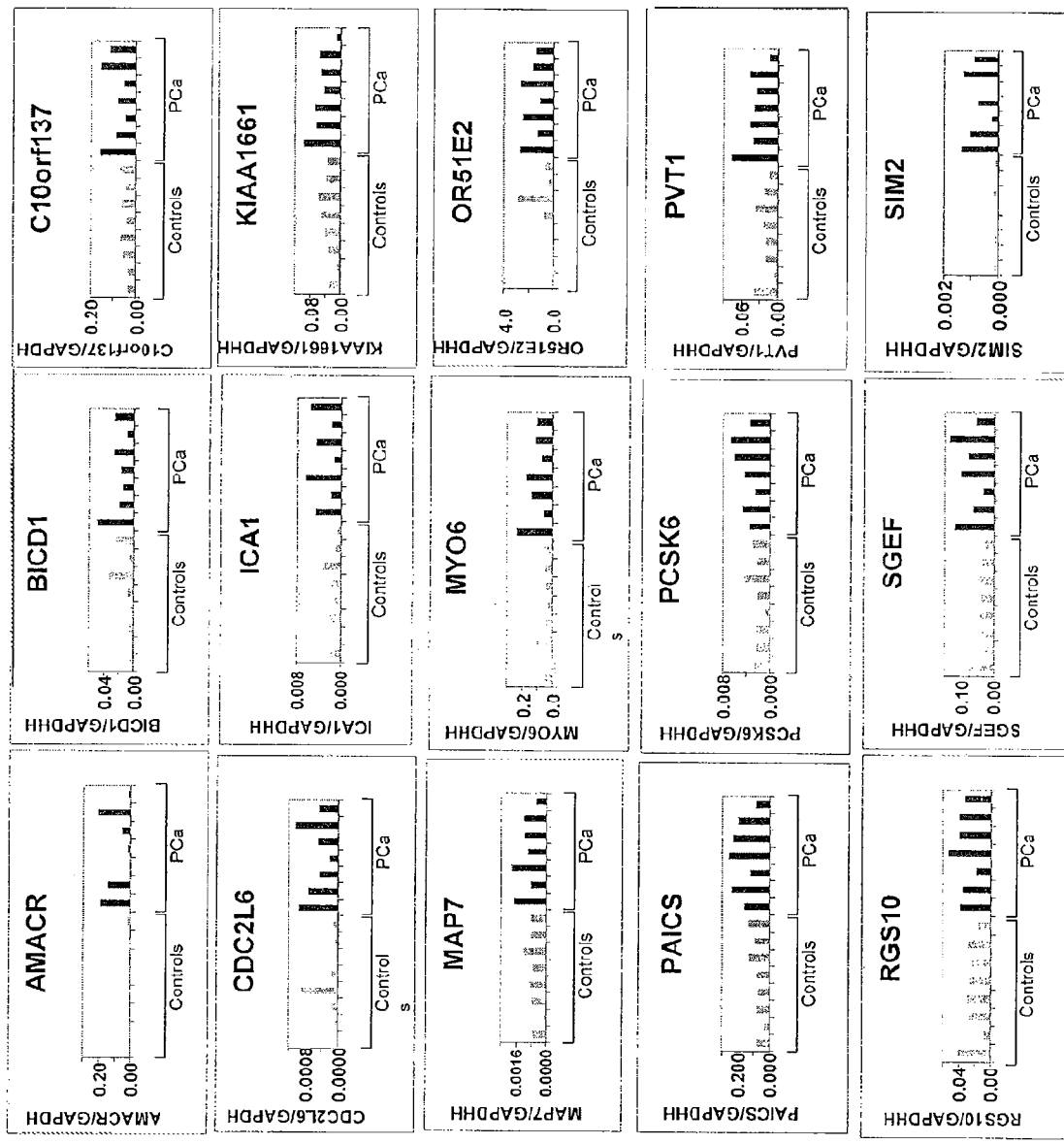
FIG. 2 is a series of graphs showing qRT-PCR validation of mRNA expression levels of individual genes (AMACR, BICD1, C10orf137, CDC2L6, ICA1, KIAA1661, MAP7, MYO6, OR51E2, PAICS, PCSK6, PVT1, RGS10, SGEF, and SIM2). qRT-PCR validation was performed using the TaqMan® gene expression assay. Only the 15 genes that were significantly overexpressed (P<0.05) in seven prostate cancer specimens compared to eight normal prostate specimens are shown here.

We confirmed that 15 of the candidate antigens (AMACR, BICD1, C10orf137, CDC2L6, ICA1, KIAA1661, MAP7, MY06, OR51E2, PAICS, PCSK6, PVT1, RGS10, SGEF, and SIM2) were overexpressed in prostate cancer (FIG. 2). Frequency of overexpression in prostate cancer for these antigens ranged from 57% to 86%. From among these 15 prostate cancer-specific antigens validated by qRT-PCR, the gene that was most consistently absent in normal prostate and had the highest frequency of expression in prostate cancer (FIG. 2) was the single-minded homolog gene (SIM2). SIM2 was overexpressed in 6 of 7 cancers we tested, but not in benign prostate tissue.

Example 2

ERG as a Target for Immunotherapy of Prostate Cancer

The selection of target therapeutic antigens is of paramount importance for the design of tumor vaccines (e.g., prostate cancer vaccines). Recent studies have shown that an intrachromosomal rearrangement of the prostate-specific promoter region in the 5' TMPRSS2 gene fusing in-frame with 3' ERG, leading to ERG overexpression, is present in 40-60% of human prostatectomy specimens. ERG is not normally expressed in the human prostate; the expression of ERG has been documented only in cultured endothelium or developing cells, though not detected at abundant levels in normal adult tissue. Moreover, unlike other ETS factors whose expression is maintained in various tissues through adulthood, ERG expression is subject to high tissue restriction.

Figure 3:
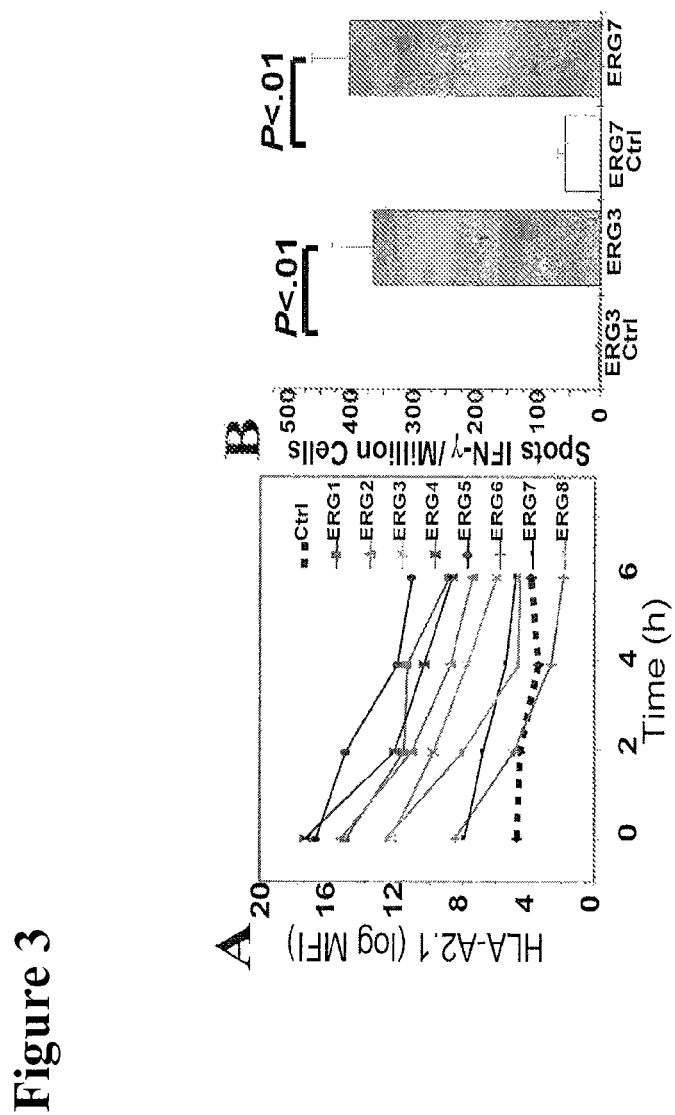
FIGS. 3A-3B are graphs showing that ERG epitopes bind human HLA-A2.1 and induce cytotoxic T lymphocytes (CTLs). Binding of predicted peptides to HLA-A2.1 was assessed using the assembly assay on T2 cells (FIG. 3A). Out of the 12 peptides tested, eight showed high-binding ability, as compared to a non-binding peptide (Ctrl). The rate of dissociation of peptides from HLA-A2.1 was determined by monitoring the decrease in HLA-A2.1 expression over time after incubation with binder peptides. Immunization of HHD mice with the eight peptides revealed three immunogenic ERG peptides, two of which are shown in FIG. 3B.

In silico analyses of the ERG amino acid sequence using different algorithms that predict MHC class I-restricted epitopes identified over 50 potential binders, of which we selected 12 putative 9-mer peptides predicted to have high affinity binding to human HLA-A2.1. Three of these 9-mer ERG peptides are described by SEQ ID NOs: 2, 3, and 4. All epitopes were from the N-terminus end of the translocation that is not deleted in most TMPRSS2:ERG fusion products, and epitope sequences were 100% homologous to their corresponding mouse orthologs. Next, we screened these peptides for binding to HLA-A2.1 and found eight with significant binding affinity (FIG. 3A). We then hypothesized that T cell tolerance to ERG could be overcome more easily than to other self-antigens because our in silico analyses identified a paucity of ERG expression in normal, human adult tissues in situ (data not shown). Accordingly, we used immunization studies to evaluate if these peptides could break tolerance to ERG, as measured by the induction of ERG epitope-specific, HLA-A2.1-restricted cytotoxic T lymphocytes (CTLs) in humanized HHD mice (i.e., mice with only human HLA-A2.1 class I MHC), and observed the induction of ERG-specific CTLs, as measured by ELISPOT (FIG. 3B).

Figure 4:
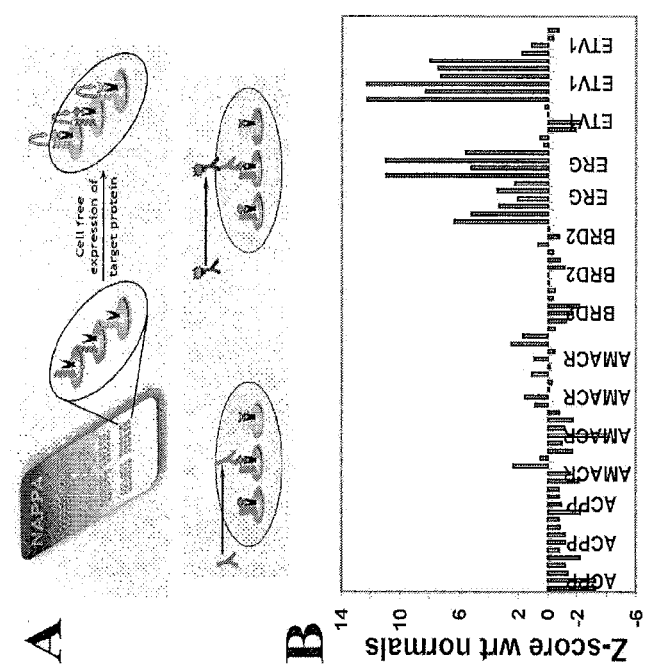
FIGS. 4A-4B show the methods and results of microarray experiments using nucleic acid programmable protein arrays (NAPPA).

In vitro studies have detected anti-ERG autoantibodies in prostate cancer patients. This was achieved by using an alternative approach to gene expression profiling for the purpose of identification of putative target prostate TAAs, mainly the detection of autoantibodies to TAA in serum of prostate cancer patients. We assembled a case-control cohort of 1000 consenting subjects who provided serum, plasma, and buffy coat. This cohort includes 35% prostate cancer cases (primary and metastatic), 55% control cases, and 10% cases with indeterminate or precancerous findings (e.g., atypia, HGPIN, or ASAP). Sera from this cohort were subjected to an initial screen using a high-density nucleic acid programmable protein array (NAPPA) to identify antigens with high incidence of autoantibodies (FIG. 4A). Several candidates were selected from the top 100 antigens resulting from this first screen, including ERG, and the NAPPA data was validated using an ELISA platform. Using this methodology, the presence of anti-ERG autoantibodies in sera from 12% of prostate cancer patients we tested (data for ERG and other TAAs are illustrated in FIG. 4B) was confirmed, providing evidence for the immunogenicity of ERG in prostate cancer patients.

Example 3

SIM2 as a Target for Immunotherapy of Prostate Cancer

To test whether sera from healthy individuals and prostate cancer patients harbor antibodies to SIM2, we used an ELISA system with in vitro expressed GST-tagged SIM2 for capture. Serum samples were collected at Harvard University and University of Michigan patient accrual sites. Written informed consent was obtained from each patient and approved by the Institutional Review Board of both institutions. All patients were over the age of 40 and were seen at the clinic because of a PSA value exceeding 2.5 ng/ml, abnormal digital rectal exam (DRE), rising PSA, or lower PSA with risk factors such as family history. The study also included men who have had previous biopsies that have not tested positive for cancer. After enrollment and blood collection, all patients received a prostate biopsy to determine the presence or absence of cancer.

A pCR-BLUNT2-topo plasmid containing human full-length SIM2 cDNA was purchased from Open Biosystems (Huntsville, Ala.). SIM2 cDNA-containing plasmid (10 pg-200 ng) went through two different PCR steps. The first PCR step contained 22.5 µl of AccuPrime Pfx Super Mix (Invitrogen) and 200 nM of each primer. The forward primers for all the genes had a shared sequence at the 5' end (AAAG-CAGGCTCCACC; SEQ ID NO: 87), but had a 3' end of 22-25 nucleotides specific to each cDNA. The reverse primers also shared a sequence at the 5' end (AAAGCAGGCTC-CACC; SEQ ID NO: 87), but the 3' end (21-27 nucleotides) of each primer was specific to each cDNA. The second PCR step included 22.5 µl of AccuPrime Pfx Super Mix (Invitrogen), 6.6 ml of the PCR product from the first step, and 200 nM of attF and attR primers. The cycling conditions for the two PCR steps were the same, except that the first PCR step was run for 35 cycles while the second PCR step was run for 5 cycles. The extension step was set at 1 minute/kb cDNA. The PCR product was run in a 1% agarose gel, gel purified, and cloned into pDONR plasmid (Invitrogen) to produce entry clones of each cDNA. Entry clones (130 ng) were used to produce expression clones using the pCITE-GST expression vector (130 ng), LR clonase II enzyme mix (2 µl), and TE buffer for a total volume of 10 µl. The reaction product (1 µl) was transformed into 50 µl of One Shot OmniMax™ 2T1 Phage-Resistant Cells according to the manufacturer's instructions. All of the TAAs were produced as GST recombinant proteins with GST at the C-terminus. As a negative control for serum antibody binding, a GST control vector was also produced using pDEST15 (Invitrogen) from which only GST would be expressed. The Kozak sequence was introduced into the original pDEST15 5' of GST so that it could be used in the mammalian cell free system.

This ELISA method is a single-antigen adaptation of the Nucleic Acid-Programmable Protein Array (NAPPA), which utilizes cDNA vectors coupled with a capture antibody and could be advantageous over traditional protein arrays since the proteins do not need to be purified (FIG. 4A). GST-ELISA plates pre-coated with GST were purchased from GE Biosciences. The plates were blocked overnight at 4° C. with PBS, 5% milk, and 0.2% Tween-20. The different TAA-GST recombinant proteins were expressed using the rabbit reticulocyte lysate cell free expression system (Promega) for 1.5 hours at 30° C. in a microcentrifuge tube according to the manufacturer's instructions. The expressed proteins were transferred to the ELISA plate and bound overnight at 4° C. The plates were washed, incubated with serum diluted 1:300 in blocking buffer for 1 hour, and then incubated for 1 hour with horseradish peroxidase linked antihuman antibodies. After washing, 100 µl of the substrate (SuperSignal ELISA Femto Maximum Sensitivity Substrate; Pierce) were added to each well, and the luminescence signal was read using Victor3 ELISA reader (no filter). Each serum was screened in duplicate. The plate also included a secondary antibody negative control and a GST control.

Figure 5:
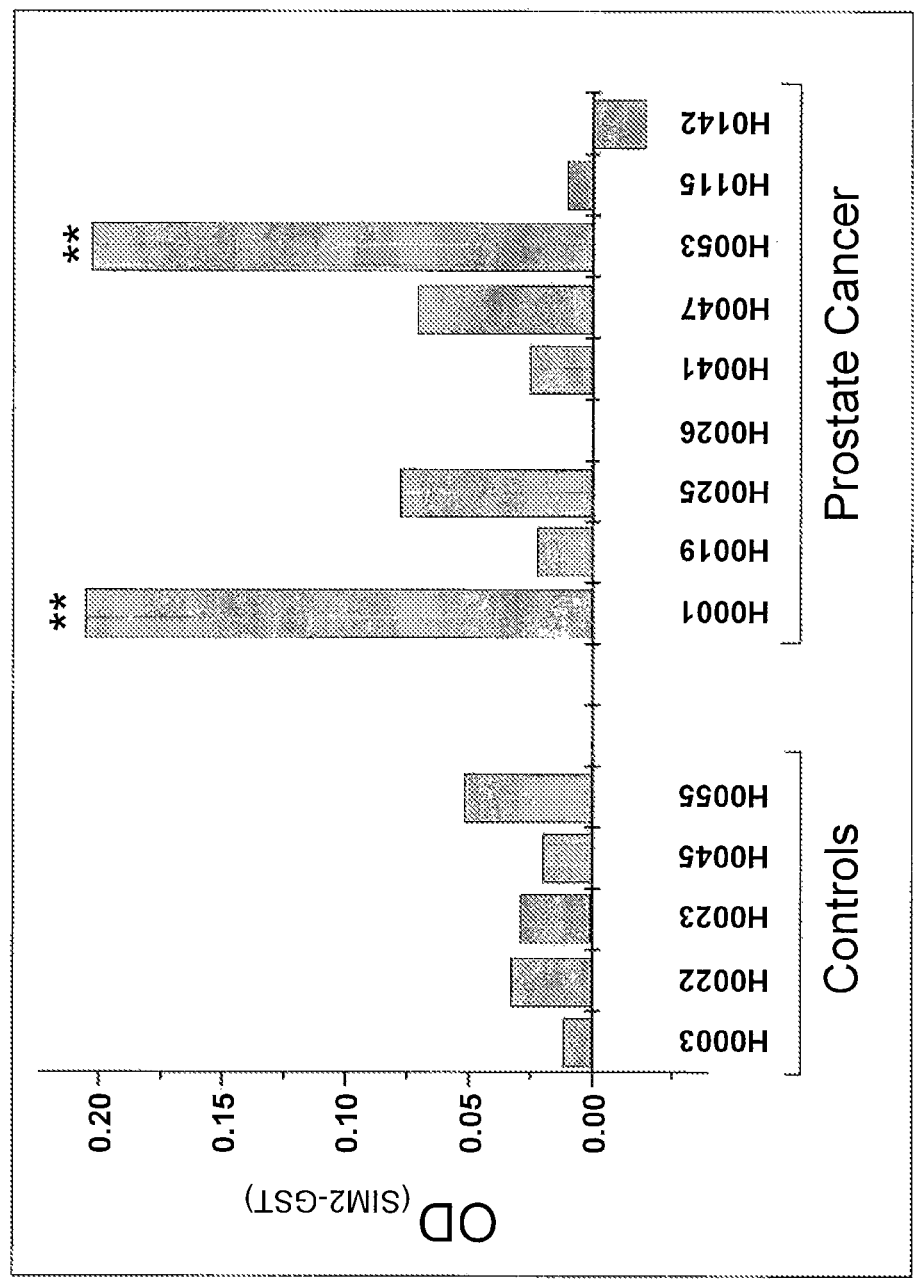
FIG. 5 is a bar graph showing that SIM2 elicits spontaneous humoral responses in prostate cancer patients. Sera from nine prostate cancer patients and five healthy donors were subjected to an in vitro, cell-free protein expression-based ELISA to detect autoantibodies to SIM2. SIM2 was expressed as a GST-tagged protein, and an anti-GST-coated plate was used in the assay. Serum antibodies that bound to immobilized SIM2 were detected using a labeled anti-human antibody. In each assay, wells containing a GST-expressing vector were used as a negative control. Signals obtained from GST wells were subtracted from those obtained from wells that contained GST-SIM2. Three experiments were performed with triplicate wells for each serum sample per experiment. Statistics were performed on the triplicates' mean and SD, and antibody amounts were plotted as the difference of OD signals produced by GST-SIM2 and GST alone.

Significant levels of autoantibody from patient sera with specific binding to SIM2 ($P<0.01$) were detected in two of the five evaluated prostate cancer samples (FIG. 5). In contrast, autoantibodies to SIM2 were not detectable in any of the nine control patients' sera (FIG. 5).

Example 4

Humanized Mouse Models as a Tool for ERG- and SIM2-Targeted Prostate Cancer Immunotherapy To test ERG-target immunotherapeutic protocols, the HHD mouse (HLA-A*0201 transgenic mouse), the Pb-ERG mouse (probasin-ERG transgenic mouse), and the Pb-ERG/Pten$^{+/-}$ mouse are used. The HHD mouse expresses human HLA-A2.1, but lacks murine MHC I. The Pb-ERG transgenic mouse exhibits prostate-restricted ERG expression and develops mouse prostatic intraepithelial neoplasia (mPIN), a precursor lesion of prostate cancer, by 12 to 14 weeks of age. The Pb-ERG/Pten$^{+/-}$ mice showed that the combination of overexpressed ERG and reduced Pten levels are causative of multifocal prostatic adenocarcinoma with complete penetrance by 6 months of age.

Xenograft models are also used in the CTL adoptive transfer phase of ERG-based immunotherapy, as they provide a fast system for the titration and evaluation of anti-tumor effects. This model is developed using the HLA-A2.1 (+) human LNCap cell line, stably expressing human ERG. A similar strategy is adopted for TAAs other than ERG in case of unavailability of transgenic mice.

For SIM2-targeted immunotherapy, the TRAMP-HHD hybrid mouse is used. The TRAMP mouse is a well-characterized model of prostate cancer, and we have previously utilized it as a model in several studies pertaining to prostate cancer genomics and immunity. Moreover, microarray data showed elevated levels of SIM2 in TRAMP prostate tumors.

Example 5

Characterization of Human HLA-A2.1-Restricted Epitopes of ERG that are Suitable Targets for Immunotherapy Mediated by A2.1-Restricted CTL The impact of developing prostate cancer on ERG-specific CTL tolerance by comparing ERG-specific CTL responsiveness in (age-matched) HHD mice to that of F1 Pb-ERG-HHD or Pb-ERG/PTEN$^{+/-}$-HHD hybrid mice before and after prostate neoplastic transformation develops is determined. Owing to the striking homology between mouse and human ERG genes, the amino acid sequences of the three epitopes we identified are 100% homologous to the murine ERG epitopes.

In preliminary data, three immunodominant epitopes of human ERG presented by human HLA-A2.1 that can break ERG-specific T cell tolerance after immunization were identified, as evidenced by induction of ERG-specific, A2.1-restricted cytotoxic T lymphocytes in humanized mice. We compare the anti-tumor efficacy of immune responses induced against each of these three immunodominant human ERG epitopes and determine whether T cell tolerance to ERG is further attenuated via androgen suppression or by inhibition of suppressive CD4/CD25 regulatory T cells by Tim-1 targeting. These preclinical studies are conducted using F1 hybrid progeny of humanized HHD mice bred with Pb-ERG mice and the PB-ERG/Pten$^{+/-}$ mouse. These models are mutually complementary as follows: the Pb-ERG transgenic mouse exhibits prostate-restricted ERG expression and, despite not developing progressive cancers, these mice allow the study of how to best exploit androgen modulation to facilitate ERG-specific T cell responses. In contrast, the PB-ERG/Pten$^{+/-}$ mouse represents multifocal prostatic adenocarcinoma with complete penetrance by six months of age and allows us to determine which of the three immunodominant ERG epitopes shows the best ability to eradicate prostate cancer in vivo.

Direct comparison of the 3 dominant epitopes' ability to eliminate ERG-induced prostate cancer is performed by passive immunization and by active immunization. We and others have previously shown that adoptive transfer of CTL specific for a model prostatic oncogene (e.g., SV40Tag in TRAMP mice) can effectively treat established prostate cancers. This experiment is performed by adoptive transfer of human A2.1-restricted, ERG-specific CTL in our PB-ERG/Pten$^{+/-}$xHHD mice. Efficacy of CTL against the three immunodominant human A2.1-restricted peptides of ERG is compared. The most effective epitope is selected for phase 1 clinical trial IND. Active immunization studies are performed to explore avenues for optimizing in situ anti-tumor responsiveness in the absence of adoptive transfer in preclinical hybrid, humanized ERG/A2.1 transgenic models. Our active immunization studies focus on exploiting androgen suppression or targeting regulatory T lymphocytes (Tregs) to attenuate ERG tolerance and improve anti-tumor efficacy in vivo. In all immunization modalities, a CTL response to a given peptide antigen is defined by the ability of splenocytes from a peptide-immunized mouse to secrete IFN-γ (measured by ELISPOT), produce granzyme B and perforin, lyse peptide-loaded FILA-A2.1-expressing cells in a cytotoxicity assay, and specifically bind peptide-tetramer complexes. Anti-tumor effects are monitored by histology (for Pb-ERG mice) and prostate tumor size (for PB-ERG/Pten$^{+/-}$ mice).

Example 6

Figure 6:
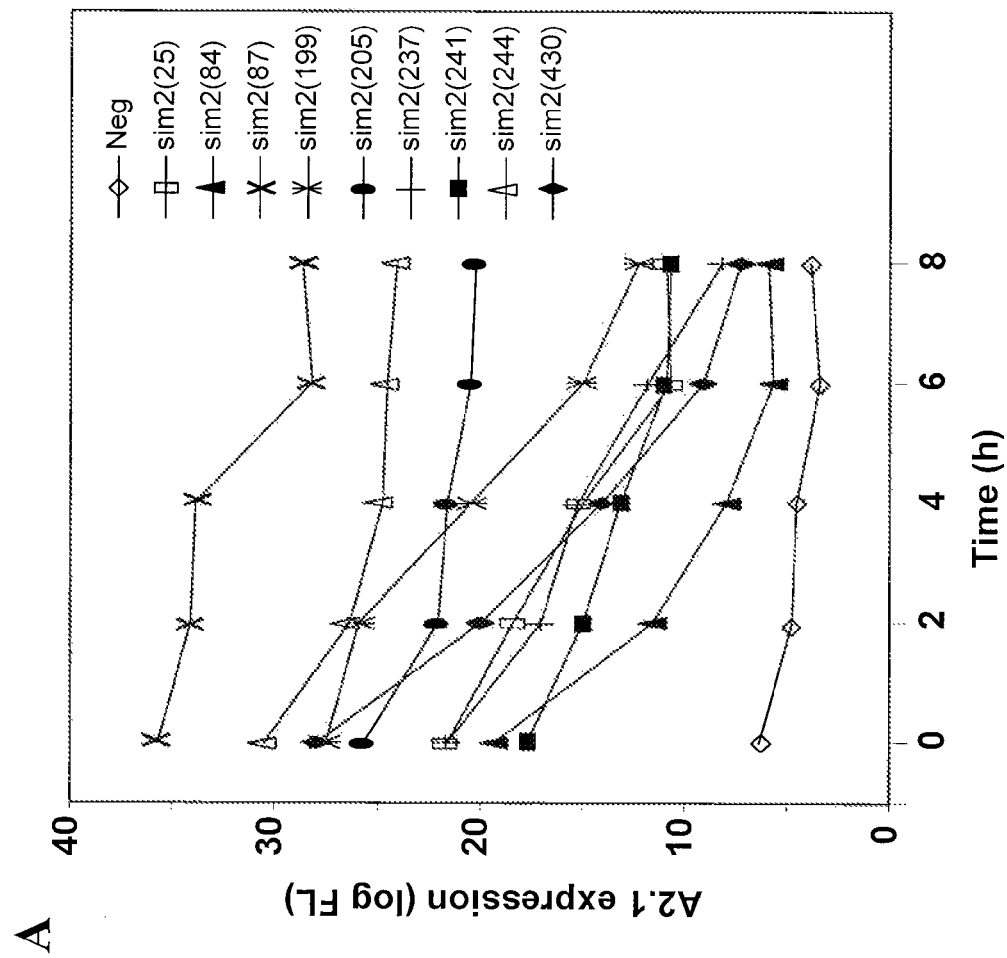
FIGS. 6A-6B are graphs showing that SIM2 harbors HLA-A2.1-restricted immunogenic epitopes. The binding to and rate of dissociation of peptides from HLA-A2.1 was determined by monitoring the decrease in HLA-A2.1 expression over time after incubation with binder peptides (FIG. 6A). Immunization of A2.1 transgenic HHD mice with the nine binding peptides revealed five immunogenic SIM2 peptides, as demonstrated by an IFN-γ ELISPOT assay (FIG. 6B).
Figure 6:
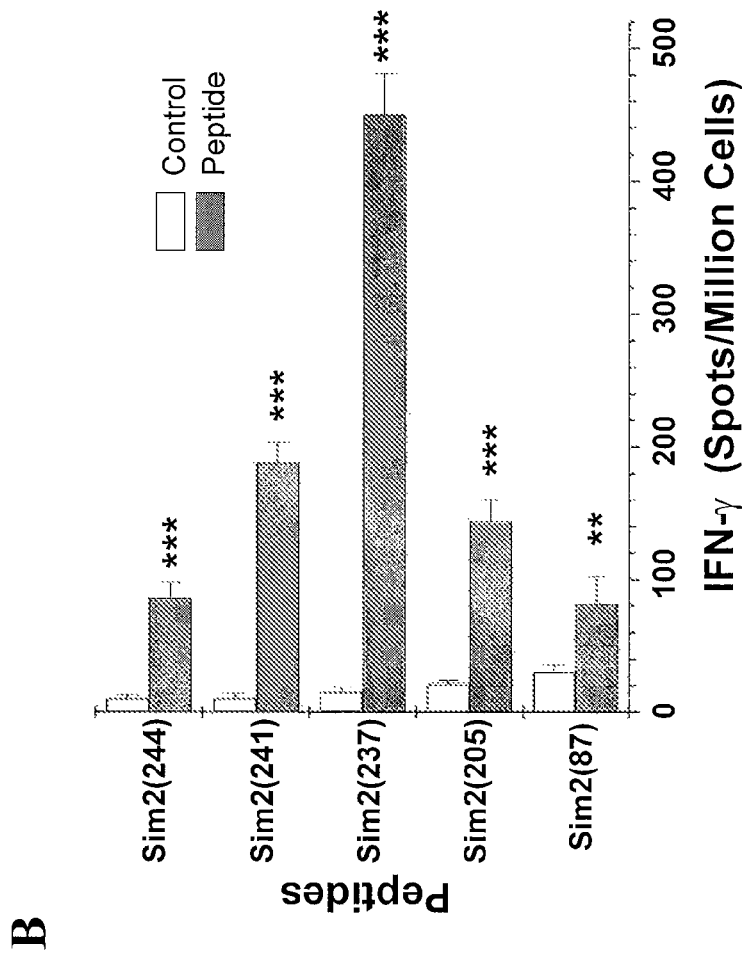

Identification and Characterization of Human HLA-A2.1-Restricted SIM2 Epitopes that are Suitable Targets for Immunotherapy Mediated by A2.1-Restricted CTL In our comprehensive analysis of microarray data from normal (41 samples) and neoplastic (62 samples) prostate tissues, we looked at the genes that are significantly overexpressed in prostate cancer for their potential to be used as biomarkers or targets for immunotherapy. A list of 343 unique prostate cancer upregulated genes was obtained on the basis of the fold change (>0.5) and FDR value <0.05 after pre-processing and normalizing data (Z transformation). For the purpose of this study, only those genes whose expression was completely absent in non-prostate normal human tissues were retained for further consideration. Gene expression data for various human tissues were obtained from the two studies conducted by Novartis and Stanford. MASS normalized expression data along with present, absent, and marginal calls for each transcript were obtained. Based on present and absent calls for each transcript, a priority value was calculated. Genes that were absent in all tissues were given highest priority. To further extend the list of genes, prostate specific genes were identified by analyzing the Stanford gene expression data. The genes that were annotated absent on the basis of MASS calls in all the normal tissues except prostate were considered as prostate specific genes. This comprehensive multi-step analysis led to a list of 57 genes, which included ERG. We selected the transcription factor SIM2 as our second target for its overexpression in most prostate cancer biopsies that were analyzed (FIG. 6) and for the absence of expression in normal tissues. Concurrent overexpression of ERG and SIM2 was observed only in a fraction of the prostate cancer biopsies we analyzed.

To predict potential HLA-A*0201-binding epitopes, candidate target TAA protein sequences are screened against various matrix patterns, which evaluate every amino acid within octomer, nonamer or decamer peptides fitting the HLA-A*0201 motif. In addition to the widely used algorithms SYFPEITHI, BIMAS, MHCPred, and RankPep, we also utilized NetCTL, PREDEP, ProPred-I, MAPPP, JenPep, NetMHC, and nHLApred for the purpose of our predictions.

Epitope candidates were evaluated for binding to HLA-A2.1 using an MHC stabilization assay. The assay is based on the ability of suitable peptides to stabilize MHC class I molecules from the T2 cell line. T2 cells lack a functional transporter associated with antigen presentation (TAP) and as a result accumulate empty, unstable class I molecules on the cell surface. These molecules on the cell surface dissociate rapidly unless they are stabilized by the addition of an appropriate binding peptide. In this assay, the flu M1 HLA-A*0201-binding peptide was used as a reference.

Briefly, T2 cells were cultured for 6 hours in serum-free IMDM (ATCC) prior to the addition of candidate peptides at a concentration of 50 μg/250×10$^3$ cells/ml and incubated overnight at 37° C. Cells were washed, and surface HLA-A2.1 molecules were stained with FITC mouse anti-human HLA-A2 mAb (clone BB7.2, Mouse IgG2b κ, BD Pharmingen) for 1 hour at 4° C. Cells were then washed three times with PBS and analyzed by flow cytometry. A negative control peptide (NEG, see FIG. 6A) and the flu matrix peptide M1 binder peptide (M1, see FIG. 6A) served as controls. The relative binding affinity of a given peptide was calculated as $MFI_{(peptide)}/MFI_{(negative\ peptide)}$. Only relative binding affinities of 1.5 or higher were considered for further testing.

T2 cells were incubated overnight with 50 μg/ml of each candidate peptide at 37° C. in serum-free Iscove's Modified Dulbecco's Medium (IMDM). Cells were then incubated with Brefeldin A (Sigma, St. Louis, Mo.) at 10 μg/ml for 1 hour, washed, and incubated at 37° C. for 0, 2, 4 or 6 hours in the presence of Brefeldin A (50 ng/ml). Cells were then stained with BB7.2 mAb. For each time point, peptide-induced HLA-A2.1 expression was calculated as the difference of the mean fluorescence of peptide-loaded T2 cells and mean fluorescence of negative peptide-loaded T2 cells. The rate of dissociation is reflected by the loss of A2.1 expression over time.

This MHC stabilization assay revealed nine SIM2 peptides that were able to stabilize HLA-A2.1 molecules, resulting in increased detection of surface A2.1 molecules with a specific monoclonal antibody (FIG. 6A). The peptide-HLA dissociation rate correlated with time and identified weak stabilizing epitopes (epitopes 84, 199, 237 and 430) and strong stabilizing epitopes (epitopes 87, 205, 241 and 244). However, epitopes with a high dissociation rate (weak stabilizers) still showed a slight binding that was above the non-binding control epitope, even after 8 hours of incubation.

These nine SIM2 peptides were then tested for their capacity to elicit in vivo CTL responses in transgenic HHD mice. Ten to 12-week old male HHD mice were injected subcutaneously at the basis of the tail with 100 m of each candidate peptide emulsified in 50 μl of Incomplete Freund's Adjuvant (IFA) and 50 μl PBS in the presence of 150 μg of the I-A$^b$ restricted HBVcore$_{128-140}$ T helper epitope (TPPAYRPPNAPIL; SEQ ID NO: 88). Ten to twelve days post-immunization, spleens were harvested and splenocytes tested for peptide-induced specific release of IFN-γ by ELISPOT. To perform the ELISPOT assays, 96-well Millipore IP plates were coated with 100 μl/well mouse IFN-γ specific capture mAb (AN18, Mabtech Inc., Mariemont, Ohio) at a concentration of 10 μg/ml in PBS overnight at 4° C. Wells were washed with PBS and saturated with RPMI/10% FCS for 1 hour at 37° C. A total of 2.5×10$^5$ splenocytes were seeded in each well in four replicates and 5×10$^4$ peptide-loaded (10 μg peptide/ml, for 2 hours at 37° C.) splenocytes pretreated with 50 μg/ml Mitomycin C for 1 hour were added to each well. Plates were incubated for 1-2 days at 37° C. in 5% $CO_2$, washed 5 times with PBS, and then incubated with 1 μg/ml of biotinylated rat anti-mouse IFN-γ mAb (R4-6A2, Mabtech Inc.) for 24 hours at 4° C. or at room temperature for 2 hours. The wells were washed, and incubated with 100 μl of diluted alkaline phosphatase-conjugated streptavidin for 1 hour at room temperature. Spots were developed by adding peroxidase substrates (5-bromo-4,3-indolyl phosphate and nitroblue tetrazolium) and counted using the ELRO4 AID ELISPOT Reader System (Autoimmun Diagnostika GmbH, Straf3berg, Germany).

We found that in vitro restimulation with SIM2(87) (TLDGFVFVV; SEQ ID NO: 6), SIM2(205) (YQIVGLVAV; SEQ ID NO: 7), SIM2(237) (SLDLKLIFL; SEQ ID NO: 8), SIM2(241) (KLIFLDSRV; SEQ ID NO: 9) and SIM2 (244) (FLDSRVTEV; SEQ ID NO: 10) induced significantly ($P<0.01$ for SIM2(87) and $P<0.001$ for other epitopes) higher numbers of splenocytes to release IFN-γ in a peptide-specific manner in an ELISPOT assay (FIG. 6B). This provides evidence that tolerance to SIM2 is circumvented through immunization of mice to these epitopes since SIM2 (and SIM1) is also expressed in other non-prostatic tissues in mice. SIM2 (25) and SIM2(199) were not immunogenic, despite their ability to bind tightly to A2.1.

We found that in vitro restimulation with SIM2(87) (TLDGFVFVV), SIM2(205) (YQIVGLVAV), SIM2(237) (SLDLKLIFL), SIM2(241) (KLIFLDSRV), and SIM2 (244) (FLDSRVTEV) induced significantly ($P<0.01$ for SIM2(87) and $P<0.001$ for other epitopes) higher numbers of splenocytes to release IFN-γ in a peptide-specific manner in an ELISPOT assay (FIG. 6B). This provides evidence that tolerance to SIM2 is circumvented through immunization of mice to these epitopes since SIM2 (and SIM1) is also expressed in other non-prostatic tissues in mice. SIM2(25) and SIM2(199) were not immunogenic, despite their ability to bind tightly to A2.1.

The potential for human HLA-A2.1-restricted, SIM2-specific immunity to impact developing prostate cancers in vivo will be evaluated in the TRAMP-HHD hybrid mouse. The TRAMP mouse is a well-characterized model of prostate cancer and we have previously utilized it as a model in several studies pertaining to prostate cancer genomics and immunity. In a genome-wide analysis, we have recently shown that SIM2 gene is overexpressed in TRAMP prostate tumors. We additionally have shown that SIM2 expression in LNCap cells is regulated by androgens, which offers the possibility of combining androgen manipulation with SIM2-targeted immunotherapy in this model.

Example 7

Figure 7:
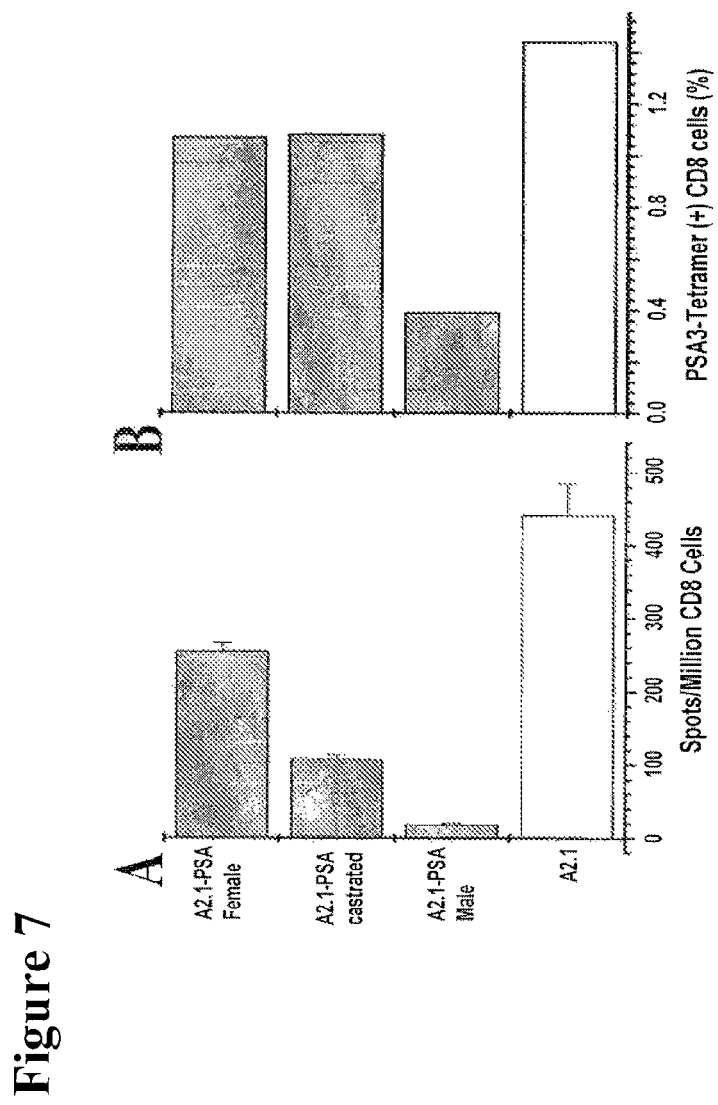
FIGS. 7A-7B are bar graphs showing that androgen suppression attenuates prostate-specific tolerance. Hybrid A2.1/PSA (males, castrated males, or females) transgenic and A2.1 mice were immunized with vac-prostate specific antigen (PSA), and splenocytes were restimulated with PSA protein-loaded dendritic cells and tested by ELISPOT (FIG. 7A) or PSA-tetramers (FIG. 7B).
Figure 8:
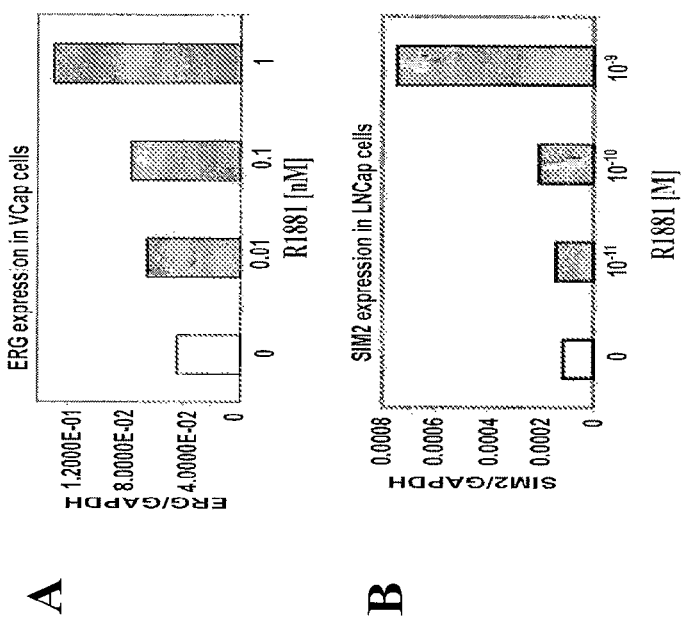
FIGS. 8A-8B are bar graphs showing qRT-PCR quantitation of ERG and SIM2 in Vcap (FIG. 8A) and LNCap cell lines (FIG. 8B), respectively, with increasing doses of androgen.

Exploitation of Androgen Ablation for Overcoming Prostate TAA-Specific Immune Tolerance The androgen-signaling pathway is critical to the development and progression of prostate cancer. Androgen ablation is a conventional therapy for prostate cancer and believed by many to enhance immunity to tumor antigens when combined to immunotherapy. It has been shown that androgen ablation in mice attenuates tolerance and raises CD4 T cell responses to flu peptide as a model prostate tumor antigen. Our studies have extended this observation to A2.1-restricted CTL responses against PSA in probasin-PSA transgenic mice. For example, hybrid A2.1/PSA (males, castrated males, or females) transgenic and A2.1 mice were immunized with vac-prostate specific antigen (PSA), and splenocytes were restimulated with PSA protein-loaded dendritic cells and tested by ELISPOT (FIG. 7A) or PSA-tetramers (FIG. 7B), showing that androgen suppression attenuates prostate-specific tolerance. Additionally, androgen ablative therapy in men has been shown to result in enhanced T cell infiltration into benign and malignant prostate tissue. We now exploit androgen responsiveness of TMPRSS2-ERG fusion and SIM2 gene (FIG. 8) to attenuate ERG- and SIM2-specific immune tolerance.

Our preliminary data (FIG. 8A) are consistent with the well-established positive correlation of ERG expression with androgen. We assess the effect of castration on the outcome of active immunization comparing the three immunodominant ERG peptides for their ability to induce ERG-specific CTL in Pb-ERG-HHD and to reduce tumor growth in PB-ERG/Pten$^{+/-}$-HHD mice.

Like ERG, SIM2 expression is dependent on androgens (FIG. 8B), likely due to the location of SIM2 gene in a region rich in androgen regulatory elements on chromosome 21. Our microarray data revealed increased expression of SIM2 expression in prostate tumors from TRAMP mice. The effect of androgen ablation on immune tolerance to SIM2 and on prostate tumor growth by castration of male TRAMP-HHD hybrid mice is tested, followed by active immunization with immunogenic A2.1-restricted SIM2 peptides.

Example 8

Figure 9:
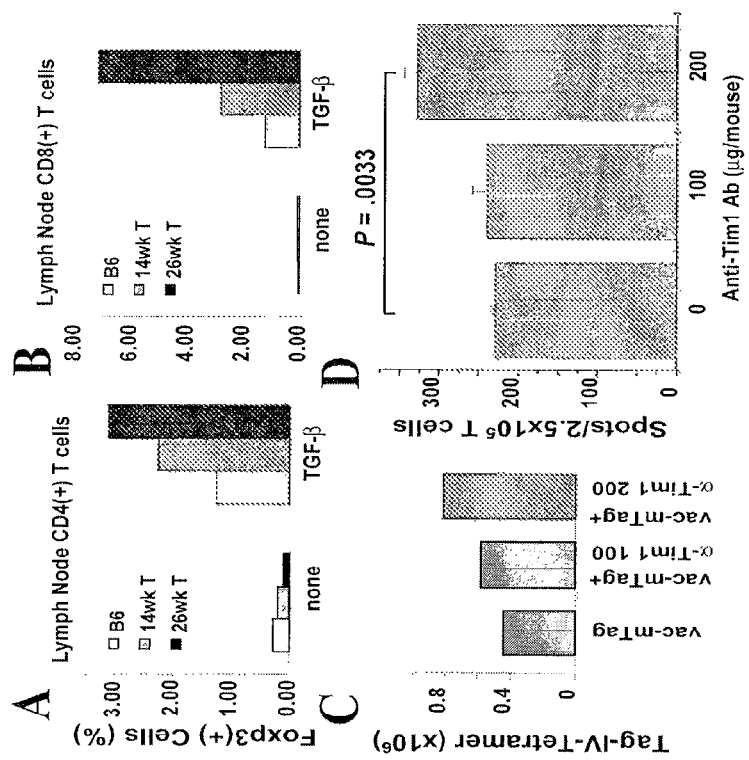
FIGS. 9A-9D are bar graphs showing the increased generation of regulatory T lymphocytes (Tregs) in mice with prostate cancer and the effect of anti-Tim-1 agonist antibody.
Figure 10:
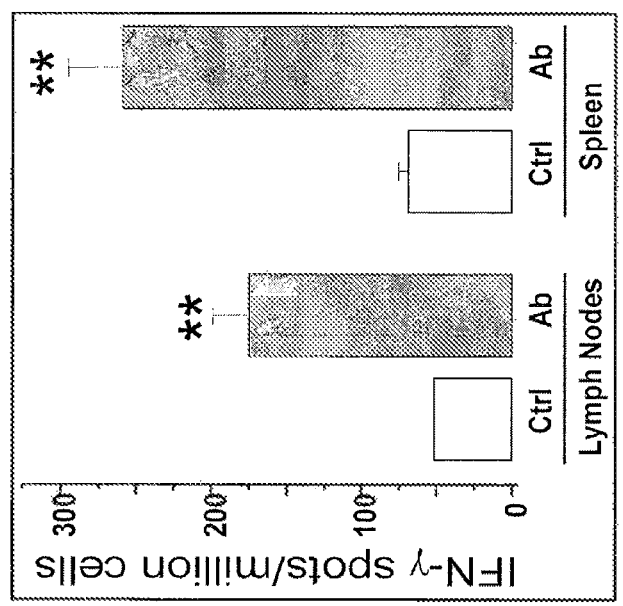
FIG. 10 is a bar graph showing that anti-Tim-1Ab treatment elicits enhanced CTL responses to Tag in TRAMP mice (P<0.01 versus an isotype control).

Manipulation of the T Cell Immunoglobulin-Mucin-1 (Tim-1) Pathway for Overcoming Prostate TAA-Specific Immune Tolerance Regulatory T lymphocytes (Tregs) severely impede anti-tumor immune responses in various cancers. To investigate the ability of stimulating T cells through the Tim-1 receptor to interfere with the rise of Treg cells and the onset of immune tolerance to TAA, we crossed the TRAMP mouse with GFP-Foxp3-KI mouse. We found that naïve CD4 T and CD8 T cells from the prostate-draining lymph nodes of TRAMP-GFP-Foxp3 hybrid mice exhibit an increased rate of conversion to Treg cells after treatment with anti-CD3/CD28+TGF-β (FIGS. 9A and 9B). This elevated susceptibility to TGF-β-induced differentiation is enhanced in aged mice. This novel observation might explain why prostate cancer development parallels an increase in Treg in both tumors and peripheral blood. Depletion of Tregs prior to the administration of cancer vaccines strengthens tumor immunity in non-prostate models. T cell immunoglobulin-mucin-1 (Tim-1) stimulation with an agonistic anti-Tim 1 antibody (Ab), a Tim 4-Ig fusion protein or activation by Tim-4+DCs is able to polarize T cells into a TH1 and TH17 dominant phenotypes and subvert tolerance and Tregs. We first tested the ability of the anti-Tim-1 Ab by immunizing B6 mice with a recombinant, Tag-expressing vaccinia and providing different doses of the Ab at the time of immunization. We have found that agonist anti-Tim-1 Ab induced a significant increase in Tag-specific CTL as judged by Tag-tetramer specificity and IFN-γ production by CD8 cells (FIGS. 9C and 9D). This finding is consistent with a previous report where an agonist anti-Tim-1 antibody enhanced antigen-specific cellular proliferation and IFN-γ production in mice immunized with inactivated influenza virus. We then sought to assess the CTL enhancing ability of the Ab in adult TRAMP-GFP-Foxp3 mice using the same strategy. Similarly, Ab treatment resulted in elevated Tag-specific CTL in both spleen and prostate-draining lymph nodes (FIG. 10). Together, our findings support our hypothesis that interference with the Tim-1/Tim-4 interaction by antibodies or fusion proteins will enhance responsiveness to active immunization with ERG or SIM2. The effect of Tim-1 manipulation in various mouse models of prostate cancer is tested by administering the agonist anti-Tim-1 monoclonal antibody concomitantly with antigen under an active and passive immunotherapy regimen and also in combination with androgen ablation.

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. An isolated immune response stimulating peptide comprising a sequence having at least 90% sequence identity to SEQ ID NO:37, wherein said peptide has at least 12 but fewer than 50 amino acid residues.

2. The peptide of claim 1, wherein said immune response stimulating peptide comprises the sequence of SEQ ID NO: 37.

3. The peptide of claim 1, wherein said peptide is capable of activating immune cells in a mammalian host when bound to an antigen-presenting molecule.

4. The peptide of claim 3, wherein said immune cells are cytotoxic T lymphocytes.

5. The peptide of claim 3, wherein said antigen-presenting molecule is an HLA molecule.

6. The peptide of claim 5, wherein said HLA molecule is an HLA class I molecule.

7. A composition comprising the peptide of claim 1 and a pharmaceutically acceptable diluent, excipient, carrier, or adjuvant.

8. The composition of claim 7, wherein said composition is a vaccine.

9. The composition of claim 7, further comprising an adjuvant or an additional therapeutic agent.

10. The composition of claim 7, wherein said peptide is conjugated to a heterologous compound.

11. The peptide of claim 10, wherein said heterologous compound is a therapeutic or cytotoxic agent.

* * * * *

UNITED STATES PATENT AND TRADEMARK OFFICE
CERTIFICATE OF CORRECTION

| | | |
|---|---|---|
| PATENT NO. | : 8,455,615 B2 | Page 1 of 1 |
| APPLICATION NO. | : 12/990438 | |
| DATED | : June 4, 2013 | |
| INVENTOR(S) | : Martin G. Sanda et al. | |

It is certified that error appears in the above-identified patent and that said Letters Patent is hereby corrected as shown below:

Please add the following statement to Column 1 of the specification after the Cross Reference to Related Applications Statement:

STATEMENT REGARDING FEDERALLY SPONSORED RESEARCH

This invention was made with government support under CA113913 and DK065313, awarded by the National Institute of Health, and CA090381, which was awarded by the National Cancer Institute. The government has certain rights in the invention.

Signed and Sealed this
First Day of October, 2013

Teresa Stanek Rea
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,455,615 B2 |
| APPLICATION NO. | : 12/990438 |
| DATED | : June 4, 2013 |
| INVENTOR(S) | : Martin G. Sanda et al. |

It is certified that error appears in the above-identified patent and that said Letters Patent is hereby corrected as shown below:

On the title page item (56), col. 2, line 1, under FOREIGN PATENT DOCUMENTS, replace "WO02-72627" with --WO 2002-72627--.

In the Specification

Column 5, Line 50, replace "hem opoietic" with --hemopoietic--.

Column 17, Line 46, replace "A. metantrone" with --Ametantrone--;

Line 55, replace "Combretestatin A-4" with --Combretastatin A-4--;

Line 56, replace "Cytarabinc" with --Cytarabine--.

Column 18, Line 6, replace "Ilmofbsine" with --Ilmofosine--;

Line 19, replace "PeploycinSulfate" with --Peplomycin Sulfate--;

Line 45, replace "mechlor ethamine" with --mechlorethamine--;

Line 47, replace "Nnitrosourea" with --N-nitrosourea--.

Column 19, Line 7, replace "antincoplaston" with --antineoplaston--;

Line 10, replace "argininedeaminase" with --arginine deaminase--;

Line 27, replace "conagcnin" with --conagenin--;

Line 66, replace "ifepristone" with --mifepristone--.

Signed and Sealed this
Fourth Day of August, 2015

Michelle K. Lee
*Director of the United States Patent and Trademark Office*

CERTIFICATE OF CORRECTION (continued)
U.S. Pat. No. 8,455,615 B2

Column 21, Line 35-36, replace "lobenguane" with --Iobenguane--;

Line 37, replace "lodohippurate Sodium" with --Iodohippurate Sodium--;

Line 39, replace "lofetamine Hydrochloride" with --Iofetamine Hydrochloride--.

Column 27, Line 18, replace "MASS" with --MAS5--;

Line 27, replace "MASS" with --MAS5--;

Line 56, replace "MASS" with --MAS5--.

Column 28, Line 12, replace "$2^{-\Delta Ct}$" with --$2^{-\Delta\Delta Ct}$--.

Column 31, Line 66, replace "FILA-A2.1" with --HLA-A2.1--.

Column 32, Line 23, replace "MASS" with --MAS5--;

Line 31, replace "MASS" with --MAS5--.

Column 33, Line 30, replace "100 m" with --100 μg--;

Line 57, replace "Straf3berg" with --Straßberg--.